United States Patent
Cox et al.

(10) Patent No.: US 12,274,736 B2
(45) Date of Patent: *Apr. 15, 2025

(54) HEMATOPOIETIC GROWTH FACTOR PROTEINS AND ANALOGS THEREOF AND ANGIOTENSIN CONVERTING ENZYME INHIBITORS FOR TREATMENT OF RADIATION EXPOSURE

(71) Applicants: Bolder BioTechnology, Inc., Boulder, CO (US); Indiana University Research and Technology Corporation, Indianapolis, IN (US); The Medical College of Wisconsin, Inc., Milwaukee, WI (US)

(72) Inventors: George N. Cox, Louisville, CO (US); Christie M. Orschell, Indianapolis, IN (US); Meetha Manek Medhora, Brookfield, WI (US); Brian Fish, Waukesha, WI (US)

(73) Assignees: Bolder Biotechnology, Inc., Boulder, CO (US); Indiana University Research and Technology Corporation, Indianapolis, IN (US); The Medical College of Wisconsin, Inc., Milwaukee, WI (US)

( * ) Notice: Subject to any disclaimer, the term of this patent is extended or adjusted under 35 U.S.C. 154(b) by 337 days.

This patent is subject to a terminal disclaimer.

(21) Appl. No.: 17/548,929

(22) Filed: Dec. 13, 2021

(65) Prior Publication Data
US 2022/0202903 A1 Jun. 30, 2022

Related U.S. Application Data

(63) Continuation of application No. 15/269,746, filed on Sep. 19, 2016, now Pat. No. 11,229,683.

(60) Provisional application No. 62/220,819, filed on Sep. 18, 2015.

(51) Int. Cl.
*A61K 38/20* (2006.01)
*A61K 38/05* (2006.01)
*A61K 38/19* (2006.01)

(52) U.S. Cl.
CPC .......... *A61K 38/2073* (2013.01); *A61K 38/05* (2013.01); *A61K 38/193* (2013.01)

(58) Field of Classification Search
CPC . A61K 38/193; A61K 38/2073; A62K 38/193
See application file for complete search history.

(56) References Cited

U.S. PATENT DOCUMENTS

| | | | |
|---|---|---|---|
| 4,810,643 A | 3/1989 | Souza | |
| 5,437,863 A | 8/1995 | Williams et al. | |
| 6,066,317 A | 5/2000 | Yang et al. | |
| 6,555,660 B2 | 4/2003 | Nissen et al. | |
| 6,608,183 B1 | 8/2003 | Cox, III | |
| 6,753,165 B1 | 6/2004 | Cox et al. | |
| 7,148,333 B2 | 12/2006 | Cox, III | |
| 7,214,779 B2 | 5/2007 | Cox, III | |
| 7,232,885 B2 | 6/2007 | Cox, III | |
| 7,253,267 B2 | 8/2007 | Cox, III | |
| 7,306,931 B2 | 12/2007 | Rosendahl et al. | |
| 7,309,781 B2 | 12/2007 | Cox, III | |
| 7,371,370 B2 | 5/2008 | Sarkar et al. | |
| 7,495,087 B2 | 2/2009 | Cox, III | |
| 7,754,855 B1 | 7/2010 | Cox, III et al. | |
| 7,994,124 B2 | 8/2011 | Cox | |
| 8,133,480 B2 | 3/2012 | Cox, III | |
| 8,748,392 B2 | 6/2014 | Cox, III | |
| 8,841,249 B2 | 9/2014 | Johansen et al. | |
| 9,320,777 B2 | 4/2016 | Cox et al. | |
| 10,016,485 B2 | 7/2018 | Cox et al. | |
| 10,653,752 B2 | 5/2020 | Cox et al. | |
| 11,229,683 B2 | 1/2022 | Cox et al. | |
| 2003/0064480 A1 | 4/2003 | Lauffer et al. | |
| 2006/0286069 A1 | 12/2006 | Nissen et al. | |
| 2010/0183543 A1 | 7/2010 | Yonehiro et al. | |

FOREIGN PATENT DOCUMENTS

| | | |
|---|---|---|
| WO | WO 01/87925 | 11/2001 |
| WO | WO 2005/027978 | 3/2005 |
| WO | WO 2010/033884 | 3/2010 |

OTHER PUBLICATIONS

Medhora et al. Radiat. Re. 182, 545-555(2014) (Year: 2014).*
Plett et al. Health Phys. Jan. 2014; 106(1):7-20 (Year: 2014).*
Aagaard et al., "RNAi therapeutics: Principles, prospects and challenges," Advanced Drug Delivery Reviews, 2007, vol. 59, Iss. 2-3, pp. 75-86.
Abdel-Meguide et al., "Three-dimensional structure of a genetically engineered variant of porcine growth hormone," Proc. Natl. Acad. Sci. USA, 1987, vol. 84, pp. 6434-6437.
Arakawa et al., "Cysteine 17 of recombinant human granulocyte colony-stimulating factor is partially solvent-exposed," J. Protein Chem., 1993, vol. 12, pp. 525-531.
Barshishat-Kupper et al., "Captopril modulates hypoxia-inducible factors and erythropoietin responses in a murine model of total body irradiation", Experimental Hematology, 2011, vol. 39, Iss. 3, pp. 293-304.
Basile et al., "HemaMax™, a Recombinant Human Interleukin-12, Is a Potent Mitigator of Acute Radiation Injury in Mice and Non-Human Primates," PLOS ONE, 2012, vol. 7, Iss. 2, e30434.

(Continued)

*Primary Examiner* — Vanessa L. Ford
*Assistant Examiner* — Sandra Carter
(74) *Attorney, Agent, or Firm* — Sheridan Ross, P.C.

(57) ABSTRACT

Methods and compositions comprising hematopoietic growth factor proteins and/or protein analogs thereof and/or combinations thereof and angiotensin converting enzyme inhibitors to treat the acute and long term adverse effects of radiation exposure in subjects who have been or will be exposed to radiation are disclosed.

20 Claims, 44 Drawing Sheets

Specification includes a Sequence Listing.

(56) References Cited

OTHER PUBLICATIONS

Bazan, "Haemopoietic receptors and helical cytokines," Immunology Today, 1990, vol. 11, pp. 350-354.

Bertho et al., "Comparison of autologous cell therapy and granulocyte-colony-stimulating factor (G-CS) injection vs. G-CSF injection alone for the treatment of acute radiation syndrome in a non-human primate model," Int. J. Radiation Oncology Biol. Phys., 2005, vol. 63, pp. 911-920.

Blumberg et al., "Interleukin 20: Discovery, Receptor Identification, and Role in Epidermal Function," Cell, 2001, vol. 104, pp. 9-19.

Boerma et al. "Local administration of interleukin-11 ameliorates intestinal radiation injury in rats," Cancer Res., 2007, vol. 67, pp. 9501-9506.

Booth et al., "Acute Gastrointestinal Syndrome in High-Dose Irradiated Mice," Health Physics, 2012, vol. 103, Iss. 4, pp. 383-399.

Booth et al., "Protection against mucosal injury by growth factors and cytokines," J National Cancer Institute Monographs, 2001, vol. 29, pp. 16-20.

Bork, "Powers and Pitfalls in Sequence Analysis: The 70% Hurdle," Genome Research, 2000, vol. 10, Iss. 4, pp. 398-400.

Bowen et al., "Relationship between molecular mass and duration of activity of polyethylene glycol conjugated granulocyte colony-stimulating factor mutein," Exp. Hematol., 1999, vol. 27, pp. 425-432.

Bowie et al., "Deciphering the message in protein sequences: tolerance to amino acid substitutions," Science, 1990, vol. 247, Iss. 4948, pp. 1306-1310.

Brown et al. "Tolerance of single, but not multiple, amino acid replacements in antibody VH CDR 2: a means of minimizing B cell wastage from somatic hypermutation?," Journal of Immunology, 1996, vol. 156, Iss. 9, pp. 3285-3291.

Burgess et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111, Iss. 5, pp. 2129-2138.

Cairo et al., "Modulation of neonatal rat myeloid kinetics resulting in peripheral neutrophilia by single pulse administration of Rh granulocyte-macrophage colony-stimulating factor and Rh granulocyte colony-stimulating factor," Biol. Neonate, 1991, vol. 59, pp. 13-21.

Cairo, "Dose reductions and delays: limitations of myelosuppressive chemotherapy," Oncology, 2000, vol. 14, pp. 21-31.

Cantrell et al., "Cloning, sequence, and expression of a human granulocyte/macrophage colony-stimulating factor," Proc. Natl Acad. Sci. USA, 1985, vol. 85, pp. 6250-6254.

Carlo-Stella et al., "Use of recombinant human growth hormone (rhGH) plus recombinant human granulocyte colony-stimulating factor (rhG-CSF) for the mobilization and collection of CD34+ cells in poor mobilizers," Blood, 2004, vol. 103, pp. 3287-3295.

Charrier et al., "Inhibition of angiotensin I-converting enzyme induces radioprotection by preserving murine hematopoietic short-term reconstituting cells," Blood, 2004, vol. 104, Iss. 4 pp. 978-985.

Chen et al., "Growth hormone mitigates against lethal irradiation and enhances hematologic and immune recovery in mice and non-human primates," PLoS One (www.plosone.org), 2010, vol. 5(6), e11056, 12 pages.

Chua et al., "Survival Efficacy of the PEGylated G-CSFs Maxy-G34 and Neulasta in a Mouse Model of Lethal H-ARS, and Residual Bone Marrow Damage in Treated Survivors," Health Physics, 2014, vol. 106, Iss. 1, pp. 21-38.

Cleland et al., "A Novel Long-Acting Human Growth Hormone Fusion Protein (VRS-317): Enhanced In Vivo Potency and Half-Life," Journal of Pharmaceutical Sciences, 2012, vol. 101, Iss. 8, pp. 2744-2754.

Cox et al., "A long-acting, monoPEGylated human growth hormone analog is a potent stimulator of weight gain and bone growth in hypophysectomized rats," Endocrinology, 2007, vol. 148, pp. 1590-1597.

Cox et al., "Enhanced circulating half-life and hematopoietic properties of a human granulocyte colony-stimulating factor (G-CSF)-immunoglobulin fusion protein," Exp. Hematol., 2004, vol. 32, pp. 441-449.

Dainiak et al., "The Hematologist and Radiation Casualties," Am. Soc. Hematology, 2003, pp. 473-496.

Davis et al. "Timing of captopril administration determines radiation protection or radiation sensitization in a murine model of total body irradiation," Experimental Hematology, 2010, vol. 38, Iss. 4, pp. 270-281.

Davis et al. "Response to Moulder et al., Re: Davis et al., Timing of captopril administration determines radiation protection or radiation sensitization in a murine model of total body irradiation," Experimental Hematology, 2011, vol. 39, No. 5, pp. 522-524.

Day et al. "Enhanced hematopoietic protection from radiation by the combination of genistein and captopril," International Immunopharmacology, 2013, 15: 348-356.

De Vos et al., "Human Growth Hormone and Extracellular Domain of Its Receptor: Crystal Structure of the Complex," Science, 1992, vol. 255, pp. 306-312.

DiCarlo et al., "Radiation injury after a nuclear detonation: medical consequences and the need for scarce resource allocation," Disaster Med Public Health Prep, 2011, vol. 5(Suppl. 1), pp. S32-44.

Doan et al., "Epidermal growth factor regulates hematopoietic regeneration following radiation injury" Nature Medicine, 2013, 19: 295-304.

Doerks et al., "Protein annotation: detective work for function prediction," Trends in Genetics, 1998, vol. 14, Iss. 6, pp. 248-250.

Doherty et al., "Site-Specific PEGylation of Engineered Cysteine Analogues of Recombinant Human Granulocyte-Macrophage Colony-Stimulating Factor," Bioconjugate Chemistry, 2005, vol. 16, pp. 1291-1298.

Drouet et al., "Cytokines in combination to treat radiation-induced myelosuppression: evaluation of SCF + glycosylated EPO + PEGylated G-CSF as an emergency treatment in highly irradiated monkeys," Hematologica, 2008, vol. 93, pp. 465-466.

Du et al., "A bone marrow stromal-derived growth factor, Interleukin-11, stimulates recovery of small intestinal mucosal cells after cytoablative therapy," Blood, 1994, vol. 83, pp. 33-37.

Du et al., Interleukin-11: review of molecular, cell biology and clinical use. Blood, 1997, vol. 89, pp. 3897-3908.

Ersoy et al., "Effect of Growth Hormone on small intestinal homeostasis relation to cellular mediators IGF-I and IGFBP-3," World J Gastroenterol, 2009, vol. 15, pp. 5418-5424.

Fares et al., "Design of a long-acting follitropin agonist by fusing the C-terminal sequence of the chorionic gonadotropin ß subunit to the follitropin ß subunit," Proceedings of the National Academy of Sciences of the United States of America, 1992, vol. 89, Iss. 10, pp. 4304-4308.

Farese et al. "The Ability of Filgrastim to Mitigate Mortality Following LD50/60 Total-body Irradiation Is Administration Time-Dependent," Health Physics, 2014, vol. 106, Iss. 1, pp. 39-47.

Farese et al., "A Nonhuman Primate Model of the Hematopoietic Acute Radiation Syndrome Plus Medical Management," Health Physics, 2012, vol. 103, Iss. 4, pp. 367-382.

Farese et al., "Filgrastim Improves Survival in Lethally Irradiated Nonhuman Primate," Radiation Research, 2013, 179, Iss. 1, pp. 89-100.

Farese et al. "Combination Protocols of Cytokine Therapy With Interleukin-3 and Granulocyte-Macrophage Colony-Stimulating Factor in a Primate Model of Radiation-Induced Marrow Aplasia," Blood, Nov. 1993, vol. 82, No. 10, pp. 3012-3018.

Gao et al., "Enalapril Mitigates Radiation-Induced Pneumonitis and Pulmonary Fibrosis if Started 35 Days after Whole-Thorax Irradiation," Radiation Research, 2013, vol. 180, Iss. 5. pp. 546-552.

Ghosh et al. "Renin-Angiotensin System Suppression Mitigates Experimental Radiation Pneumonitis," International Journal of Radiation Oncology*Biology*Physics, 2009, vol. 75, Iss. 5, pp. 1528-1536.

(56) References Cited

OTHER PUBLICATIONS

Glaspy, "Hematopoietic management in oncology practice. Part 1. Myeloid growth factors," Oncology, 2003, vol. 17, pp. 1593-1603.
Goeddel et al., "Direct expression in Escherichia coli of a DNA sequence coding for human growth hormone," Nature, 1979, vol. 281(5732), pp. 544-548.
Goldman, "Preclinical biology of Interleukin-11: a multifunctional hematopoietic cytokine with potent thrombopoietic activity," Stem Cells, 1995, vol. 13, pp. 462-471.
Goodson et al., "Site-Directed Pegylation of Recombinant Interleukin-2 at its Glycosylation Site," Biotechnology, 1990, vol. 8, pp. 343-346.
Gordon et al. "A phase I trial of recombinant human interleukin-11 (neumega rhIL-11 growth factor) in women with breast cancer receiving chemotherapy," Blood, 1996, vol. 87, Iss. 9, pp. 3615-3624.
Hao et al., "Effects of Recombinant Human Interleukin 11 on Thrombocytopenia and Neutropenia in Irradiated Rhesus Monkeys," Radiation Res., 2004, vol. 162, pp. 157-163.
Himburg et al., "Pleiotrophin mediates hematopoietic regeneration via activation of RAS," The Journal of Clinical Investigation, 2014, vol. 124, Iss, 11, pp. 4753-4758.
Howarth et al., "Effects of insulin-like growth factor-I administration on radiation enteritis in rats," Scand J Gastroenterol, 2003, vol. 32, pp. 1118-1124.
Howarth, "Insulin-like growth factor-I and the gastrointestinal system: therapeutic indications and safety implications," J. Nutr., 2003, vol. 133, pp. 2109-2112.
Ihle et al., "Signaling Through the Hematopoietic Cytokine Receptors," Annu. Rev. Immunol., 1995, vol. 13, pp. 369-398.
Kawashima et al., "Molecular cloning of cDNA encoding adipogenesis inhibitory factor and identity with Interleukin-11," FEBS Letts., 1991, vol. 283, pp. 199-202.
Kiessling et al., "Functional expression of the Interleukin-11 receptor alpha chain and evidence of antiapoptotic effects in human colonic epithelial cells," J. Biol. Chem., 2004, vol. 279:, pp. 10304-10315.
Kitamura et al., "Establishment and characterization of a unique human cell line that proliferates dependently on GM-CSF, IL-3, or erythropoietin," J.Cell. Physiol., 1989, vol. 140, 323-334.
Kma et al., "Angiotensin Converting Enzyme Inhibitors Mitigate Collagen Synthesis Induced by a Single Dose of Radiation to the Whole Thorax," Journal of Radiation Research, 2012, vol. 53, Iss. 1, pp. 10-17.
Kubota et al., "Structural characterization of natural and recombinant human granulocyte colony-stimulating factors," J. Biochem., 1990, vol. 107, pp. 486-492.
Lazar et al., "Transforming growth factor alpha: mutation of aspartic acid 47 and leucine 48 results in different biological activities," Molecular and Cellular Biology, 1988, vol. 8, Iss. 3, pp. 1247-1252.
Lee et al., "Isolation of cDNA for a human granulocyte-macrophage colony-stimulating factor by functional expression in mammalian cells," Proc. Natl. Acad. Sci. USA, 1985, vol. 82, pp. 4360-4364.
Leonard et al., "Recombinant human interleukin-11 stimulates multilineage hematopoietic recovery in mice after a myelosuppressive regimen of sublethal irradiation and carboplatin," Blood, 1994, vol. 83, pp. 1499-1506.
Lu et al., "Disulfide and secondary structures of recombinant human granulocyte colony-stimulating factor," Arch. Biochem. Biophys., 1989, vol. 268, pp. 81-92.
Macvittie, "Defining the full therapeutic potential of recombinant growth factors in the post radiation-accident environment: the effect of supportive care plus administration of G-CSF," Health Phys., 2005, vol. 89, pp. 546-555.
Martial et al., "Human growth hormone: complementary DNA cloning and expression in bacteria," Science, 1979, vol. 205(4406), pp. 602-607.
Mayer et al., "Efficacy of recombinant human granulocyte-macrophage colony-stimulating factor in rhesus monkeys," Ann N Y Acad Sci, 1987, vol. 511, pp. 17-29.
Mayer et al., "In vitro and in vivo activity of human recombinant granulocyte-macrophage colony-stimulating factor in dogs," Exp. Hematol., 1990, vol. 18, pp. 1026-1033.
Mayer et al., "Recombinant human GM-CSF induces leukocytosis and activates peripheral blood polymorphonuclear neutrophils in nonhuman primates," Blood, 1987, vol. 70, pp. 206-213.
Mayer et al., "Recombinant murine granulocyte-macrophage colony-stimulating factor augments neutrophil recovery and enhances resistance to infections in myelosuppressed mice," J. Infect. Dis., 1991, vol. 163, pp. 584-590.
Medhora et al., "Mitigation of Radiation-Induced Injuries to Multiple Organs in Rats by FDA-Approved Drugs and Supportive Care," International Journal of Radiation Oncology, Biology, Physics, 2014, vol. 90, Iss. 1 Suppl., Abstract 3527, pp. S809-S810.
Medhora et al., "Model Development and Use of ACE Inhibitors for Preclinical Mitigation of Radiation-Induced Injury to Multiple Organs," Radiation Research, 2014, vol. 182, Iss. 5, pp. 545-555.
Molteni et al., "Control of radiation-induced pneumopathy and lung fibrosis by angiotensin-converting enzyme inhibitors and an angiotensin II type 1 receptor blocker," International Journal of Radiation Biology, 2000, vol. 76, Iss. 4, pp. 523-532.
Mott et al., "Four-helix bundle growth factors and their receptors: protein-protein interactions," Current Opinion in Structural Biology, 1995, vol. 5, pp. 114-121.
Moulder et al., "Captopril and Losartan for Mitigation of Renal Injury Caused by Single-Dose Total-Body Irradiation," Radiation Research, 2011, vol. 175, Iss. 1, pp. 29-36.
Moulder et al., "Mitigation of experimental radiation nephropathy by renin-equivalent doses of angiotensin converting enzyme inhibitors," International Journal of Radiation Biology, 2014, vol. 90, Iss. 9, pp. 762-768.
Moulder et al., "Re: Davis et al., "Timing of captopril administration determines radiation protection or radiation sensitization in a murine model of total body irradiation"," Experimental Hematology, 2011, vol. 39, Iss. 5, pp. 521-524.
Mylonas et al., "Growth Hormone and insulin-like growth factor I protect intestinal cells from radiation induced apoptosis," Mol Cell Endocrinol., 2000, vol. 160, pp. 115-122.
Nagata et al., "Molecular cloning and expression of cDNA for human granulocyte colony-stimulating factor," Nature, 1986, vol. 319(6052), pp. 415-418.
Nagata et al., "The chromosomal gene structure and two mRNAs for human granulocyte colony-stimulating factor," EMBO J., 1986, vol. 5, pp. 575-581.
Neta et al., "Cytokines in radiation injury," Blood, 1988, vol. 72, pp. 1093-1095.
Neta et al., "Interdependence of the radioprotective effects of human recombinant interleukin-1 alpha, tumor necrosis factor, granulocyte colony-stimulating factor, and murine recombinant granulocyte-macrophage colony-stimulating factor," J. Immunol, 1988, vol. 140, pp. 108-111.
Paul et al., "Molecular cloning of a cDNA encoding interleukin 11, a stromal cell-derived lymphopoietic and hematopoietic cytokine," Proc. Natl. Acad. Sci. USA, 1990, vol. 87, pp. 7512-7516.
Picken et al., "Nucleotide sequence of the gene for heat-stable enterotoxin II of *Escherichia coli*," Infect. Immun., 1983, vol. 42, pp. 269-275.
Plett et al., "Establishing a Murine Model of the Hematopoietic Syndrome of the Acute Radiation Syndrome," Health Physics, 2012, vol. 103, Iss. 4, pp. 343-355.
Plett et al., "PEGylated G-CSF (BBT-015), GM-CSF (BBT-007), and IL-11 (BBT-059) Analogs Enhance Survival and Hematopoietic Cell Recovery in a Mouse Model of the Hematopoietic Syndrome of the Acute Radiation Syndrome," Health Physics, 2014, vol. 106, Iss. 1, pp. 7-20.
Potten, "Interleukin-11 protects the clonogenic stem cells in murine small-intestinal crypts from impairment of their reproductive capacity by radiation," Int. J. Cancer, 1995, vol. 62, pp. 356-361.
Potten, "Protection of the small intestinal clonogenic stem cells from radiation-induced damage by pretreatment with interleukin-11 also increases murine survival time," Stem Cells, 1996, vol. 14, pp. 452-459.

(56) References Cited

OTHER PUBLICATIONS

Raguso et al., "Protective effects of recombinant growth hormone on intestinal mucosa in rats receiving abdominal radiotherapy," Clin Nutr., 2002, vol. 21, pp. 487-490.

Redlich et al., "IL-11 enhances survival and decreases TNF production after radiation-induced thoracic injury," J Immunology, 1996, vol. 157, pp. 1705-1710.

Rosendahl et al., "Site-specific protein PEGylation: application to cysteine analogs of recombinant human granulocyte colony-stimulating factor," BioProcess International, 2005, vol. 3, pp. 52-62.

Schuening et al., "Effect of recombinant human granulocyte colony-stimulating factor on hematopoiesis of normal dogs and on hematopoietic recovery after otherwise lethal total body irradiation," Blood, 1989, vol. 74, pp. 1308-1313.

Schwertschlag et al., "Hematopoietic, immunomodulatory and epithelial effects of interleukin-11," Leukemia, 1999, vol. 13, pp. 1307-1315.

Sirohi et al., "Use of physiological doses of human growth hormone in haematological patients receiving intensive chemotherapy promotes haematopoietic recovery: a double blind randomized, placebo-controlled study," Bone Marrow Transplant., 2007, vol. 39, pp. 115-120.

Sitaraman et al., "Oprelvekin. Genetics Institute," Curr. Opin. Investig. Drugs, 2001, vol. 2, pp. 1395-1400.

Skolnick et al., "From genes to protein structure and function: novel applications of computational approaches in the genomic era," Trends in Biotechnology, 2000, vol. 18, Iss. 1, pp. 34-39.

Sonis et al., "Defining mechanisms of action of interleukin-11 on the progression of radiation-induced oral mucositis in hamsters," Oral Oncology, 2000, vol. 36, pp. 373-381.

Souza et al., "Recombinant Human Granulocyte Colony-Stimulating Factor: Effects on Normal and Leukemic Myeloid Cells," Science, 1986, vol. 232, pp. 61-65.

Stribling et al., "Aerosol gene delivery in vivo," Proceedings of the National Academy of Sciences of the United States of America, 1992, vol. 89, Iss. 23, pp. 11277-11281.

Swierczewska et al. "What is the future of PEGylated therapies?" Expert Opinion on Emerging Drugs, 2015, vol. 20, No. 4, pp. 531-536.

Takagi et al., "Enhanced pharmacological activity of recombinant human interleukin-11 (rhIL-11) by chemical modification with polyethylene glycol," J. Controlled Research, 2007, vol. 119, pp. 271-278.

Tokuriki et al., "Stability effects of mutations and protein evolvability," Current Opinion in Structural Biology, 2009, vol. 19, Iss. 5, pp. 596-604.

Uckun et al., "In vivo radioprotective effects of recombinant human granulocyte colony- stimulating factor in lethally irradiated mice," Blood, 1990, vol. 75, pp. 638-645.

Vajdos et al., "Comprehensive Functional Maps of the Antigen-binding Site of an Anti-ErbB2 Antibody Obtained with Shotgun Scanning Mutagenesis," Journal of Molecular Biology, 2002, vol. 320, Iss. 2, pp. 415-428.

Van Der Meeren et al., "Administration of recombinant human interleukin-11 after supralethal radiation exposure promotes survival in mice: interactive effect with thrombopoietin," Radiat. Res., 2002, vol. 157, pp. 642-649.

Waddick et al., "Comparative Analysis of the in vivo Radioprotective Effects of Recombinant Granulocyte Colony-Stimulating Factor (G-CSF), Recombinant Granulocyte-Macrohage CSF, and Their Combination," Blood, 1991, vol. 77, pp. 2364-2371.

Warzocha et al., "Antisense Strategy: Biological Utility and Prospects in the Treatment of Hematological Malignancies," Leukemia and Lymphoma, 2009, vol. 24. Iss. 3-4, pp. 267-281.

Waselenko et al., "Medical Management of the Acute Radiation Syndrome: Recommendations of the Strategic National Stockpile Radiation Working Group", Annals of Internal Medicine, 2004, vol. 140, Iss. 12, pp. 1037-1051.

Wells, "Additivity of mutational effects in proteins," Biochemistry, 1990, vol. 29, Iss. 37, pp. 8509-8517.

Wen et al., "Erythropoietin Structure-Function Relationships," J Biol. Chem., 1994, vol. 269, pp. 22839-22846.

Werle et al. "Strategies to improve plasma half life time of peptide and protein drugs," Amino Acids, 2006, vol. 30 pp. 351-367.

Whisstock et al. "Prediction of protein function from protein sequence and structure," Quarterly Reviews of Biophysics, 2003, vol. 36, No. 3, pp. 307-340.

Yang, "Interleukin-11 (IL-11) and its receptor: Biology and potential clinical applications in thrombocytopenia states," Chapter 13 of Cytokines: Interleukins and Their Receptors, Kurzrock et al., eds., Academic Publishers, Norwell, MA, 1995, pp. 321-340.

Zhang et al., "Effects of human growth hormone on hematopoietic recovery of rats receiving chemotherapy," Chemotherapy, 2008, vol. 54, pp. 447-455.

Official Action for U.S. Appl. No. 15/269,746 mailed Jun. 15, 2018, 6 pages.

Official Action for U.S. Appl. No. 15/269,746 mailed Dec. 11, 2018, 23 pages.

Official Action for U.S. Appl. No. 15/269,746 mailed Jul. 29, 2019, 22 pages.

Official Action for U.S. Appl. No. 15/269,746, dated Jun. 26, 2020 36 pages.

Official Action for U.S. Appl. No. 15/269,746, dated Mar. 3, 2021 43 pages.

Notice of Allowance for U.S. Appl. No. 15/269,746, dated Sep. 17, 2021 14 pages.

\* cited by examiner

HEMATOPOIETIC GROWTH FACTOR PROTEINS AND ANALOGS THEREOF AND ANGIOTENSIN CONVERTING ENZYME INHIBITORS FOR TREATMENT OF RADIATION EXPOSURE

CROSS-REFERENCE TO RELATED APPLICATIONS

This application claims is a continuation of U.S. patent application Ser. No. 15/269,746, filed Sep. 19, 2016, now U.S. Pat. No. 11,229,683, which claims the benefit of priority under 35 U.S.C. § 119 (e) to U.S. Provisional Patent Application No. 62/220,819, filed Aug. 18, 2015. The entire disclosures of each of which are incorporated herein by reference.

GOVERNMENT RIGHTS

This invention was made with government support under Grant Nos. U01 AI107340, U01 AI107305, 1RC1AI081294-01, R44 AI084288, and 5U19AI067734 from the National Institutes of Health. The Government has certain rights in the invention.

REFERENCE TO A SEQUENCE LISTING

This application contains a Sequence Listing submitted electronically as a text file by EFS-Web. The text file, named "4152-21_Sequence_Listing_ST25", has a size in bytes of 11 KB, and was recorded on 16 Sep. 2016. The information contained in the text file is incorporated herein by reference in its entirety pursuant to 37 CFR § 1.52(e)(5).

FIELD OF THE INVENTION

The present invention generally relates to methods and compositions for use of hematopoietic growth factor proteins and/or protein analogs thereof and/or combinations thereof and angiotensin converting enzyme inhibitors to treat subjects who have been exposed to radiation.

BACKGROUND OF THE INVENTION

Acute, high dose radiation exposure (a high dose of radiation received over a short period of time) causes a well characterized set of radiation dose-dependent and time-dependent organ malfunctions (Acute Radiation Syndrome or ARS), which can lead to severe morbidity and death. Tissues differ in their sensitivities to radiation exposure, primarily due to differences in the number and turnover of stem cells within each tissue. Bone marrow is one of the most radiation-sensitive tissues, and one of the first signs of acute radiation exposure is bone marrow aplasia and myelosuppression. Myelosuppression is a reduction in bone marrow activity that results in reduced numbers of mature blood cells, including but not limited to neutrophils, white blood cells, red blood cells, platelets, lymphocytes, monocytes, granulocytes, dendritic cells, etc. A myelosuppressive dose of radiation is a dose of radiation sufficient to cause myelosuppression. Subjects exposed to greater than 2 Gy radiation typically develop myelosuppression and severe neutropenia (reduced numbers of neutrophils), leukopenia (reduced numbers of white blood cells), anemia (reduced numbers of red blood cells), thrombocytopenia (reduced numbers of platelets) and lymphopenia (reduced numbers of lymphocytes), within 2-3 weeks of exposure, and many subjects die from hematopoietic failure within 30 to 60 days following high dose radiation exposure. Subjects exposed to greater than 8 Gy total body irradiation (TBI) develop damage to other organ systems such as the gastrointestinal system, lung, heart and kidney over the ensuing months and years (referred to as delayed effects of acute radiation exposure or DEARE). In a hospital setting, subjects may be exposed to high dose radiation (typically fractionated so that the total dose is divided into several smaller doses that are administered over time) as a means of treating disease, e.g., cancer. Complications of radiation exposure often limit the amount of radiation treatment cancer patients receive, which reduces effectiveness of the radiation treatment and reduces overall patient survival. Subjects may be acutely exposed to high dose total body irradiation or partial body irradiation (PBI) as a result of detonation of a nuclear device, or leakage of radioactivity from a facility containing radioactive substances such as a nuclear power plant.

Several hematopoietic growth factors (HGFs) such as granulocyte colony-stimulating factor (G-CSF), granulocyte-macrophage colony-stimulating factor (GM-CSF), interleukin-11 (IL-11), interleukin-12 (IL-12), stem cell factor (SCF), erythropoietin (EPO), thrombopoietin (TPO), epidermal growth factor (EGF), transforming growth factor alpha (TGF alpha), pleotropin, growth hormone (GH), insulin-like growth factor 1 (IGF-1), insulin-like growth factor 2 (IGF-2), and other proteins have been shown to accelerate hematopoietic recovery and improve survival of irradiated animals when administered within 24 hours of radiation exposure (MacVittie T J, et al. (2005) Defining the full therapeutic potential of recombinant growth factors in the post radiation-accident environment: the effect of supportive care plus administration of G-CSF. Health Phys 89: 546-555; Van der Meeren A., et al. (2002) Administration of recombinant human interleukin-11 after supralethal radiation exposure promotes survival in mice: interactive effect with thrombopoietin. Radiat. Res. 157: 642-649; Drouet, M. et al. (2008) Cytokines in combination to treat radiation-induced myelosuppression: evaluation of SCF+glycosylated EPO+PEGylated G-CSF as an emergency treatment in highly irradiated monkeys. Hematologica 93: 465-466; 2012; Plett, P A, et al. (2012) Establishing a murine model of the Hematopoietic Syndrome of the Acute Radiation Syndrome. Health Physics 103: 343-355; Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20; Basile L A, et al. (2012) HemaMax™, a recombinant human interleukin-12, is a potent mitigator of acute radiation injury in mice and non-human primates. PLOS ONE 7(2):e30434, doi:10.1371/journal.pone.0030434; Doan P L, et al. (2013) Epidermal growth factor regulates hematopoietic regeneration following radiation injury. Nature Medicine 19: 295-304; Himburg H A, et al. (2014) Pleotropin mediates hematopoietic regeneration via activation of RAS. The Journal of Clinical Investigation 124: 4753-4758). Angiotensin-converting enzyme (ACE) inhibitors (ACEI) such as captopril and enalapril, have been shown to decrease radiation-induced damage to lung (pneumonitis and fibrosis) and kidney (nephropathy), and to reduce morbidity and mortality from radiation (Molteni et. al., 2000 Control of radiation-induced pneumopahty and lung fibrosis by angiotensin-converting enzyme inhibitors and an angiotensin II type 1 receptor blocker. Int J Radiat Biol v. 76: pg 523-532; Ghosh S N, et al. (2009) Renin-angiotensin system suppression mitigates experimental pneumonitis. Int J Radiat Oncol Biol Phys 75: 1528-1536; Kma L, et al. (2012) Angiotensin Converting Enzyme Inhibitors Mitigate Collagen Synthesis Induced by a Single Dose of Radiation to the Whole Thorax. Journal of Radiation Research (Japan) 53(1):10-17; Gao F, et al. (2013) Enalapril mitigates radiation-induced pneumonitis and pulmonary fibrosis if started 35 days after whole-thorax irradiation. Radiation Research 180: 546-552; Moulder et al., 2011 Captopril and losartan for mitigation of renal injury caused by single-dose total-body irradiation. Radiat Res 175(1):29-36). ACEIs also have been shown to increase 30 day survival of irradiated rodents when administered beginning one hour following radiation exposure and continuing treatment for 30 days, or by beginning treatment one day following radiation exposure and continuing treatment for 7 days (Davis T A, et al. (2010) Timing of captopril administration determines radiation protection or radiation sensitization in a murine model of total body irradiation. Experimental Hematology 38: 270-281; Day R M, et al. (2013) Enhanced hematopoietic protection from radiation by the combination of genistein and captopril. International Immunopharmacology 15: 348-356).

Recombinant G-CSF is a 19 kDa HGF protein that stimulates proliferation and differentiation of bone marrow cells into granulocytes (neutrophils, eosinophils and basophils). G-CSF has been shown to increase survival of irradiated dogs, monkeys and mice when administered by subcutaneous (sc) injection 24 h prior to radiation exposure or by daily subcutaneous injection for 16 or more days beginning 20 to 24 h following radiation exposure (Uckun F M, et al. (1990) In vivo radioprotective effects of recombinant human granulocyte colony-stimulating factor in lethally irradiated mice. Blood 75: 638-645; MacVittie T J, et al. (2005) Defining the full therapeutic potential of recombinant growth factors in the post radiation-accident environment: the effect of supportive care plus administration of G-CSF. Health Phys 89: 546-555; Plett, P A, et al. (2012) Establishing a murine model of the Hematopoietic Syndrome of the Acute Radiation Syndrome. Health Physics 103: 343-355; Farese A M, et al. (2012) A nonhuman primate model of the hematopoietic syndrome plus medical management. Health Physics 103: 367-382; Farese, A M, et al. (2013) Filgrastim improves survival in lethally irradiated nonhuman primates. Radiation Research 179: 89-100). Long-acting G-CSF analogs were shown to increase 30-day survival of irradiated mice when administered by sc injection once 24 h following radiation exposure or when administered as 9 every other day sc injections beginning 24 h following radiation exposure (Chua H L, et al. (2014) Survival efficacy of the PEGylated G-CSFs Maxy-G34 and neulasta in a mouse model of lethal H-ARS, and residual bone marrow damage in survivors. Health Physics 106: 21-38; Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20).

Recombinant GM-CSF is a 14 kDa HGF that regulates proliferation, differentiation and functional activities of a variety of hematopoietic cells of the granulocyte and macrophage lineages, including neutrophils, eosinophils, basophils, monocytes, macrophages, and dendritic cells. Recombinant human GMCSF is used in a variety of hematopoietic disorders, including reducing the severity of chemotherapy-induced neutropenia, accelerating hematopoietic recovery following bone marrow transplantation and mobilizing blood progenitor cells for transplantation. A long-acting murine GM-CSF analog has been shown to increase 30-day survival of irradiated mice when administered as 3 or 9 every other day sc injections beginning 24 h following radiation exposure (Plett, P. A., et al (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20).

Recombinant human IL-11 is a 19 kDa HGF that stimulates the proliferation and differentiation of megakaryocytes into platelets (Du X X and Williams D A (1997) Interleukin-11: review of molecular, cell biology and clinical use. Blood 89: 3897-3908). Recombinant IL-11 is used to ameliorate thrombocytopenia following myelosuppressive chemotherapy in cancer patients (Gordon M. S., et al. (1996) A Phase 1 trial of recombinant human interleukin-11 (neumega rhIL-11 growth factor) in women with breast cancer receiving chemotherapy. Blood 87: 3615-3624). IL-11 administration results in higher platelet nadirs and accelerates platelet recovery in cancer patients receiving chemotherapy. IL-11 has been shown to increase survival of 8 Gy-irradiated mice when administered by daily intraperitoneal (ip) injection for 5 days beginning 2 h following radiation exposure (Van der Meeren A., et al. (2002) Administration of recombinant human interleukin-11 after supralethal radiation exposure promotes survival in mice: interactive effect with thrombopoietin. Radiat. Res. 157: 642-649). A long-acting IL-11 analog was shown to increase 30-day survival of irradiated mice when administered by sc injection once 24 h following radiation exposure or when administered as 3 every other day sc injections beginning 24 h following radiation exposure (Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20).

Recombinant human IL-12 is an HGF that has been shown to increase survival of irradiated monkeys and mice when administered 24 h following radiation exposure (Basile L A, et al. (2012) HemaMax™, a recombinant human interleukin-12, is a potent mitigator of acute radiation injury in mice and non-human primates. PLOS ONE 7(2):e30434, doi:10.1371/journal.pone.0030434).

TPO is an HGF that regulates platelet production. TPO administration has been shown to increase survival of irradiated mice when administered for five days by ip injection beginning 2 h post-irradiation (Van der Meeren A., et al. (2002) Administration of recombinant human interleukin-11 after supralethal radiation exposure promotes survival in mice: interactive effect with thrombopoietin. Radiat. Res. 157: 642-649). Higher survival rates were observed when mice were treated for 5 days with both TPO and IL-11 by ip injection beginning 2 h following radiation exposure (Van der Meeren A., et al. (2002) Administration of recombinant human interleukin-11 after supralethal radiation exposure promotes survival in mice: interactive effect with thrombopoietin. Radiat. Res. 157: 642-649).

A cocktail of EPO, SCF, and G-CSF accelerated hematopoietic recovery in irradiated monkeys (Drouet, M., et al. (2008) Cytokines in combination to treat radiation-induced myelosuppression: evaluation of SCF+glycosylated EPO+ PEGylated G-CSF as an emergency treatment in highly irradiated monkeys. Hematologica 93: 465-466). Administering EPO at 2 h and day 8 post-irradiation along with SCF, FLT-3 ligand, TPO and IL-3 at 2 h and 24 h post-irradiation increased 30-day survival of 9 Gy-irradiated mice (Drouet, M., et al. (2008) Cytokines in combination to treat radiation-induced myelosuppression: evaluation of SCF+glycosylated EPO+PEGylated G-CSF as an emergency treatment in highly irradiated monkeys. Hematologica 93: 465-466). EPO by itself did not increase survival of irradiated mice.

Growth Hormone (GH) is a 22 kDa protein that is the body's primary hormone for regulating somatic growth during development. GH also exerts hematopoietic effects such as stimulating expansion and recovery of hematopoietic cells following chemotherapy (Zhang et al., 2008 Effects of human growth hormone on haematopoietic recovery of rats receiving chemotherapy. Chemotherapy v 54: pg 447-455; Sirohi B, et al. (2007) Use of physiological doses of human growth hormone in haematological patients receiving intensive chemotherapy promotes haematopoietic recovery: a double blind randomized, placebo-controlled study. Bone Marrow Transplant. 39: 115-120; Carlo-Stella et al., 2004 Use of recombinant human growth hormone (rhGH) plus recombinant human granulocyte colony-stimulating factor (rhG-CSF) for the mobilization and collection of CD34+ cells in poor mobilizers. Blood, Vol. 103, Number 9, p. 3287-3295), and synergizing with G-CSF to mobilize CD34+ hematopoietic cells in patients who respond poorly to G-CSF alone. Thus, GH can be considered and HGF, although it has other functions as well. GH administration increased survival of 7.5 Gy irradiated mice when administered by intravenous (iv) infusion for 5 or 35 days beginning within 1 h of radiation exposure, but not when treatment was begun 6 or 12 hours following radiation exposure and continued for 5 days (Chen B J, et al. (2010) Growth hormone mitigates against lethal irradiation and enhances hematological and immune recovery in mice and nonhuman primates. PLoS ONE 5(6):el 1056.doi:10.1371/journal-.pone.0011056).

Most proteins, including HGFs, have short half-lives in humans and require daily administration for maximum effectiveness. G-CSF, GM-CSF and IL-11 typically are administered to cancer patients by daily injection for 14-21 days following chemotherapy to ameliorate neutropenia (G-CSF and GM-CSF and thrombocytopenia (IL-11). The requirement for daily administration limits the attractiveness of G-CSF, GM-CSF, IL-11 and other protein HGFs for treating subjects who have been exposed to radiation, such as ARS patients.

Angiotensin converting enzyme inhibitors (ACEIs) inhibit the biological effects of angiotensin-converting enzyme (ACE), an important component of the renin-angiotensin-aldosterone system, which regulates blood pressure. ACEIs are used to treat high blood pressure (hypertension) and congestive heart failure. ACEI causes relaxation of blood vessels and decreases blood volume, resulting in a lowering of blood pressure and decrease in oxygen demand from the heart. Representative ACEI drugs used to treat humans include lisinopril, perindopril, captopril, enalapril and ramipril.

ACEIs have been shown to improve survival of irradiated animals when administered prior to radiation or beginning 1 to 24 hours post-radiation exposure and continuing for 7 to 150 days. Treatment was started prior to when circulating levels of mature hematopoietic cells (neutrophils, platelets, red blood cells, etc.) have decreased dramatically in irradiated animals (Plett, P A, et al. (2012) Establishing a murine model of the Hematopoietic Syndrome of the Acute Radiation Syndrome. Health Physics 103: 343-355). Mature hematopoietic cells show their greatest decline in numbers between about day 3 to day 20 following radiation exposure and reach nadirs between days 10 to 15 post-irradiation (neutrophils and platelets) and day 20 post-irradiation (red blood cells). It is not known if ACEIs can increase survival when administration is begun at later times, e.g., later than 24 hours following radiation exposure, when mature hematopoietic cells have already decreased significantly in number.

Charrier et al., (Charrier S, et al. (2004) Inhibition of angiotensin I-converting enzyme induces radioprotection by preserving murine hematopoietic short-term reconstituting cells. Blood 104: 978-985) compared 48-day survival of 8.3 Gy irradiated mice treated with sc injections of water or the ACEI perindopril at 10, 30, or 90 mg/kg twice per day for 4 days starting 48 hours before the time of irradiation. Thus, mice were injected from day −2 to day 2 post-TBI with perindopril. All 3 doses of perindopril inhibited 100% of plasma ACE activity. The 10 mg/kg perindopril dose did not significantly improve 48-day survival vs water, whereas the 30 and 90 mg/kg doses did significantly improve survival versus water. Additional experiments using 8.3 cGy-irradiated mice showed that sc injections of perindopril at 30 mg/kg twice per day for 4 days starting 48 hours before irradiation improved 30-day survival versus water. No other dosing regimens of perindopril were tested in lethally irradiated mice.

Day et al (Day R M, et al. (2013) Enhanced hematopoietic protection from radiation by the combination of genistein and captopril. International Immunopharmacology 15: 348-356) reported that treating irradiated mice for 30 days with Captopril beginning one day post-irradiation improved 30-day survival from 22% (control mice) to 45%. Treating irradiated mice with Captopril beginning 1 h post-irradiation and continuing for 30 days increased 30-day survival to 55%. These data suggest that earlier treatment (starting 1 h post-irradiation) with Captopril is more effective than later treatment (starting one day after irradiation) and is thus preferred. Captopril was provided in the acidified drinking water at 0.55 g/L (110 mg/kg/day).

Davis et al (Davis T A, et al. (2010) Timing of captopril administration determines radiation protection or radiation sensitization in a murine model of total body irradiation. Experimental Hematology 38: 270-281) reported that timing of ACEI administration is critical for survival and that administering ACEI prior to irradiation leads to lower survival compared to vehicle. Davis et al. (Davis T A, et al. (2010) Timing of captopril administration determines radiation protection or radiation sensitization in a murine model of total body irradiation. Experimental Hematology 38: 270-281) treated 7.5 Gy-irradiated mice with the ACEI captopril (0.55 g/L in drinking water) from day −7 prior to total body irradiation (TBI) until Day 0, the Day of TBI. 30-day survival was lower in the Captopril-treated group (0%) versus 50% survival in the vehicle group. Treatment of 7.5 Gy-irradiated mice with Captopril from day −7 prior to TBI until Day 30 post-TBI also decreased survival to 15% compared to 50% survival in the vehicle group. By contrast, treatment of 7.5 Gy-irradiated mice with Captopril from day 1 (24 h) post-TBI until Day 7 post-TBI increased survival to 85% versus 50% for vehicle-treated mice. Treatment of 7.5 Gy-irradiated mice with Captopril from day 0 (beginning 1 hour post-TBI) until Day 30 post-TBI increased survival to 100% versus 50% for vehicle-treated mice.

Not all researchers found that ACEI treatment increased survival of irradiated animals. In contrast to the results described by Davis et al. (Davis T A, et al. (2010) Timing of captopril administration determines radiation protection or radiation sensitization in a murine model of total body irradiation. Experimental Hematology 38: 270-281; Moulder et al. (2011) RE: Davis et al., "Timing of captopril administration determines radiation protection or radiation sensitization in a murine model of total body irradiation". Experimental Hematology 39:521-524) found that treatment of 7 Gy-irradiated rats from day −7 to day 0 or from 1 h post-TBI to Day 30 post-TBI with Captopril (0.3 g/L in drinking water) had no effect on 30-day survival when compared to vehicle-treated animals. 30-day survival of rats treated with vehicle or Captopril from 1 h post-TBI to Day 30 post-TBI was the same—45%. When Captopril was administered from day −7 to Day 0, survival was lower, only 24%.

Day et al. (Day R M, et al. (2013) Enhanced hematopoietic protection from radiation by the combination of genistein and captopril. International Immunopharmacology 15: 348-356) reported that combinations of genestein (200 mg/kg, administered by sc injection 24 h prior to TBI) and the ACEI Captopril (0.55 g/L in drinking water from day 1 to day 30 post-TBI) administered post-TBI improved 30-day survival of 8.25 Gy-irradiated mice compared to either agent alone. Genestein is an isoflavone (4',5,7-trihydroxyflavone) that exhibits antioxidant activity and free radical scavenging, estrogenic effects, anti-microbial activity, anti-inflammatory activity, and protein tyrosine kinase inhibitory properties. Mice treated with vehicle had a 22% survival rate, whereas mice treated with captopril from day 1 to day 30 post-TBI had a 45% survival rate. Mice treated with captopril from day 0 (1 h post-TBI) to day 30 had a survival rate of 55%, suggesting that early treatment with captopril leads to greater survival. Mice administered genestein alone 24 h pre-TBI had a 72% survival rate, as compared to a 92% survival rate for mice treated with genestein 24 h pre-TBI and Captopril from day 1 to day 30 post-TBI. Survival increased to 95% in mice treated 24 h pre-TBI with genestein and with captopril from day 0 to day 30 post-TBI, again suggesting that early treatment with captopril leads to greater survival.

Most drugs reported to increase survival of irradiated animals when administered post-irradiation (referred to as radiation mitigators) are able to increase survival only when administered within about 24 h of radiation exposure (i.e., within about 0 to 24 h post-TBI or PBI), but not when administration is delayed to 48 h or later following radiation exposure (post-TBI or post-PBI), indicating that the timing of drug administration is a critical factor in determining whether a drug will be effective at increasing survival of irradiated subjects. For example, Farese et al. (Farese, A M, et al. (2013) Filgrastim improves survival in lethally irradiated nonhuman primates. Radiation Research 179: 89-100 (2013)) reported that daily sc administration of G-CSF beginning 24 h post-TBI and continuing for about 16 days increased survival of irradiated monkeys from 50% to 80% compared to placebo, whereas daily sc administration of G-CSF did not increase survival versus vehicle if G-CSF treatment was not started until 48 h post-TBI (Farese A M, (2014) The ability of filgrastim to mitigate mortality following LD50/60 total-body irradiation is administration time-dependent. Health Physics 106: 39-47). Since it is unlikely all subjects exposed to high radiation doses as a result of a nuclear explosion or nuclear accident can be triaged and treated within 24 h of radiation exposure, it is important to identify radiation mitigators, and optimum doses and dosing schedules of radiation mitigators, capable of increasing survival when administered 48 h or later post-TBI or post-PBI.

Thus, despite considerable effort there remains a need for identifying radiation mitigators or combinations of radiation mitigators that optimize survival following exposure of subjects to high radiation doses. There remains a need to determine if combinations of radiation mitigators are able to increase survival more than individual mitigators. There remains a need to identify optimum administration schedules to maximize the ability of a radiation mitigator or combinations of radiation mitigators to increase survival. There remains a need to identify radiation mitigators capable of increasing survival when administered 48 hours or later post-irradiation. There remains a need to determine optimum doses and dosing regimens of radiation mitigators and combinations of radiation mitigators to prevent death from both early (hematopoietic) and delayed (lung, kidney, heart, bone marrow) effects of high dose radiation exposure.

SUMMARY OF THE INVENTION

Accordingly, one embodiment of the invention relates to a method for improving survival from radiation exposure in a subject who has been exposed to radiation comprising administering to the subject an effective dose of an angiotensin-converting enzyme inhibitor (ACEI) and an effective dose of at least one hematopoietic growth factor (HGF) or protein analog thereof or combinations thereof.

In one aspect, the subject has been exposed to a myelosuppressive dose amount of radiation.

In one aspect, the ACEI is selected from the group consisting of lisinopril, perindopril, captopril, enalapril, and ramipril.

In yet another aspect, the HGF or protein analog thereof is selected from the group consisting of granulocyte colony-stimulating factor (G-CSF), granulocyte-macrophage colony-stimulating factor (GM-CSF), interleukin-11 (IL-11), interleukin-12 (IL-12), stem cell factor (SCF), erythropoietin (EPO), thromopoietin (TPO), epidermal growth factor (EGF), transforming growth factor alpha (TGF alpha), pleotropin, growth hormone (GH), insulin-like growth factor 1 (IGF-1), insulin-like growth factor 2 (IGF-2), and combinations thereof.

In still another aspect, the HGF protein analog is a long-acting HGF protein analog. In one aspect, the long-acting HGF protein analog is selected from a long-acting GM-CSF analog, a long-acting IL-11 analog, a long-acting G-CSF analog, and combinations thereof. In still another aspect, the long-acting HGF protein analog is modified with a compound selected from a polyethylene glycol (PEG), a polymer, a lipid, an HGF multi-mer, and combinations thereof. In yet another aspect, the long-acting HGF protein analog is an HGF fusion protein.

In yet another aspect, the long-acting HGF protein analog is in combination with one or more long-acting HGF protein analogs wherein the combination is selected from: a long-acting IL-11 analog and a long-acting G-GSF analog; a long-acting IL-11 analog and a long-acting GM-CSF analog; and a long-acting GM-CSF analog and a long-acting G-CSF analog; and a long-acting IL-11 analog, a long-acting GM-CSF analog, and a long-acting G-CSF analog.

In one aspect, the improved survival correlates with accelerated hematopoietic recovery in the subject.

In one aspect, the effective dose of the ACEI is administered concurrently with, prior to, or after administration of the effective dose of the at least one HGF or protein analog thereof or combinations thereof.

In yet another aspect, the effective dose of the at least one HGF or protein analog thereof or combinations thereof is a single dose of at least about 0.1 µg to about 5 mg per kg of the subject. In one aspect, the subject is administered one or more single doses of the at least one HGF or protein analog thereof or combinations thereof. In one aspect, the subject is administered one or more doses of the at least one HGF or protein analog thereof or combination thereof beginning within 24 hours following the subject's exposure to the radiation.

In still another aspect, the effective dose of the ACEI is a dose of at least about 1.3 to 50 mg/m$^2$/day. In one aspect, the subject is administered the ACEI daily beginning within 7 days following the subject's exposure to the radiation.

In yet another aspect, the effective dose of the at least one HGF or protein analog thereof is administered to the subject beginning within 24 hours following radiation exposure and the effective dose of the ACEI is administered to the subject beginning within 7 days following radiation exposure.

Another embodiment of the invention relates to a method for decreasing lung morbidity in a subject who has been exposed to a myelosuppressive dose of radiation and treated with at least one HGF or protein analog thereof or a combination thereof, comprising administering to the subject an effective dose of an ACEI following radiation exposure.

Another embodiment of the invention relates to a method for reducing damage to one or more organ systems selected from the group consisting of lung, kidney, heart, and combinations thereof, in a subject who has been exposed to a myelosuppressive dose of radiation and treated with at least one HGF or protein analog thereof or combinations thereof, comprising administering to the subject an effective dose of an ACEI following radiation exposure.

Another embodiment of the invention relates to a method for decreasing hematopoietic morbidity, renal morbidity, and/or lung morbidity due to a myelosuppressive dose of radiation exposure by administering to a subject who has been exposed to radiation an ACEI and at least one HGF or protein analog thereof or combinations thereof.

BRIEF DESCRIPTION OF THE DRAWINGS

FIG. 7A shows results for % DN1: CD25−, CD44+. FIG. 7B shows results for % DN2: CD25+, CD44+. FIG. 7 C shows results for % DN3; CD25+, CD44−. FIG. 7D shows results for % DN4: CD25−, CD44−. Irradiation results in a decreased DN3 percentage and increased DN4 percentage in the thymus, observed at 1 yr post-exposure. Mice treated with PEG-IL11-containing regimens displayed an increased percentage of DN3 cells and lower percentage of DN4 cells at 1 yr post-irradiation compared to mice receiving non-PEG IL11 regimens. N=8 mice in non-irradiated group and n=4-11 mice in each treatment group.

DETAILED DESCRIPTION OF THE INVENTION

Figure 1A:
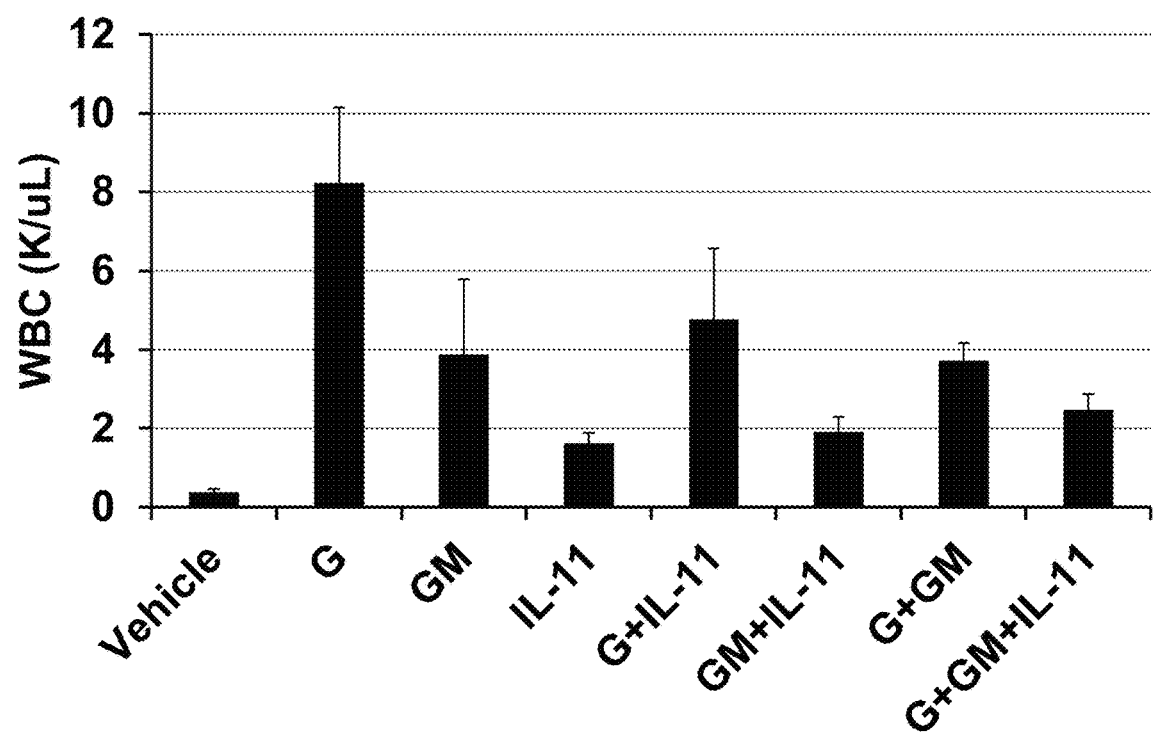
FIGS. 1A-1F show the levels of white blood cells, WBC (FIG. 1A); neutrophils, NE (FIG. 1B); lymphocytes, LY (FIG. 1C); red blood cells, RBC (FIG. 1D); hemoglobin, Hg (FIG. 1E); and platelets, PLT (FIG. 1F), on day 20 post LD95/30 irradiation in mice treated with a single subcutaneous (sc) injection of control article (vehicle), PEG-G-CSF (1 mg/kg), PEG muGM-CSF (1 mg/kg), PEG IL-11 (0.3 mg/kg), and all possible combinations of the proteins 24 hours post-irradiation.

While performing studies to optimize and improve survival of irradiated animals the inventors discovered that treating irradiated animals with certain combinations of HGFs was able to increase 30-day survival more than what was obtained by treating irradiated animals with the individual HGFs. The inventors also discovered that treating irradiated animals with an ACEI beginning within day 7 post-irradiation to day 30 post-irradiation improved 30-day survival and thus prevented death from hematopoietic complications of ARS. This was an unexpected finding because the majority of mature blood cells (e.g., neutrophils, platelets, red blood cells, lymphocytes, etc.) and hematopoietic stem and progenitor cells are believed to have been killed by radiation prior to day 7 post-irradiation, and because HGFs like G-CSF do not increase survival when administered 48 hours or later post-irradiation. The inventors also discovered that treating irradiated animals with a combination therapy comprising at least one HGF and/or a protein analog thereof and an ACEI resulted in higher 30-day survival rates than what was obtained by treating the irradiated animals with the HGF or protein analog thereof or the ACEI as solo agents, thus optimizing and improving 30-day survival and preventing death from hematopoietic complications of ARS. The inventors also discovered that treating irradiated animals with at least one HGF and/or a protein analog thereof, including G-CSF, may increase radiation-induced lung and kidney damage (morbidity) and decrease survival of irradiated animals. Since G-CSF, a prototypical HGF, is recommended for treating hematopoietic complications of acute radiation exposure it is important to identify treatments capable of preventing the additional lung and kidney damage that may be caused by treating irradiated animals with HGFs (e.g., G-CSF) or protein analogs thereof. Toward that end, the inventors discovered that treating irradiated animals with an ACEI following radiation exposure reduced or prevented lung and kidney damage (morbidity) caused by radiation and the increased lung and kidney damage (morbidity) caused by treating irradiated animals with HGFs (e.g., G-CSF), thus increasing survival of irradiated animals treated with HGFs (e.g., G-CSF).

The present invention is directed toward methods to improve survival and/or accelerate hematopoietic recovery in a subject that has been or will be exposed to radiation. The invention includes administering an effective dose of an HGF and/or a protein analog thereof and/or combinations of HGFs, and/or combinations of HGF protein analogs and/or combinations of HGFs and HGF protein analogs thereof to the subject either following the subject's exposure to radiation or prior to the subject's exposure to radiation. The HFG analogs can be long-acting analogs or non-long-acting analogs. The method further includes administering an effective dose of ACEI along with the HGF analogs(s).

The present invention also is directed toward methods to accelerate hematopoietic recovery, reduce damage to organs such as the hematopoietic system, lung, kidney and heart, and improve survival in a subject that has been exposed to radiation. The invention includes administering an effective dose of an ACEI to the subject following the subject's exposure to radiation.

The present invention also is directed toward methods to accelerate hematopoietic recovery, reduce damage to organs such as the hematopoietic system, lung, kidney and heart, and improve survival in a subject that has been or will be exposed to radiation. The invention includes administering an effective dose of an HGF or protein analog thereof or a combination of HGFs or protein analogs thereof to the subject either following the subject's exposure to radiation or prior to the subject's exposure to radiation, and also administering to the subject an effective dose of an ACEI following the subject's exposure to radiation.

The present invention is also directed towards methods for decreasing lung morbidity in a subject that has been exposed to a myelosuppressive dose of radiation and treated with at least one HGF or protein analog thereof. The method includes administering an effective dose of an ACEI following radiation exposure.

The present invention is also directed towards methods for reducing damage to one or more organ systems, including lung, kidney, heart and combinations thereof, in a subject who has been exposed to a myelosuppressive dose of radiation and treated with at least one HGF or protein analog thereof. The method includes administering to the subject an effective dose of an ACEI following radiation exposure.

The present invention is also directed towards methods of decreasing hematopoietic morbidity, renal morbidity, and/or lung morbidity due to a myelosuppressive dose of radiation exposure by administering to a subject who has been exposed to radiation an ACEI and at least one HGF or protein analog thereof.

Accelerated hematopoietic recovery generally refers to accelerated recovery of a subject's blood cell count or level of various blood cell types including but not limited to white blood cell levels, neutrophil levels, lymphocyte levels, monocyte levels, macrophage levels, eosinophil levels, basophil levels, dendritic cell levels, T lymphocyte levels, B lymphocyte levels, red blood cell levels, platelet levels and combinations thereof, after the subject has been exposed to radiation compared to levels of the same blood cell type from subjects who have been exposed to radiation and have not been administered at least one HGF or protein analog thereof, or an ACEI and at least one HGF or protein analog thereof within about 0 to 60 days following radiation exposure (irradiated control subjects). Accelerated hematopoietic recovery can also refer to accelerated recovery of a subject's hemoglobin and hematocrit levels compared to these levels from a control. Hemoglobin is a major protein component of red blood cells and changes in hemoglobin levels typically correlate with changes in red blood cell levels. Hematocrit or packed cell volume is a measure of the blood volume that is comprised of red blood cells, thus changes in hematocrit levels typically correlate with changes in a subject's red blood cell levels. Hematopoietic recovery can also refer to increased numbers of hematopoietic stem and progenitor cells compared to these levels in controls.

Hematopoietic recovery can be complete, i.e., to levels comparable to levels from non-exposed subjects (subjects not exposed to radiation, i.e., non-irradiated controls), or incomplete, i.e., to levels greater than the blood cell nadir but below levels seen in non-exposed (control) subjects. Accelerated hematopoietic recovery generally refers to hematopoietic recovery that occurs sooner compared to subjects that have been exposed to radiation but have not been administered an effective dose of a hematopoietic factor protein analog of the present invention. In one embodiment of the invention, the subject's platelet level recovers to levels comparable to levels from a non-exposed subject or a subject that has been exposed to radiation but has not been administered an effective dose of a hematopoietic factor protein analog of the present invention. In another embodiment, a subject's red blood cell level recovers to levels comparable to levels from a non-exposed subject or a subject that has been exposed to radiation but has not been administered an effective dose of a hematopoietic factor protein analog of the present invention. In still another embodiment, the subject's platelet level and red blood cell level recovery to levels comparable to levels from a non-exposed subject or a subject that has been exposed to radiation but has not been administered an effective dose of a hematopoietic factor protein analog of the present invention. In another embodiment of the invention the subject's white blood cell level recovers to levels comparable to levels from a non-exposed subject or a subject that has been exposed to radiation but has not been administered an effective dose of a hematopoietic factor protein analog of the present invention. In another embodiment of the invention the subject's neutrophil level recovers to levels comparable to levels from a non-exposed subject or a subject that has been exposed to radiation but has not been administered an effective dose of a hematopoietic factor protein analog of the present invention. In another embodiment of the invention the subject's lymphocyte level recovers to levels comparable to levels from a non-exposed subject or a subject that has been exposed to radiation but has not been administered an effective dose of a hematopoietic factor protein analog of the present invention. In still another embodiment, the subject's neutrophil level, platelet level and red blood cell level recover to levels comparable to levels from a non-exposed subject or a subject that has been exposed to radiation but has not been administered an effective dose of a hematopoietic factor protein analog of the present invention. In still another embodiment, the subject's neutrophil level, lymphocyte level, platelet level and red blood cell level recover to levels comparable to levels from a non-exposed subject or a subject that has been exposed to radiation but has not been administered an effective dose of a hematopoietic factor protein analog of the present invention. In still another embodiment, the subject's neutrophil level, white blood cell level, lymphocyte level, platelet level and red blood cell level recover to levels comparable to levels from a non-exposed subject or a subject that has been exposed to radiation but has not been administered an effective dose of a hematopoietic factor protein analog of the present invention. In another aspect of the invention, hematopoietic recovery results in accelerated recovery (increased numbers compared to controls: a non-exposed subject or a subject that has been exposed to radiation but has not been administered an effective dose of a hematopoietic factor protein analog of the present invention) of a subject's neutrophil levels and platelet levels, or neutrophil levels and red blood cell levels, or platelet levels and red blood cell levels, or neutrophil levels, platelet levels and red blood cell levels. In another aspect of the invention, hematopoietic recovery results in increased numbers of hematopoietic stem and progenitor cells in the irradiated subject.

Methods of the invention may be used to accelerate hematopoietic recovery in a variety of subjects that have been exposed to radiation. In one aspect, the subject has been exposed to a myelosuppressive dose amount of radiation. In still another aspect, the subject has been acutely exposed to a myelosuppressive dose amount of radiation. In still another aspect, the subject has been exposed to a fractionated myelosuppressive dose amount of radiation. Such a fractionated dose amount can be received by the subject over days and/or weeks, such as during cancer treatment, and result in a cumulative myelosuppressive radiation dose amount. A myelosuppressive dose amount generally is an amount of radiation greater than 2 Gray. In one embodiment, the subject has been diagnosed as having ARS. In another embodiment, the subject has been diagnosed as having complications of therapeutic radiation treatment. In another embodiment, the subject includes all animals and preferably, any member of the Vertebrate class, Mammalia, including, without limitation, primates, rodents, livestock and domestic pets. Livestock include mammals to be consumed or that produce useful products (e.g., sheep for wool production). Preferred mammals include humans, dogs, cats, mice, rats, sheep, cattle, horses and pigs, with humans being particularly preferred.

In one embodiment of the invention, the subject has been exposed to high and/or lethal radiation doses that typically results in the subject developing a set of well characterized radiation dose-dependent and time-dependent organ malfunctions including but not limited to bone marrow aplasia, severe neutropenia, anemia, thrombocytopenia, and lymphopenia, within 2-3 weeks of radiation exposure. Subjects can be exposed to high, but non-lethal doses (i.e. a high therapeutic dose) for example in a hospital setting, such as for treating diseases with therapeutic radiation (e.g., cancer). Therapeutic radiation treatment is radiation treatment given to a patient to affect a therapeutic outcome such as killing cancer cells or slowing the growth of cancer cells. In one aspect of the invention in which a subject has been intentionally exposed to radiation such as for cancer therapy, the subject is treated with a combination of one or more HGFs and/or protein analogs thereof and an ACEI. The HGF (including the non-long-acting and the long-acting HGF analogs disclosed herein) can be administered prior to or after the subject has been exposed to radiation. If the HGF or protein analog thereof is administered prior to radiation exposure, preferably, an effective dose of the HGF or protein analog thereof is administered beginning within about 7 days prior to radiation exposure, more preferably within about 48 h to 72 hours prior to radiation exposure, more preferably within about 24 h prior to radiation exposure, and even more preferably within about 1 h prior to radiation exposure. If the HGF or protein analog thereof is administered after radiation exposure, preferably, an effective dose of the HGF or protein analog thereof is administered within about 7 days of radiation exposure, more preferably within about 72 h of radiation exposure, more preferably within about 48 hours of radiation exposure, more preferably within about 24 h of radiation exposure, and even more preferably within about 1 h of radiation exposure. Preferably the HGF comprises an HGF selected from the group consisting of G-CSF, GM-CSF, and IL-11, and analogs of G-CSF, GM-CSF and IL-11 proteins, including long-acting analogs of these proteins. More preferably the HGF comprises a combination comprising a G-CSF analog plus an IL-11 analog, or a GM-CSF analog plus an IL-11 analog, or a G-CSF analog plus a GM-CSF analog, or a G-CSF analog plus a GM-CSF analog plus an IL-11 analog. Preferably, treatment with an effective dose of the ACEI is started beginning within about 35 days following radiation exposure, more preferably within about 30 days following radiation exposure, more preferably within about 10 days following radiation exposure, more preferably within about 7 days following radiation exposure, more preferably within about 24 h post-irradiation to about day 7 following radiation exposure, more preferably within about 24 h following radiation exposure, and even more preferably within about 1 h following radiation exposure. Treatment with the ACEI should be continued for 30 days, 60 days, 90 days, 4 months, 5 months, 6 months, 7 months 8, months, 9 months, 10 months, 11 months or 12 months to prevent death from hematopoietic complications of acute radiation exposure. Treatment with the ACEI should be continued for up to 90 days, 4 months, 5 months, 6 months, 7 months 8, months, 9 months, 10 months, 11 months or 12 months to prevent death from late effects of radiation exposure, including lung, kidney and heart complications of acute radiation exposure such as lung pneumonitis, lung fibrosis and kidney nephropathy. Patients should be re-evaluated by a physician following completion of treatment with the ACEI to determine if continued treatment with the ACEI would be beneficial for the patient. In one preferred embodiment of the invention the subject exposed to radiation is treated with a combination comprising a long-acting G-CSF analog, a long-acting GM-CSF analog and a long-acting IL-11 analog within about 24 h prior to radiation exposure, and with an ACEI beginning about day 7 post-irradiation and continuing for about 150 days, about 160 days, about 170 days, about 180, days, about 190 days, about 200 days, about 210 days, about 220 days, about 230 days, about 240 days, about 250 days, about 260 days, about 270 days, about 280 days, about 290 days, about 300 days, about 310 day, about 320 days, about 330 days, about 340 days, about 350 days, about 360 days, about 365 days or about 370 days. Optionally, the subject exposed to irradiation can be treated a second time with the combination comprising the long-acting G-CSF analog, the long-acting GM-CSF analog and the long-acting IL-11 analog on or about day 8 post-irradiation. Optionally, the subject exposed to irradiation can be treated for a third time with the combination comprising the long-acting G-CSF analog, the long-acting GM-CSF analog and the long-acting TL-11 analog on about day 15 post-irradiation. Optionally, treatment with the ACEI can begin within about 1 h post-irradiation, within about 24 h post-irradiation, or within about 24 h post-irradiation to about day 7 post-irradiation.

Subjects can be exposed to high (non-therapeutic radiation doses) and/or lethal radiation doses as a result of detonation of a nuclear device, or leakage of radioactive substances, e.g., from a nuclear power plant.

An ACEI useful for practicing the invention can be any drug capable of inhibiting the activity of ACE. In one aspect, the ACEI can be a small molecule, an organic compound, an antibody, an antibody fragment, an anti-sense nucleotide, an aptamer, or a protein or peptide that has been selected or engineered to bind and neutralize ACE. Preferably the ACEI is selected from the group consisting of lisinopril, perindopril, captopril, enalapril and ramipril. More preferably, the ACEI is lisinopril.

Many of the hematopoietic factor protein analogs of the present invention are members of the growth hormone supergene family of proteins and include but are not limited to G-CSF analogs, GM-CSF analogs, GH analogs, IL-11 analogs and EPO analogs. Long-acting hematopoietic-factor protein analogs include but are not limited to cysteine muteins, polymer modified analogs and fusion protein analogs of the growth hormone supergene family of proteins. Long-acting GCSF, long-acting GM-CSF, long-acting interleukin-11, long acting GH, long acting EPO protein analogs as well as other Growth Hormone supergene family protein analogs have been created by using various fusion protein and polymer modification technologies, including site-specific PEGylation technology. G-CSF, GM-CSF, IL-11 and GH cysteine analogs are described in U.S. Pat. Nos. 6,608,183, 6,753,165, 7,306,931, 7,309,781, 7,232,885, 7,306,931, 7,214,779, 7,148,333, 7,495,087, 7,253,267, and 8,133,480, all of which are incorporated herein by reference. Site-specific PEGylation permits the rational design of homogeneous PEG-protein conjugates with defined structures and preserved biological activities. Site-specific PEGylation is accomplished by covalent attachment of cysteine-specific PEGs (maleimide- or vinylsulfone-PEGs) to engineered cysteine residues in proteins. At near neutral pH, these PEG reagents selectively attach to the thiol groups of "free" cysteine residues, i.e., cysteine residues not involved in disulfide bonds. The resulting conjugates are hydrolytically stable. Site-specific PEGylation overcomes the problems of product heterogeneity and loss of bioactivity that often occurs when proteins are modified using amine-reactive PEGylation technology and reagents. For example, in vitro biological activities of the site-specific PEGylated G-CSF cysteine analog, G-CSF (A141C; alanine at position 141 changed to cysteine of SEQ ID NO:1; long-acting), are comparable to that of G-CSF, and 50-fold better than that of G-CSF proteins modified by conventional amine PEGylation technologies (U.S. Pat. No. 7,306,931). The PEG-G-CSF (A141C) protein has an 8- to 10-fold longer half-life than G-CSF in rodents. PEG-G-CSF (A141C) also stimulated greater and longer lasting increases in neutrophils and white blood cells than unmodified G-CSF in normal rats. PEG-G-CSF (A141C) accelerated recovery from neutropenia following a single injection in chemotherapy (cyclophosphamide)-treated rats whereas unmodified G-CSF was ineffective as a single-injection.

G-CSF is a pluripotent cytokine that stimulates the proliferation, differentiation and function of granulocytes. The human protein is synthesized as a preprotein of 204 or 207 amino acids that is cleaved to yield mature proteins of 174 or 177 amino acids. The larger form has lower specific activity than the smaller form. The protein contains 5 cysteine residues, 4 of which form two disulfide bonds. The fifth cysteine residue, cysteine-17, is unpaired or "free". C17 causes G-CSF to be unstable and aggregate at physiological pH and at 37° C. Preferred embodiments of the present invention are G-CSF analogs and PEG-G-CSF analogs that do not contain C17, i.e., the preferred G-CSF analogs contain a non-cysteine amino acid, preferable alanine or serine, substituted for C17. G-CSF analogs containing a non-cysteine amino acid at position 17 are more stable than G-CSF at physiological pH and at 37° C. However, the present invention encompasses G-CSF analogs and PEG-G-CSF analogs that do contain C17 and G-CSF analogs and PEG-G-CSF analogs that contain a non-cysteine amino acid, preferably alanine or serine, substituted for C17. In one aspect, the long-acting G-CSF analog is a recombinant human G-CSF protein analog comprising one or more cysteine substitutions or additions. In another aspect, the recombinant G-CSF protein analog comprises a cysteine residue substituted for A141 of human G-CSF (SEQ ID NO:1) and a non-cysteine amino acid residue substituted for C17 of human G-CSF (SEQ ID NO:1). In one embodiment, the long-acting G-CSF protein analog contains A141C and C17S amino acid substitutions in SEQ ID NO:1 and is further modified with a 40 kDa-PEG (this analog is referred to as "BBT-0015"). Other long-acting G-CSF analogs useful for practicing the invention, such as peg-filgrastim (met-G-CSF, with a 20 kDa-PEG attached to the N-terminus of the protein), MAXY-G34, an amine-PEGylated G-CSF, and G-CSF/immunoglobulin fusion proteins are described in Plett et al. (Plett, P. A., Chua, H. L., Sampson, C. H., Katz, B. P., Fam, C. M., Anderson, L. J., Cox, G. N., and Orschell, C. M. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20), Chua et al. (Chua H L, Plett P A, Sampson C H, et al. (2014) Survival efficacy of the PEGylated G-CSFs Maxy-G34 and neulasta in a mouse model of lethal H-ARS, and residual bone marrow damage in survivors. Health Physics 106: 21-38), and Cox et al., (Cox, G. N., Smith, D. J., Carlson, S. J., Bendele, A. M., Chlipala, E. A. and Doherty, D. H. (2004) Enhanced circulating half-life and hematopoietic properties of a human granulocyte colony-stimulating factor (G-CSF)-immunoglobulin fusion protein. Exp. Hematol. 32, 441-449; Cox, G. N. (2014) Methods of treatment using cysteine variants of interleukin-11. U.S. Pat. No. 8,748,392). Other long-acting G-CSF analogs useful for practicing the invention include, but are not limited to G-CSF analogs in which one or more lysine residues are modified with PEG. Additional sites for the introduction of cysteine residues in human G-CSF (SEQ ID NO:1) are: T1, P2, L3, G4, P5, A6, S7, S8, L9, P10, Q11, S12, T38, K40, S53, G55, W58, A59, P60, S62, S63, P65, S66, Q67, A68, Q70, A72, Q90, A91, E93, G94, S96, E98, G100, G125, M126, A127, A129, Q131, T133, Q134, G135, A136, A139, A141, S142, A143, Q145, Q173 and P174. Most preferred cysteine substitution positions are: T1, P2, L3, A6, S7, W58, A68, E93, A129, Q131, T133, Q134, A136, A139, A141 and Q173. Cysteine residues also can be added preceding the first amino acid of the mature protein, i.e., preceding T1, or following the last amino acid in the mature protein, i.e., following P174.

GM-CSF stimulates the proliferation and differentiation of various hematopoietic cells, including neutrophil, monocyte, eosinophil, erythroid, and megakaryocyte cell lineages. The amino acid sequence of human GM-CSF is given in SEQ ID NO: 2. GM-CSF is produced as a 144 amino acid preprotein that is cleaved to yield a mature 127 amino acid protein. The mature protein has two sites for N-linked glycosylation. One site is located at the C-terminal end of Helix A; the second site is in the A-B loop.

In another embodiment of the method of the present invention, a recombinant long-acting human GM-CSF protein analog comprises an A3C amino acid substitution in SEQ ID NO:2. In another aspect the-human long acting GM-CSF comprises an A3C amino acid substitution in SEQ ID NO:2 and is further modified—with a 40 kDa-PEG (this analog is referred to as "BBT-007") (Doherty, D. H., Rosendahl, M. S., Smith, D. J., Hughes, J. M., Chlipala, E. A. and Cox, G. N. (2005) Site-Specific PEGylation of Engineered Cysteine Analogues of Recombinant Human Granulocyte-Macrophage Colony-Stimulating Factor. Bioconjugate Chemistry 16: 1291-1298). Other long-acting GM-CSF analogs useful for practicing the invention include, but are not limited to GM-CSF proteins in which the N-terminal amino acid has been modified with PEG, and GM-CSF analogs in which one or more lysine residues has been modified with PEG. In still another aspect, the long-acting GM-CSF protein analog is a human GM-CSF protein analog comprising one or more-cysteine substitutions or additions. Additional sites for the introduction of cysteine residues in-human GM-CSF (SEQ ID NO:2) are: A1, P2, A3, R4, S5, P6, S7, P8, S9, T10, Q11, N27, L28, S29, R30, D31, T32, A33, A34, E35, N37, E38, T39, E41, S44, E45, D48, Q50, E51, T53, Q64, G65, R67, G68, S69, L70, T71, K72, K74, G75, T91, E93, T94, S95, A97, T98, T102, 1117, D120, E123, V125, Q126 and E127. Most preferred cysteine substitution positions are: A1, A3, S5, S7, N27, T32, A33, E51, R67, S69, E93, T94, T98, Q99, T102, E123, V125, Q126, and E127. Cysteine-residues also can be added preceding the first amino acid of the mature protein, i.e., preceding A1, or following the final amino acid of the mature protein, i.e., following E127. Human and rodent GM-CSF proteins perform similar functions in their respective-species. Human and rodent GM-CSF proteins share 50-60% amino acid identity, but there is no-cross species cross-reactivity in terms of biological activity or receptor binding. It is possible to-use the significant amino acid identity between human and rodent GM-CSF proteins to construct-murine GM-CSF hematopoietic factor protein analogs that are analogues of human GM-CSF-hematopoietic factor protein analogs. The murine GM-CSF analogs can be expressed, purified- and PEGylated using procedures similar to those described for human GM-CSF and in PCT Application No. PCT/US01/16088 (WO 01/87925).

In still another embodiment, the GM-CSF protein analog is a murine GM-CSF protein analog (SEQ ID NO:6) comprising one or more cysteine substitutions or additions. In another embodiment, the murine GM-CSF protein analog comprises a T3C amino acid substitution in SEQ ID NO:6. In-still another aspect, the murine GM-CSF protein analog comprising a T3C substitution is further modified with a 40 kDa-PEG (this analog is referred to as "murine BBT-007"). Methods for-making the murine GM-CSF protein analogs are described in U.S. Pat. No. 7,994,124.

IL-11 is a pleiotropic cytokine that stimulates hematopoiesis, lymphopoeisis and acute phase responses. IL-11 shares many biological effects with TL-6. The amino acid sequence of human IL-11 is given in SEQ ID NO: 3. SEQ ID NO:7 is SEQ ID NO:3 without the amino-terminal 21 amino acid signal sequence. IL-11 is synthesized as a precursor protein of 199 amino acids that is cleaved to yield a mature protein of 178 amino acids. Cleavage results in removal of the amino-terminal 21 amino acid signal sequence required for secretion. There are no N-linked-glycosylation sites in the protein.

In still another embodiment of the method of the present invention, the long acting IL-11 analog is a recombinant human IL-11 protein analog comprising one or more cysteine substitutions or additions. In another aspect, the recombinant IL-11 protein analog comprises a cysteine residue added following the carboxy-terminal amino acid of IL-11 (having SEQ ID NO:7 or SEQ ID NO:3). In another aspect, the recombinant IL-11 protein analog comprises a cysteine residue added following the carboxy-terminal amino acid of IL-11 (having SEQ ID NO:7 or SEQ ID NO:3) and a deletion of the P1 amino acid of IL-11 (SEQ ID NO:7). In still another aspect, the human IL-11 protein analog comprising a cysteine residue added following the carboxy-terminal amino acid and deletion of the P1 amino acid is further modified with PEG. Another long-acting IL-11 analog (an amine-PEGylated IL-11 protein) useful for practicing the invention is described in Tagaki et al., (Takagi A., Yamashita M., Yoshioka T. Et al. (2007) Enhanced pharmacological activity of recombinant interleukin-11 (rhIL-11) by chemical modification with polyethylene glycol. J Controlled Release 119: 271-278). Other long-acting IL-11 analogs useful for practicing the invention include, but are not limited to IL-11 analogs in which the N-terminal amino acid is modified with PEG, and IL-11 analogs in which one or more lysine residues is modified with PEG. In another embodiment, the long acting human IL-11 protein analog comprises a cysteine residue added following the carboxy-terminal amino acid of the mature human IL-11 protein and is further modified with a 40 kDa-PEG (referred to as BBT-059 or IL-11 (*200 C)). The long-acting IL-11 analogs of the present invention may or may not contain the amino-terminal proline-1 amino acid of native mature human IL-11 (IL-11 in which the 21 amino acid signal sequence has been removed-SEQ ID NO:7) (proline-1 of SEQ ID NO:7 is the same as proline-22 of SEQ ID NO:3). The long-acting IL-11 analogs of the present invention may have glycine-23 as the amino-terminal amino acid. In still another embodiment, the long acting human IL-11 protein analog comprises one or more cysteine substitutions or additions. Additional sites for the introduction of cysteine residues in human IL-11 (based on SEQ ID NO:3) are: P22, G23, P24, P25, P26, G27, P28, P29, R30, V31, S32, P33, D34, P35, R36, A37, E38, L39, R54, Q55, L56, A57, A58, Q59, L60, R61, D62, K63, F64, P65, A66, D67, G68, D69, H70, 30 N71, L72, D73, S74, L75, P76, T77, L78, A79, M80, S81, A82, G83, A84, L85, G86, A87, L88, Q89, L90, P91, G92, V93, L94, WHO, L111, R112, E125, L126, G127, S145, R146, L147, A148, L149, P150, Q151, P152, P153, P154, D155, P156, P157, A158, P159, P160, L161, A162, P163, P164, S165, 5166, A167, W168, G169, G170, 1171, R172, A173, A174, H175, L194, L195, K196, T197, R198, and L199. Most preferred cysteine substitution positions are: P22, G23, P24, P25, G27, E38, L39, D69, L72, 574, T77, A114, 5117, E123, A148, Q151, A158, A162, and 5165. Cysteine residues also can be added preceding the first amino acid of the mature protein, i.e., preceding P22, or following the final amino acid of the mature protein, i.e., following L199.

The sequence of human GH is well known (SEQ ID NO:4). The primary sequence of GH is highly conserved among animal species, consistent with the protein's broad species cross-reactivity. In another embodiment of the method of the present invention, a recombinant long-acting human GH protein analog comprises a P133C amino acid substitution. In yet another embodiment, the long acting human GH protein analog comprises a P133C amino acid substitution and is further modified with a 40 kDa-PEG. In another embodiment of the method of the present invention, a recombinant long-acting human GH protein analog comprises a T3C amino acid substitution. In still another embodiment, the long-acting human GH protein analog comprises a T3C amino acid substitution and is further modified with a 40 kDa-PEG. In still another embodiment, the long acting human GH protein analog comprises one or more cysteine substitutions or additions Additional sites for the introduction of cysteine residues in human GH (SEQ ID NO:4) are: F1, T3, P5, E33, 30 A34, Y35, K38, E39, Q40, S43, Q46, N47, P48, Q49, T50, S51, S55, T60, A98, N99, S100, G104, A105, S106, E129, D130, G131, S132, P133, T135, G136, Q137, K140, Q141, T142, S144, K145, D147, T148, N149, S150, H151, N152, D153, S184, E186, G187, S188, and G190. Most preferred cysteine substitution positions are: P2C, T3C, P5C, K38C, Q40C, S55C, S57, N99C, L101C, V102C, Y103C, S132C, P133C, R134C, Q137C, K140C, Q141, Y143, S144C, D147C, T148C, N149, E186C and G187C. Cysteine residues also can be added preceding the N-terminal amino acid of the mature protein, i.e., preceding the F1 amino acid, or following the last amino acid in the mature protein, i.e., following F191.

EPO is the hormone primarily responsible for stimulating erythropoiesis or red blood cell formation. EPO acts on immature red blood cell precursors to stimulate their further proliferation and differentiation into mature red blood cells. A commercial pharmaceutical version is available from Amgen, Inc. Human EPO is a 35-39 kDa glycoprotein secreted by the adult kidney. The mature human protein contains 166 amino acids and is heavily glycosylated. The sequence of human EPO is given in SEQ ID NO: 5. The primary sequence of EPO is highly conserved among species (greater than 80% identity). Sugar groups account for greater than 40% of the protein's mass.

In one embodiment of the method of the present invention a dose of long acting EPO protein analog is administered to the subject. Sites for cysteine substitutions are the O-linked glycosylation site (serine-126) and the amino acids comprising the three N-linked glycosylation sites (N24, 125, T26, N38, I39, T40, N83, S84, S85). Other preferred sites for cysteine substitutions in these regions are: A1, P2, P3, R4, D8, S9, T27, G28, A30, E31, H32, S34, N36, D43, T44, K45, N47, A50, K52, E55, G57, Q58, G77, Q78, A79, Q86, W88, E89, T107, R110, A111, G113, A114, Q115, K116, E117, A118, S120, P121, P122, D123, A124, A125, A127, 30 A128, T132, K154, T157, G158, E159, A160, T163, G164, D165 and R166. Cysteine residues also can be introduced proximal to the first amino acid of the mature protein, i.e., proximal to A1, or distal to the final amino acid in the mature protein, i.e., distal to D165 or R166. Other variants in which cys-29 or cys-33 have been replaced with other amino acids, preferably serine or alanine, also are provided.

In one aspect, the HGF is selected from a G-CSF analog, a GM-CSF analog, an IL-11 analog and combinations of two or all three of these HGF analogs. Other HGFs that can be used in the invention and combined with ACEI to improve survival and/or prevent death from hematopoietic complications of acute, high dose (myelosuppressive) radiation exposure include interleukin-2 (IL-2), IL-3, IL-4. IL-6, IL-12, IL-13, IL-15, EPO, TPO, SCF, Flt-3 ligand, and pleotropin. Other proteins that are capable of stimulating proliferation and/or differentiation of one or more hematopoietic cell types and that can be used in the invention and combined with an ACEI to improve survival and/or prevent death from hematopoietic complications of acute radiation exposure include EGF, TGF alpha, GH, insulin-like growth factor-1 (IGF-1), and IGF-2. In one aspect, the HGF is a long-acting HGF, that is, the HGF has been engineered or modified to last longer in a subject than the unmodified or non-engineered HGF. An HGF useful for practicing the invention includes any drug, molecule, protein, peptide, or oligonucleotide (e.g., anti-sense nucleotide or aptamer) capable of stimulating proliferation and/or differentiation of one or more hematopoietic cell types, including neutrophils, monocytes, macrophages, white blood cells, red blood cells, platelets, lymphocytes, monocytes, hematopoietic stem cells, and hematopoietic progenitor cells. Preferably, treatment with the HGF accelerates hematopoietic recovery in the irradiated subject. In another aspect of the invention, hematopoietic recovery results in accelerated recovery (increased numbers compared to controls-non-exposed subjects or subjects exposed but not treated with an HGF or HGF protein analog thereof) of the subject's neutrophil levels. In another aspect of the invention, hematopoietic recovery results in accelerated recovery (increased numbers compared to controls-non-exposed subjects or subjects exposed but not treated with an HGF or HGF protein analog thereof) of the subject's platelet levels. In another aspect of the invention, hematopoietic recovery results in accelerated recovery (increased numbers compared to controls—non-exposed subjects or subjects exposed but not treated with an HGF or HGF protein analog thereof) of the subject's red blood cell levels In one embodiment, long-acting HGF protein analogs are HGF fusion proteins comprising an HGF or HGF protein analog fused to a second protein or peptide such as an immunoglobulin, an immunoglobulin domain(s) (Cox, G. N., et al. (2004) Enhanced circulating half-life and hematopoietic properties of a human granulocyte colony-stimulating factor (G-CSF)-immunoglobulin fusion protein. Exp. Hematol. 32, 441-449), albumin, transferrin, transferrin receptors, or elastin and elastin-like Proteins, XTEN amino acid sequences (Cleland J L, et al. (2012) A novel, long-acting human growth hormone fusion protein (VRS-317): enhanced in vivo potency and half-life. Journal of Pharmaceutical Sciences 101: 2744-2754), one or more CTP sequences (Fares F A, et al. (1992) Design of a long-acting follitropin agonist by fusing the C-terminal sequence of the chorionic gonadotropin beta subunit to the follitropin beta subunit. Proc Natl Acad Sci USA 89: 4304-4308), or any protein or peptide that, when fused to the HGF, causes the HGF fusion protein to have a longer in vivo half-life than the HGF. Fusion protein analogs can be long-acting fusion proteins comprising long-acting GCSF, long-acting GM-CSF, long-acting IL-11 and long-acting GH fused to immunoglobulin domains (described in U.S. Pat. No. 7,754,855). In another embodiment, long-acting HGF protein analogs are fused to any second protein that confers a longer half-life to the HGF fusion protein compared to the non-fused HGF.

The HGF protein can be fused to the amino-terminus of the second protein, to the carboxy-terminus of the second protein, or in between two amino acids of the second protein. The HGF may be fused to the second protein via an intervening peptide linker or it may be fused to the second protein directly, i.e., without an intervening peptide linker. Examples of joining two proteins as direct fusion proteins and as fusion proteins with peptide linkers are provided in U.S. Pat. No. 7,754,855. In still other embodiments of the present invention, the fusion protein used for modifying the HGF protein can be any fusion protein that confers a half-life that is longer than the half-life of the non-fusion HGF protein-modified protein in animals.

In still other embodiments of the present invention, a polymer or compound can be used for modifying the HGF. The polymer or compound can be any polymer or compound that confers a half-life that is longer than the half-life of the non-polymer-modified HGF protein (non-compound-modified HGF protein) in animals. In still other embodiments of the present invention, the polymer or compound used for modifying the protein can be PEG, a lipid or starch. The PEG can be any PEG that confers a half-life that is longer than the half-life of the unPEGylated protein in animals.

In still other embodiments of the present invention, polymer used for modifying the HGF protein can be any polymer that confers a half-life that is longer than the half-life of the nonpolymer-modified HGF protein in animals.

In another aspect of the invention, the long acting HGF analog is an HGF that has been engineered to add additional glycosylation sites to the protein, for example by changing the HGF's amino acid sequence. Preferably the added glycosylation site is an O-linked glycosylation site or an N-linked glycosylation site. An N-linked glycosylation site has the three amino acid sequence Asparagine-X-Serine or threonine, when X can be any amino acid. An O-linked glycosylation site can be created by substituting a serine or threonine residue for a non-serine or threonine amino acid in the protein. In another aspect of the invention, the long acting HGF analog is an HGF that has been engineered so that it can be modified with compounds that allow the HGF to non-covalently bind proteins such as albumin that have long in vivo half-lives. Examples of methods that allow proteins to be modified so that they are able to non-covalently bind albumin are described in U.S. Pat. No. 8,841,249 and WO 2005/027978.

Peptides that bind and activate cellular receptors for G-CSF, GM-CSF, GH, IL-11, TPO and other HGFs have been described in the literature. The methods described herein also may be applied to using these peptides and long-acting analogs of these peptides for accelerating hematopoietic recovery and improving survival in subjects who have been exposed to radiation. Peptide mimetics that bind and activate cellular receptors for G-CSF, GM-CSF, GH, IL-11, TPO and other HGFs have been described in the literature. The methods described herein also may be applied to using these peptide mimetics for accelerating hematopoietic recovery and improving survival in subjects who have been exposed to radiation.

In embodiments of the present invention, the at least one HGF and/or protein analogs thereof disclosed herein are administered to the subject in a dose that provides therapeutic benefits to the subject. As also disclosed herein, the subject can be further administered in combination with the at least one HGF and/or protein analogs thereof disclosed herein an ACEI, further increasing the therapeutic benefit (such as increasing survival as compared to the at least one HGF and/or protein analogs thereof without the ACEI). Therapeutic benefits include but are not limited to accelerated hematopoietic recovery and/or survival benefits (improved survival) to subjects. Survival benefits include an increase in life expectancy of a subject that has been exposed to radiation. According to the present invention, an effective administration protocol (i.e., administering the at least one HGF and/or protein analog thereof in an effective manner) comprises suitable dose parameters and modes of administration that result in the desired effect in the subject (e.g., increased survival or acceleration of hematopoietic recovery). In accordance with the present invention, a suitable single dose size is a dose that results in the desired therapeutic effect in the subject, when administered one or more times over a suitable time period. Doses can vary and one of skill in the art can readily determine appropriate single dose sizes for a given subject based on the size of a patient and the route of administration. In one aspect of the invention, a suitable single dose of the at least one HGF or protein analog thereof as disclosed herein or combinations of the HGF and/or the protein analogs thereof of the present invention is an amount that, when administered by any route of administration, provides a therapeutic effect in the subject as described above, as compared to a patient which has not been administered the at least one HGF and/or protein analog thereof disclosed herein or combination of the HGF and/or the protein analog thereof of the present invention (i.e., a control), as compared to the subject prior to administration of the HGF or protein analogs thereof disclosed herein.

In one aspect of the invention an appropriate single dose of the at least one hematopoietic factor protein or analog thereof disclosed herein is at least about 0.1 µg per kg of the subject to which the long acting hematopoietic factor protein analog is administered, and in other aspects, at least about 0.5 µg/kg, at least about 1.0 µg/kg, at least about 1.5 µg/kg, at least about 2.0 µg/kg, at least about 2.5 µg/kg, at least about 3.0 µg/kg, at least about 3.5 µg/kg, at least about 4.0 µg/kg, at least about 4.5 µg/kg, at least about 5.0 µg/kg, at least about 5.5 µg/kg, at least about 6.0 µg/kg, at least about 6.5 µg/kg, at least about at least about 7.0 µg/kg, at least about 8.0 µg/kg, at least about 9.0 µg/kg, at least about 10 µg/kg, at least about 15 µg/kg, at least about 20 µg/kg, at least about 25 µg/kg, at least about 30 µg/kg, at least about 35 µg/kg, at least about 40 µg/kg, at least about 45 µg/kg, at least about 50 µg/kg, at least about 55 µg/kg, at least about 60 µg/kg, at least about 65 µg/kg, at least about 70 µg/kg, at least about 75 µg/kg, at least about 80 µg/kg, at least about 85 µg/kg, at least about 90 µg/kg, at least about 95 µg/kg, at least about 100 µg/kg, at least about 110 µg/kg, at least about 120 µg/kg, at least about 130 µg/kg, at least about 140 µg/kg, at least about 150 µg/kg, at least about 160 µg/kg, at least about 170 µg/kg, at least about 180 µg/kg, at least about 190 µg/kg, at least about 200 µg/kg, at least about 210 µg/kg, at least about 220 µg/kg, at least about 230 µg/kg, at least about 240 µg/kg, at least about 250 µg/kg, at least 5 about 260 µg/kg, at least about 270 µg/kg, at least about 280 µg/kg, at least about 290 µg/kg, at least about 300 µg/kg, at least about 310 µg/kg, at least about 320 µg/kg, at least about 330 µg/kg, at least about 340 µg/kg, at least about 350 µg/kg, at least about 360 µg/kg, at least about 370 µg/kg, at least about 380 µg/kg, at least about 390 µg/kg, at least about 400 µg/kg, at least about 420 µg/kg, at least about 440 µg/kg, at least about 460 µg/kg, at least about 480 µg/kg, at least about 500 µg/kg, at least about 600 µg/kg, at least about 700 µg/kg, at least about 800 µg/kg, at least about 900 µg/kg, at least about 1.0 mg/kg, at least about 1.5 mg/kg, at least about 2.0 mg/kg, at least about 2.5 mg/kg, at least about 3.0 mg/kg, at least about 3.5 mg/kg, at least about 4.0 mg/kg, at least about 4.5 mg/kg, at least about 5.0 mg/kg, at least about 5.5 mg/kg, at least about 6.0 mg/kg, at least about 6.5 mg/kg, at least about 10 mg/kg, or any dose within this range.

In one aspect, the at least one HGF and/or protein analog thereof disclosed herein is administered in combination with an effective dose of an ACEI. The effective daily dose of an ACEI can be at least about 1.3 to 50 mg/m$^2$/day of the subject to which the ACEI is administered. Preferably, the daily dose of the ACEI can be at least about 15 mg/m$^2$/day to about 30 mg/m$^2$/day, and more preferably 20 to 25 mg/m$^2$/day. In one aspect the ACEI is administered in combination with one or more HFG long-acting or non-acting analogs. In one aspect, the ACEI is administered in a separate composition from the composition comprising the at least one HGF and/or protein analog thereof.

In still another aspect, the effective dose of the at least one hematopoietic growth factor protein and/or analog thereof disclosed herein may be administered to the subject one time following the subject's exposure to radiation. In another embodiment, the effective dose may be administered to the subject more than one time following exposure to radiation. For example, the dose may be administered to the subject two times, three times, four times, five times, six times, seven times, eight times, nine times, ten times, or up to thirty times following radiation exposure. In still another aspect, the at least one hematopoietic growth factor protein and/or analog thereof can be administered to the subject from one to nine times following radiation exposure, more preferably from one to three times following radiation exposure and most preferably one time following radiation exposure.

In another embodiment of the invention, the step of administering the at least one hematopoietic growth factor protein and/or analog thereof disclosed herein is conducted after exposure to radiation. In some embodiments, the step of administering is conducted shortly after the exposure. For example, the step of administering can be conducted immediately after radiation exposure or within about 2 hours, within about 4 hours, within about 10 hours, within about 20 hours, within about 24 hours, within about 30 hours, within about 36 hours, within about 48 hours, and within about 72 hours of exposure. In another embodiment, the step of administering is conducted after about 24 hours after radiation exposure. In still another aspect of the invention the hematopoietic factor disclosed herein can be administered to a subject immediately after radiation exposure or up to 30 days following radiation exposure. More preferably the at least one hematopoietic growth factor protein and/or analog thereof is administered to a subject immediately after radiation exposure or up to 7 days following radiation exposure. In one preferred aspect, the at least one hematopoietic growth factor protein and/or analog thereof is administered to the subject within four hours following the subject's exposure to the radiation. In another embodiment, the step of administering is initiated at about 24 hours after exposure. In a preferred embodiment, the step of administering is initiated at about 24 hours after exposure, followed by additional administration of a hematopoietic growth factor protein analog using an every other day dosing regimen. For example, an every other day dosing regimen can be administration of the long-acting hematopoietic growth factor at 1 day, 3 days, 5 days, 7 days, 9 days, 11 days, 13 days, 15 days and 17 days after radiation exposure. In one aspect, the HGF protein analog is administered in combination with an ACEI.

The ACEI can be administered at the same time, prior to, or following administrations of the HGF protein analog as disclosed herein.

In another embodiment, the step of administering is initiated within about 24 hours after exposure followed by additional administration of a hematopoietic growth factor protein analog disclosed herein using a once per week dosing regimen. For example, a once per week dosing regimen can be administration of a single dose of the hematopoietic factor (preferably a long-acting factor) at about 24 hours after exposure, followed by another dose one week after exposure, followed by another dose the second week after exposure, followed by another dose the third week after exposure, followed by another dose the fourth week after exposure, and followed by another dose the fifth week after exposure. The per week dosing regimen can occur for about two weeks, three weeks, four weeks, five weeks, six weeks, seven weeks, eight weeks, nine weeks or ten weeks. In another embodiment, the dose may be administered once every two weeks following exposure to radiation. In still another embodiment, the dose may be administered once every three weeks following exposure to radiation. In yet another embodiment, the dose may be administered once every four weeks following exposure to radiation. In still other embodiments, more than one dose weekly may be administered.

Doses may be administered to the subject until hematopoietic recovery is achieved. This includes for example, a return of the subject's red blood cell level, platelet level and/or both levels to levels found in subjects that have not been exposed to radiation (e.g. normal levels for a subject of the same gender and similar age group and weight range). This also includes for example, a return of the subject's neutrophil level, red blood cell level, platelet level and/or any combination of two or more of these blood cell levels to levels found in subjects that have not been exposed to radiation (e.g. normal levels for a subject of the same gender and similar age group and weight range). This also includes for example, a return of the subject's neutrophil level, white blood cell level, lymphocyte level and/or any combination of two or more of these blood cell levels to levels found in subjects that have not been exposed to radiation (e.g. normal levels for a subject of the same gender and similar age group and weight range). This also includes for example, a return of the subject's neutrophil level, red blood cell level, platelet level, lymphocyte level and/or any combination of two or more of these blood cell levels to levels found in subjects that have not been exposed to radiation (e.g. normal levels for a subject of the same gender and similar age group and weight range).

In still further embodiments of the invention, the dose may be administered to the subject until several days after the subject's blood cell nadir occurs (low point of blood counts). The nadir time typically occurs between days 10-30 following exposure to radiation and is dependent upon the blood cell type (white blood cells, red blood cells, platelets, neutrophils, etc.). For instance, the nadirs for neutrophils, white blood cells, lymphocytes and platelets typically are about 10-20 days following radiation exposure. The time to reach the neutrophil and white blood cell nadir typically is longer in ARS subjects (15 days or more) than in chemotherapy-treated subjects (about 7 days). Red blood cell nadirs, hematocrit nadirs and hemoglobin nadirs typically occur later, between days 20-30 following radiation exposure, due to the longer half-life of red blood cells in the body.

Another embodiment of the invention is to provide a treatment protocol (treatment method) capable of preventing early death from hematopoietic complications of ARS and late death due to lung, kidney and heart complications of acute radiation exposure. The protocol (method) involves treating a subject who has been exposed to radiation with a combination of one or more HGFs, or combinations of one or more HGF protein analogs thereof, or combinations of HGFs and HGF protein analogs thereof and an ACEI. In one aspect of the invention in which a subject has been unintentionally exposed to radiation such as following detonation of a nuclear bomb or leak from a nuclear power plant, both the HGF and/or protein analog thereof and the ACEI are administered after the subject has been exposed to radiation. Preferably, an effective dose of the at least one HGF and/or protein analog thereof is administered within about 7 days of radiation exposure, more preferably within about 72 hours of radiation exposure, more preferably within about 48 hours of radiation exposure, more preferably within about 24 h of radiation exposure, and even more preferably within about 1 h of radiation exposure. Preferably the at least one HGF and/or protein analog thereof comprises an HGF selected from the group consisting of G-CSF, GM-CSF, and IL-11, and analogs of G-CSF, GM-CSF and IL-11 proteins, including long-acting analogs of these proteins. More preferably the HGF comprises a combination comprising a G-CSF analog plus an IL-11 analog, or a GM-CSF analog plus an IL-11 analog, or a G-CSF analog plus a GM-CSF analog, or a G-CSF analog plus a GM-CSF analog plus an IL-11 analog. Preferably, treatment with an effective dose of the ACEI is started within about 35 days of radiation exposure, more preferably within about 30 days of radiation exposure, more preferably within about 10 days of radiation exposure, more preferably within about 7 days of radiation exposure, more preferably within about 24 h post-irradiation to about day 7 following radiation exposure, more preferably within about 24 h of radiation exposure, and even more preferably within about 1 h of radiation exposure. Treatment with the ACEI should be continued for 30 days, 40 days, 50 days, 60 days, 90 days, 120 days, 150 days, 180 days, 210 days, 240 days, 270 days, 300 days, 330 days, 360 days, or 370 days to prevent death from hematopoietic complications of acute radiation exposure. Treatment with the ACEI should be continued for up to 90 days, 120 days, 150 days, 180 days, 210 days, 240 days, 270 days, 300 days, 330 days, 360 days, or 370 days to prevent death from late effects of radiation exposure, including lung, kidney and heart complications of acute radiation exposure such as lung pneumonitis, lung fibrosis and kidney nephropathy. In one preferred embodiment of the invention the subject exposed to radiation is treated with a combination comprising a long-acting G-CSF analog, a long-acting GM-CSF analog and a long-acting IL-11 analog beginning within about 24 h post-irradiation and with an ACEI beginning about day 7 post-irradiation and continuing for 150 days, 180 days, 210 days, 240 days, 270 days, 300 days, 330 days, 360 days, or 370 days. In another aspect, the subject exposed to radiation is treated with a combination comprising a non-long-acting G-CSF analog, a non-long-acting GM-CSF analog and a non-long-acting IL-11 analog beginning within about 24 h post-irradiation and continuing for 3 days, 4 days, 5 days, 6 days, 7 days, 8 days, 9 days, 10 days, 12 days, 15 days, 20 days, 25 days, 30 days, 35 days, 40 days, 45 days, 50 days, 55 days, 60 days, or 65 days following radiation exposure), and with an ACEI beginning about day 7 post-irradiation and continuing for 150 days, about 160 days, about 170 days, about 180 days, about 190 days, about 200 days, about 210 days, about 220 days, about 230 days, about 240 days, about 250 days, about 260 days, about 270 days, about 280 days, about 290 days, about 300 days, about 310 day, about 320 days, about 330 days, about 340 days, about 350 days, about 360 days, about 365 days or about 370 days. In one aspect, the combination of the HGF analogs comprises one or more non-long-acting HGF analogs with one or more long-acting HGF analogs. Optionally, the subject exposed to irradiation can be treated a second time with the combination comprising the long-acting G-CSF analog, the long-acting GM-CSF analog and the long-acting IL-11 analog on or about day 8 post-irradiation. Optionally, the subject exposed to irradiation can be treated a second time with the combination comprising the non-long-acting G-CSF analog, the non-long-acting GM-CSF analog and the non-long-acting IL-11 analog on or about day 8 post-irradiation. Optionally, the subject exposed to irradiation can be treated for a third time with the combination comprising the long-acting G-CSF analog, the long-acting GM-CSF analog and the long-acting IL-11 analog on about day 15 post-irradiation. Optionally, the subject exposed to irradiation can be treated for a third time with the combination comprising the non-long-acting G-CSF analog, the non-long-acting GM-CSF analog and the non-long-acting IL-11 analog on about day 15 post-irradiation. Optionally, treatment with the ACEI can begin within about 1 h post-irradiation, within about 24 h post-irradiation, or within about 24 h post-irradiation to about day 7 post-irradiation. In one aspect, one or more non-long-acting HGFs and analogs thereof are administered daily until hematopoietic recovery has been achieved, such as for 16-23 days after irradiation.

In another embodiment, the method of the present invention is directed toward the administration of one or more single effective doses of at least one hematopoietic growth factor protein and/or analog thereof as disclosed herein prior to a subject's radiation exposure to reduce the severity of radiation-related complications. In one aspect, the HGF or protein analog thereof is administered in combination with an ACEI. In one aspect, the ACEI is administered at the same time, or prior to, or following administration of the at least one HGF and/or protein analog thereof. In one aspect, the ACEI is administered separately. In one aspect, the prior administration of the hematopoietic growth factor protein analog may prevent radiation-related complications. In another aspect, the administration of an effective dose of the at least one hematopoietic growth factor protein and/or analog thereof prior to a subject's radiation exposure accelerates hematopoietic recovery after the subject is exposed to radiation. In one embodiment, one or more single effective doses of the least at one hematopoietic growth factor protein and/or analog thereof may be administered to the subject at least about 24 hours prior to exposure. In still another aspect, one or more single effective doses of the hematopoietic growth factor protein analog will be administered to the subject at least about 2 days, 5 days, 7 days, 15 days, 30 days, 45 days, 60 days, up to 6 months prior to the subject's exposure to radiation. In still another embodiment, the subject is administered one or more single effective doses of the at one hematopoietic growth factor protein and/or analog at least about 20 hours, 10 hours or 5 hours prior to exposure to radiation. Effective dose amounts of the hematopoietic factor protein analog that are administered to the subject prior to the subject's exposure to radiation are similar to the effective dose amounts administered to a subject following exposure to radiation as discussed above. A single effective dose is at least about 0.1 µg per kg of the subject to which the long acting hematopoietic growth factor protein or analog thereof is administered, up to an including at least about 10 mg/kg, or any dose within this range. Doses may also be given to a subject following an every other day dosing regimen wherein one or more single doses are given over a period of time every other day prior to the subject's exposure to radiation. Doses may also be given to a subject following a once per week dosing regimen over a period of time prior to exposure to radiation.

In another aspect, the subject can be administered an effective dose of a non-long-acting HGF analog or an effective dose of a long acting-HGF analog in a single dose that provides increased survival and/or accelerated hematopoietic recovery. In one aspect, the single dose can be at least about 0.1 µg to 5 mg per kg of the subject to which the non-long-acting or long-acting HGF analog is administered. Preferably, the single dose can be at least about 5 µg/kg to about 1 mg/kg, and more preferably 10 µg/kg to about 300 µg/kg. One or more single doses of the non-long-acting HGF analog can be given daily by sc injection until hematopoietic recovery (e.g., neutrohil and/or platelet recovery) has been achieved. In one aspect, the one or more single doses is administered daily for 14 days, 15 days, 16 days, 17 days, 18 days, 19 days, 20 days, 21 days, 22 days, 23 days, 24 days, 25 days, 26 days, 27 days, 28 days, 29 days, 30 days, 40 days, 50 days, or 60 days. In one aspect, more than one single dose of the HGF protein analog or the combination of HGF protein analogs is administered. In one aspect, a single dose is administered.

In still another aspect, the subject is administered one or more single doses of the HGF protein analog or the combination of HGF protein analogs, wherein the HGF protein analogs can be non-long acting or long-acting HGF protein analogs. In another aspect, the subject is administered a single dose of the long-acting HGF protein analog or combination of HGF protein analogs one to nine times following the subject's exposure to radiation. In yet another aspect, the subject is administered a single dose of the long-acting HGF protein analog or combination of HGF protein analogs one to three times following the subject's exposure to radiation. In yet another aspect, the subject is administered a single dose of the long-acting HGF protein analog or combination of HGF protein analogs two times following the subject's exposure to radiation. In still another aspect, the subject is administered one single dose of the long-acting HGF analog or combination of HGF protein analogs.

In another aspect, one or more single doses of the long acting HGF protein analog or combination of HGF protein analogs is administered to the subject within 24 hours following the subject's exposure to the radiation. In still another aspect, the subject is administered one or more single doses of the long acting HGF protein analog or combination of HGF protein analogs using an every other day dosing regimen. In yet another aspect, the subject is administered one or more single doses of the long acting HGF protein analog or combinations of HGF protein beginning at least 24 hours following the subject's exposure to the radiation followed by a weekly dosing regimen.

Another aspect of the invention relates to a method for enhancing immune reconstitution and preventing or reducing the severity of residual bone marrow damage (RBMD) following irradiation by administering to a subject who has been exposed to radiation effective doses of one or more HGFs, particularly IL-11 or IL-11 analogs such as PEG IL-11, and HGF combinations containing IL-11 or IL-11 analogs such as PEG IL-11.

Another aspect of the invention relates to a method for increasing weight and cellularity of lymphoid organs such as spleen, lymph nodes, and thymus, and increasing numbers of thymocytes and lymphocytes in irradiated animals by administering to a subject who has been exposed to radiation effective doses of one or more HGFs, particularly IL-11 and IL-11 analogs such as PEG IL-11, and HGF combinations containing IL-11 and IL-11 analogs such as PEG IL-11.

Another aspect of the invention relates to a method for normalizing radiation-induced changes in double negative 3 (DN3) and double negative 4 (DN4) thymocyte populations (e.g., a method for increasing the percentage DN3 thymocytes and decreasing the percentage of DN4 thymocytes) by administering to a subject who has been exposed to radiation effective doses of one or more HGFs, particularly IL-11 or IL-11 analogs such as PEG IL-11, and HGF combinations containing IL-11 or IL-11 analogs such as PEG IL-11.

A further aspect of the invention relates to a method for decreasing radiation-induced damage to multiple organ systems, including the hematopoietic system, lung, kidney, and heart, and increasing survival by administering to a subject who has been exposed to radiation an effective dose of an ACEI beginning following irradiation and continuing treatment for up to 90 days post-irradiation, more preferably for up to 150 days post-irradiation, and even more preferably for up to 12 months post-irradiation. Damage to the hematopoietic system, lung, kidney, and heart is reduced and survival is increased even when treatment with the ACEI is begun 7 days post-irradiation and continued for up to 150 days or longer (up to 12 months). Optionally, treatment with the ACEI can begin within about 1 h post-irradiation, within about 24 h post-irradiation, within about 24 h post-irradiation to about day 7 post-irradiation, within about 7 days post-irradiation, or within about 35 days post-irradiation.

A further aspect of the invention relates to a method for decreasing radiation-induced damage to multiple organ systems, including the hematopoietic system, lung, heart and kidney, and increasing survival by administering to a subject who has been exposed to radiation effective doses of one or more HGFs and an effective dose of an ACEI. In one aspect, the HGF is an analog as disclosed herein.

Another aspect of the invention relates to a method for improving survival from radiation exposure in a subject who has been exposed to a myelosuppressive dose of radiation, comprising administering to the subject an effective dose of an angiotensin-converting enzyme inhibitor (ACEI). In one aspect, the effective dose of the ACEI is a dose of at least about 1.3 to 50 mg/m$^2$/day. In another aspect, the subject is administered the ACEI daily beginning within 7 days following the subject's exposure to the radiation. In another aspect, the subject is administered the ACEI daily beginning between about 24 hours post-irradiation to within about 7 days following the subject's exposure to the radiation. In another aspect, the subject is administered the ACEI daily beginning between about 48 hours post-irradiation to within about 7 days following the subject's exposure to the radiation.

A further aspect of the invention relates to a method for decreasing lung morbidity in a subject who has been exposed to a myelosuppressive dose of radiation, comprising administering to the subject an effective dose of an ACEI following radiation exposure.

Another aspect of the invention relates to a method for reducing damage to one or more organ systems selected from the group consisting of lung, kidney, heart, and combinations thereof, in a subject who has been exposed to a myelosuppressive dose of radiation, comprising administering to the subject an effective dose of an ACEI following radiation exposure.

Still a further aspect of the invention relates to a method for decreasing hematopoietic morbidity, renal morbidity, and/or lung morbidity due to a myelosuppressive dose of radiation exposure by administering to a subject who has been exposed to radiation an ACEI.

In embodiments of the present invention, the ACEI is administered to the subject in a dose that provides therapeutic benefits to the subject. Therapeutic benefits include but are not limited to accelerated hematopoietic recovery, and/or reduced lung damage (pneumonitis and fibrosis), and/or reduced kidney damage (nephropathy), and/or reduced heart damage, and/or survival benefits (improved survival) to subjects. Survival benefits include an increase in life expectancy of a subject that has been exposed to radiation. According to the present invention, an effective administration protocol (i.e., administering the ACEI in an effective manner) comprises suitable dose parameters and modes of administration that result in the desired effect in the subject (e.g., acceleration of hematopoietic recovery, increased survival, reduced lung damage, reduced kidney damage). In accordance with the present invention, a suitable single dose size is a dose that results in the desired therapeutic effect in the subject, when administered one or more times over a suitable time period. Doses can vary and one of skill in the art can readily determine appropriate single dose sizes for a given subject based on the size of a patient and the route of administration. In one aspect of the invention, a suitable single dose of the ACEI of the present invention is an amount that, when administered by any route of administration, provides a therapeutic effect in the subject as described above, as compared to a patient which has not been administered the ACEI (i.e., a control), as compared to the subject prior to administration of the ACEI. In one aspect, the ACEI is administered orally, such as in pill form. In still another aspect, the ACEI is administered separately, but in combination with one or more of the HGF proteins and/or analogs thereof disclosed herein.

Suitable administration protocols include any in vivo or ex vivo administration protocol. preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, sublingual administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition. Particularly preferred routes of delivery of the HGF protein or analogs thereof disclosed herein include subcutaneous and intravenous delivery. A particularly preferred route of delivery for ACEI is oral delivery. Preferred oral formulations of the ACEI include pills, tablets, fast dissolving tablets, orally disintegrating tablets, orally dissolving tablets, and liquid formulations.

Ex vivo administration refers to performing part of the regulatory step outside of the patient, such as administering a composition of the present invention to a population of cells removed from a patient under conditions such that the composition contacts and/or enters the cell, and returning the cells to the patient. Ex vivo methods are particularly suitable when the target cell type can easily be removed from and returned to the patient. Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

The present invention is also directed toward a pharmaceutical composition comprising one or more hematopoietic factor protein analogs disclosed herein and a pharmaceutical acceptable carrier. In one embodiment, the protein analog is selected from a long-acting G-CSF analog, a long-acting GM-CSF analog, a long-acting GH analog or a long-acting IL-11 analog. In still another embodiment, the pharmaceutical composition is administered to the patient following radiation exposure. In one aspect the composition further comprises an ACEI. In still another aspect, the ACEI is in a separate composition from the compositions comprising the HGF protein analog(s).

Hematopoietic factor protein analogs of the present invention are preferably administered in a composition. Compositions can include a hematopoietic factor protein analog of the invention and any other suitable pharmaceutically acceptable carrier, as well as, in some aspects, additional components that may be useful in the treatment of radiation exposure. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where the long acting hematopoietic factor protein analog will provide a detectable effect as compared to in the absence of the long acting hematopoietic factor protein analog. Preferred pharmaceutically acceptable carriers are capable of maintaining the long acting hematopoietic factor protein analog of the present invention in a form that, upon arrival of the analog at the cell target in a culture or in a subject, the analog is capable of interacting with its target (e.g., hematopoietic cell for GM-CSF).

Suitable excipients of the present invention include excipients or formularies that transport or help transport, but do not specifically target a composition to a cell or area (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a subject or culture. As used herein, a controlled release formulation comprises a cysteine mutein of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liospheres, and transdermal delivery systems. Other carriers of the present invention include liquids that, upon administration to a subject, form a solid or a gel in situ. Preferred carriers are also biodegradable (i.e., bioerodible). In the event that a long acting hematopoietic factor protein analog of the invention is administered as a recombinant nucleic acid molecule encoding the analog (e.g., gene therapy or genetic immunization), suitable carriers include, but are not limited to, liposomes, viral vectors or other carriers, including ribozymes, gold particles, poly-Lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a subject, thereby targeting and making use of a compound of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle of the present invention is a liposome. A liposome is capable of remaining stable in an animal for a sufficient amount of time to deliver a nucleic acid molecule or protein described in the present invention to a preferred site in the animal. A liposome, according to the present invention, comprises a lipid composition that is capable of delivering a nucleic acid molecule or protein to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another type of delivery vehicle, when the hematopoietic factor protein analog disclosed herein is administered as a nucleic acid encoding the analog, comprises a viral vector. A viral vector includes an isolated nucleic acid molecule, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The data presented in the following examples, demonstrate the use of PEG-G-CSF (BBT-015) and PEG-GM-CSF (BBT-007) to serve as effective medical countermeasures against high radiation exposure via increasing hematopoietic recovery and subject survival. Unexpectedly, the inventors discovered that these proteins accelerate recovery of multiple hematopoietic cell lineages including neutrophils, white blood cells, lymphocytes, red blood cells, and platelets following radiation exposure. The inventors discovered that these proteins also accelerate recovery of hemoglobin and hematocrit levels following radiation exposure. Surprisingly, previous studies with G-CSF and GM-CSF analogs suggested that treatment with these proteins had no effect or decreased platelet and red blood cell levels (see for example Cox, G. N., et al. (2004) Enhanced circulating half-life and hematopoietic properties of a human granulocyte colony-stimulating factor (G-CSF)-immunoglobulin fusion protein. Exp. Hematol. 32, 441-449), which is contrary to the findings of the present invention.

The following experimental results are provided for purposes of illustration and are not intended to limit the scope of the invention.

EXAMPLES

Example 1

This example shows that treating irradiated mice with certain combinations of hematopoietic growth factor protein analogs increased 30-day survival more than the individual hematopoietic growth factors in a Mouse Acute Radiation Syndrome (ARS) Survival Assay.

The efficacy of three individual HGFs and all possible combinations of the 3 proteins to increase 30 day survival of lethally irradiated mice was tested at an LD95/30 radiation dose (a dose of radiation expected to cause death to 95% of an exposed population within 30 days). The mouse acute radiation syndrome (ARS) survival assay used for these studies is described in Plett et al. (Plett, P A, et al. (2012) Establishing a murine model of the Hematopoietic Syndrome of the Acute Radiation Syndrome. Health Physics 103: 343-355; Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20) and in U.S. patent publication No. 20120288475. Similar methods were used in the studies described below. Male and female mice (*Mus musculus*, C57BL/6 strain), aged 10-12 weeks upon study initiation, were used for these studies. There were 40 animals per treatment group, 50% males and 50% females. Each study had 8 test groups as indicated in Table 1 below. A dose of radiation equal to the LD95/30 was delivered as a single uniform total body dose (TBD) of gamma radiation from a $^{137}$Cs radiation source (GammaCell 40; Nordion International, Kanata, Ontario, Canada) at an exposure rate of 98.575-100.3±5.01 cGy/minute. Pilot studies determined the LD95/30 dose of radiation to be 927 cGy. This radiation dose causes severe hematopoietic ARS and mild gastrointestinal ARS (Booth C, et al. (2012) Acute gastrointestinal syndrome in high-dose irradiated mice. Health Physics 2012; 103(4): 383-399; Plett, P A, et al. (2012) Establishing a murine model of the Hematopoietic Syndrome of the Acute Radiation Syndrome. Health Physics 103: 343-355). Each group of mice irradiated together in the same irradiation pie was roughly divided among all groups to ensure that each group received the same irradiation exposure conditions. After irradiation mice were randomized to one of the Test Article or Control Article groups. Mice were provided acidified water (pH 2.0-3.0) in bottles and fed certified commercial extruded laboratory animal chow (HARLAN 2018SXC) throughout the study. On day 4 post-exposure, mice were provided acidified autoclaved water in bottles and also in wetted chow (HARLAN 2018SXC) in a petri dish set in the bottom of the cage. Mice were monitored for survival once per day until signs of early euthanasia appear, then twice per day until day 30. Mice meeting predetermined euthanasia criteria were euthanized.

Complete Blood Cell Counts (CBCs) with differential and peripheral smears were performed at baseline (pre-irradiation) and on days 10, 20, 25, and 30 post-TBI. Two randomly selected mice/group in different cages were bled on day −3 to day −1 prior to TBI for a total of 12 baseline CBCs. Four randomly selected mice/group were bled on days 10, 20, 25, and 30 post-TBI. When possible, the same number of males and females in each group and in separate cages were selected for bleeding. Each mouse was bled a maximum of two times during the study and bleeds were at least 14 days apart. CBCs with differentials and peripheral smears also were performed on four non-irradiated age-matched control mice/time point as hematology controls.

The Test Articles (TA) used in this study were PEG-G-CSF analog BBT-015 [human G-CSF (C17S/A141C) modified with a 40 kDa-PEG], murine PEG-GM-CSF analog BBT-007 (the murine BBT-007 GM-CSF homolog T3C modified with a 40 kDa-PEG), and PEG-IL-11 analog BBT-059 [human IL-11 (179C) modified with a 40 kDa-PEG]. The Test Articles are described in Plett et al. (Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20) and U.S. patent application 20120288475. The Test Article and Control Article (CA; vehicle solutions) were administered by subcutaneous (sc) injection at 24+4/−0 hours after irradiation. The TA doses administered were 1 mg/kg (20 µg/20 gm mouse) for BBT-015 and muBBT-007, and 0.3 mg/kg (6.0 µg/20 gm mouse) for BBT-059. The proteins were formulated in Vehicle solution, which was 10 mM sodium phosphate, 4% mannitol, 1% sucrose pH 6.2. The volume of injection per mouse was about 100 µL. Mice were weighed during the acclimation period and an average weight of all females and all males was calculated separately. All females were dosed based on the average weight of the females, and all males were dosed based on the average weight of the males.

As indicated in Table 1, mice treated with vehicle had a 30-day survival rate of 7.5%, which was lower than the survival rate of mice treated with PEG-IL-11 (63% survival rate), PEG-G-CSF (50% survival rate) or PEG-GM-CSF (33% survival rate). Treating irradiated mice with a combination of all 3 growth factors (PEG-G-CSF+PEG-GM-CSF+PEG-IL-11) resulted in the highest survival rate (80% survival). The next most effective combination for increasing survival was PEG IL-11+PEG GM-CSF (73% survival). All of the two protein combinations (PEG-G-CSF+PEG-IL-11; PEG-GM-CSF+IL-11; PEG-G-CSF+PEG-GM-CSF) had higher 30-day survival rates than mice treated with the individual proteins or vehicle.

TABLE 1

30-day survival of LD95/30 irradiated mice treated with a single sc injection of PEG IL-11 (0.3 mg/kg), PEG-G-CSF (1 mg/kg) or PEG muGM-CSF (1 mg/kg), or combinations of the proteins. There were 40 mice (20 males/20 females) per test group.

| Test Group | % 30-d survival | (# survivors/total mice) |
|---|---|---|
| 1. Vehicle | 7.5 | 3/40 |
| 2. PEG-G-CSF | 50 | 20/40 |
| 3. PEG GM-CSF | 32.5 | 13/40 |
| 4. PEG IL-11 | 62.5 | 25/40 |
| 5. PEG-IL-11 + PEG-G-CSF | 65 | 26/40 |
| 6. PEG-IL-11 + PEG-GM-CSF | 72.5 | 29/40 |
| 7. PEG-GM + PEG-G-CSF | 55 | 22/40 |
| 8. PEG-IL-11 + PEG-GM-CSF + PEG-G-CSF | 80 | 32/40 |

Figure 1B:
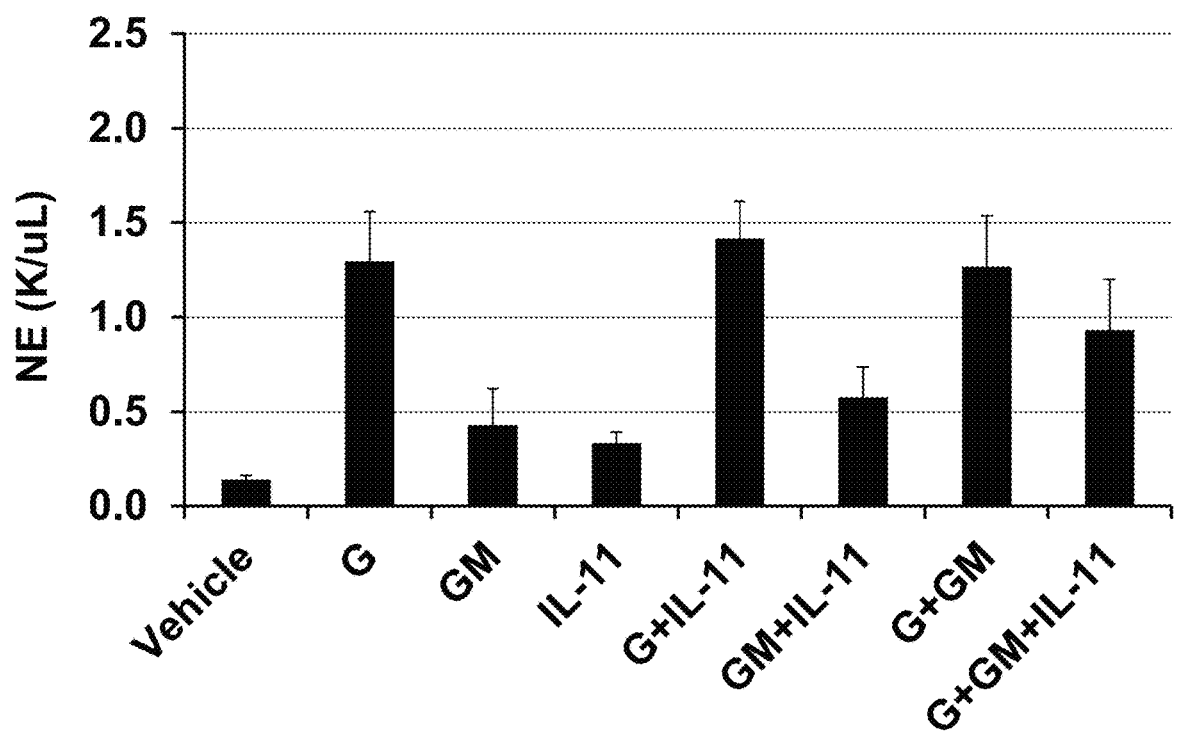
Figure 1C:
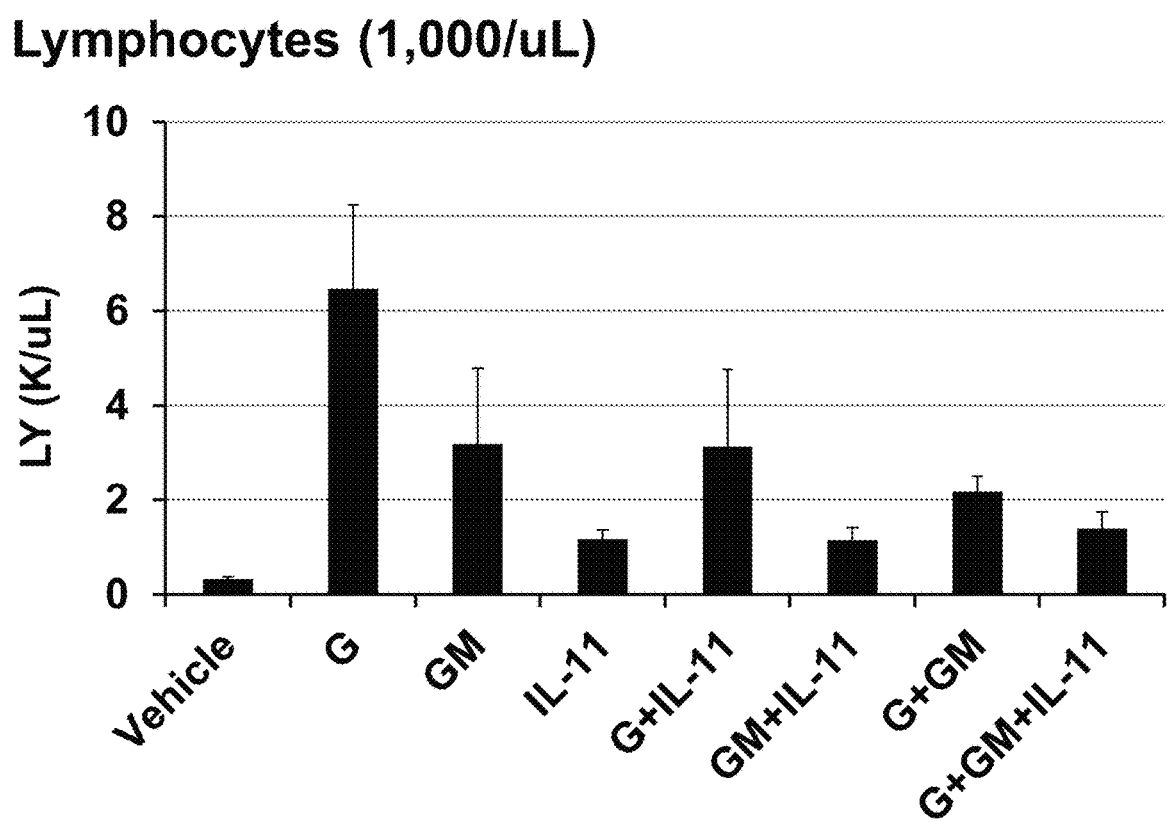
Figure 1D:
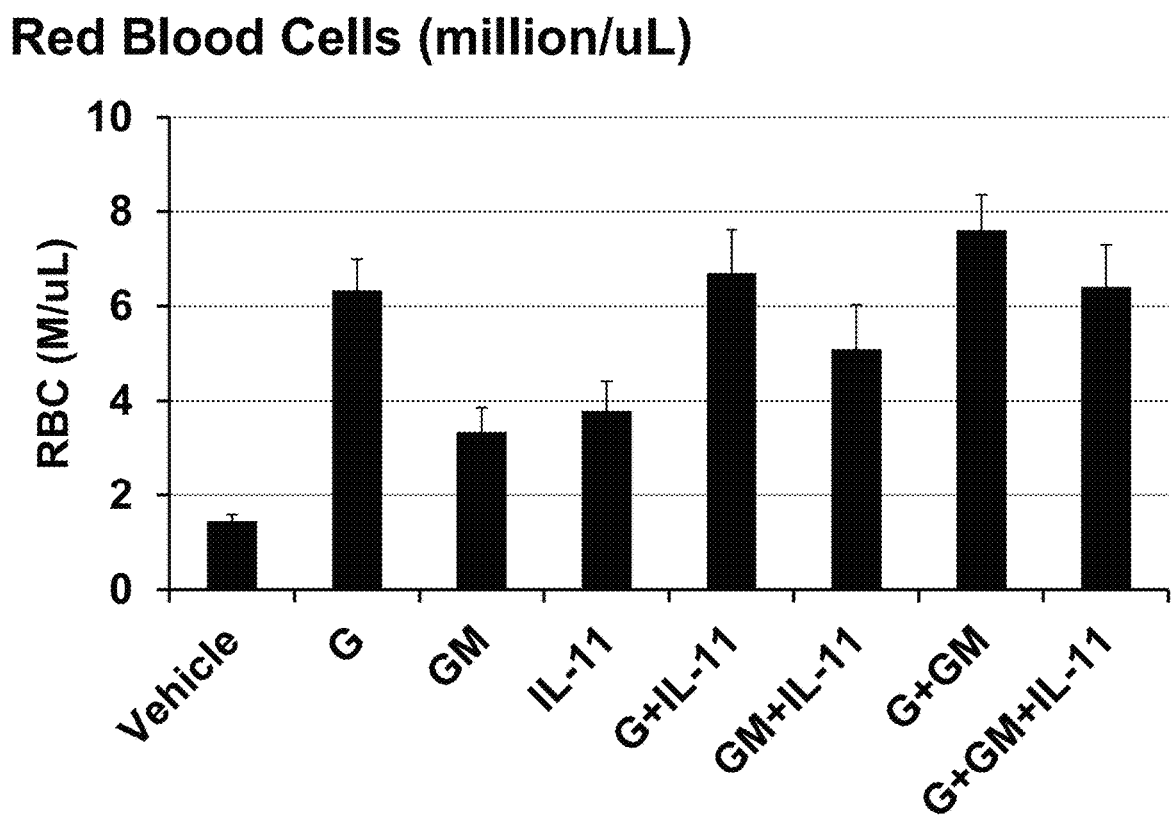
Figure 1E:
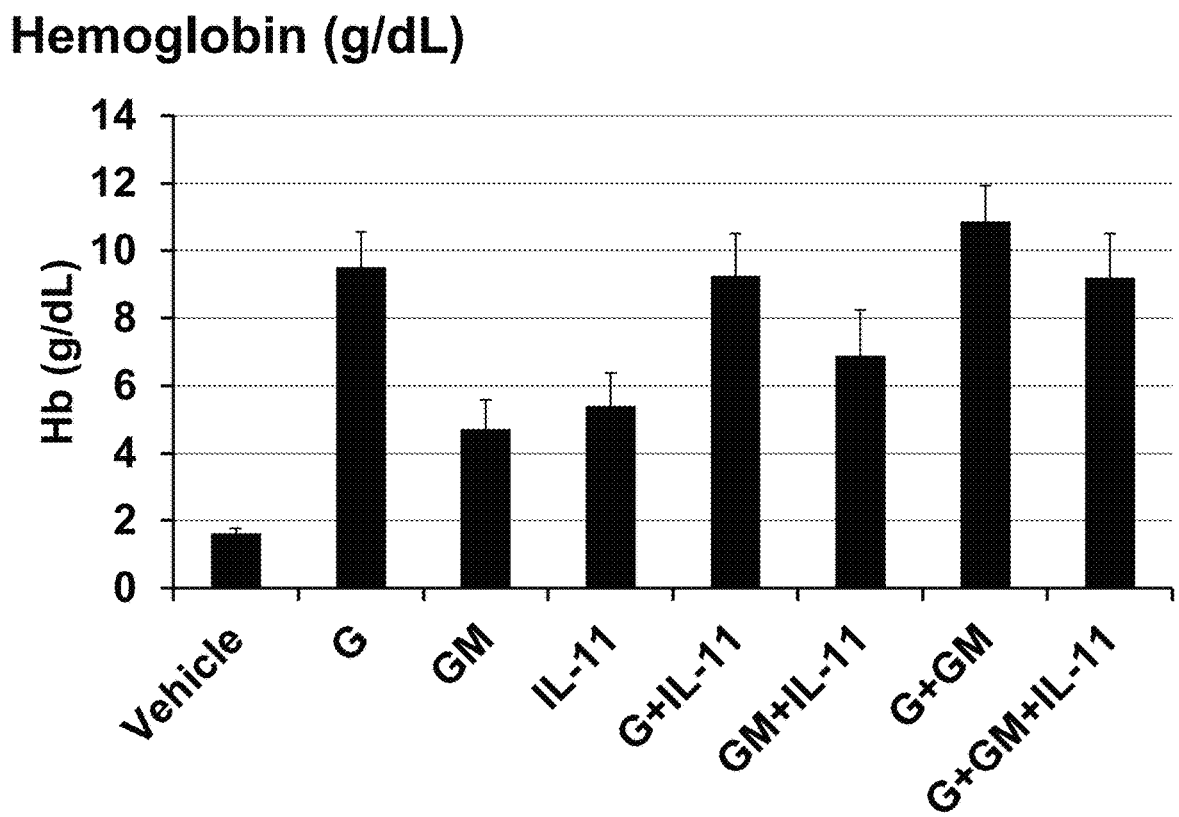
Figure 1F:
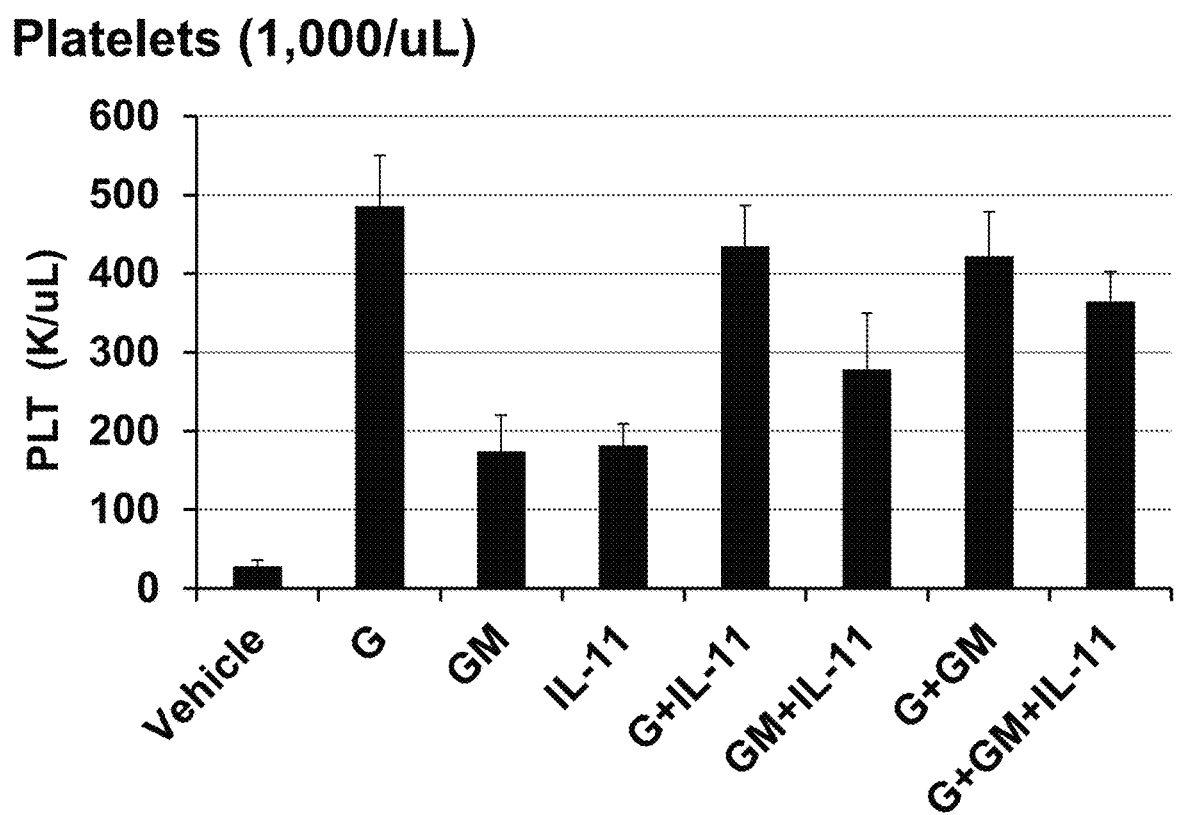

Mice treated with the individual HGFs and two or three HGF protein combinations displayed accelerated hematopoietic recovery compared to vehicle-treated mice, as evidenced by greater numbers of neutrophils, white blood cells, platelets, red blood cells and lymphocytes on day 20 post-TBI compared to vehicle-treated mice (FIGS. 1A-1F).

This Example demonstrates that PEG-G-CSF, PEG-GM-CSF and PEG-IL-11 administered individually once by sc injection at 24 h post irradiation improve 30-day survival of 927 cGy (estimated LD95/30) irradiated mice compared to Vehicle The Example further demonstrates that treating irradiated mice with combinations of two or three of the HGF proteins increased survival more than the individual HGF proteins, and that treating irradiated mice with a combination comprising all three HGF proteins provides the highest level of survival (higher survival than Vehicle, the individual HGF proteins or combinations comprising two of the HGF proteins). The data also indicate that treating irradiated mice with the individual HGF proteins and combinations of the HGF proteins can accelerate recovery of multiple types of hematopoietic cells, including neutrophils, white blood cells, lymphocytes, red blood cells and platelets, compared to Vehicle solution, following radiation exposure.

Example 2

This example shows that treating irradiated mice with the Hematopoietic Growth Factor Triple Combination (TC) and an Angiotensin Converting Enzyme Inhibitor (ACEI) increased 30-day survival and 12 month survival more than either treatment alone.

The following study demonstrates that treating irradiated mice with a triple combination (TC) of 3 HGFs (PEG-G-CSF analog BBT-015, PEG-GM-CSF analog murine BBT-007, and PEG IL-11 analog BBT-059) and a representative Angiotensin Converting Enzyme inhibitor (ACEI), Lisinopril, results in higher 30-day survival rates than does treating irradiated mice with TC or Lisinopril alone, or with Vehicle solution. The study also demonstrates that treating lethally irradiated mice with Lisinopril from day 7 through day 30 results in higher 30-day survival rates than does not treating irradiated mice with Lisinopril during this time period. For this study, C57BL/6 female mice (12 week old at study initiation) were exposed to 904 cGy (estimated LD90/30 radiation dose) and randomized to the four test groups shown in Table 2. At 24+4/−0 hours post-irradiation, mice received a single sc injection of the TC [PEG-G-CSF (1 mg/kg); murine PEG-GM-CSF (1 mg/kg); and PEG-IL-11 (0.3 mg/kg) in 10 mM sodium phosphate, 4% mannitol, 1% sucrose pH 6.2 (vehicle solution)] or Vehicle solution (10 mM sodium phosphate, 4% mannitol, 1% sucrose pH 6.2). On day 7 through day 30 post-TBI mice were given autoclaved acidified water or autoclaved acidified water containing Lisinopril (60 mg/mL) ad libitum. This Lisinopril concentration translates to a dose of about 9 mg/kg (180 micrograms/20 g mouse), assuming mice drink 3 mL water/day (Plett, P A, et al. (2012) Establishing a murine model of the Hematopoietic Syndrome of the Acute Radiation Syndrome. Health Physics 103: 343-355). The Lisinopril drinking water was made fresh weekly and stored at 2-8° C. for no more than 8 days. Animals were monitored for survival through day 30. Beginning on day 4 post-irradiation and continuing until day 30 post-irradiation, mice were provided chow (Harlan 2018SXC) wetted with acidified autoclaved water in a Petri dish set in the bottom of the cage. From Day 7 to study end on Day 30, mice in the Lisinopril groups received chow wetted with Lisinopril water, and Lisinopril water in water bottles. The results from this experiment are presented in Table 2. Control mice treated with the Vehicle on Day 1 and autoclaved acidified water from Day 7 to Day 30 had a 30-day survival rate of 5.1%. Mice treated with Vehicle on Day 1 and Lisinopril from day 7 to day 30 had a significantly higher 30-day survival rate of 29.6% (p<0.001 versus Vehicle). Mice treated with the TC on Day 1 and autoclaved acidified water on Days 7 to 30 had a 30-day survival rate of 72.7%, whereas mice treated with the TC on Day 1 and with Lisinopril on days 7 to 30 had a 30-day survival rate of 100%.

The 12 month survival and Mean Survival Time (MST) of decedents was also assessed for the mice in this study (Table 2). Control mice treated with the Vehicle on Day 1 and autoclaved acidified water from Day 7 to Day 30 had a 12 month survival rate of 2.5% and an MST of 23.8 days. Mice treated with Vehicle on Day 1 and Lisinopril from day 7 to day 30 had a higher 12 month survival rate of 13.6% and longer MST of 34.8 days. Mice treated with the TC on Day 1 and autoclaved acidified water on Days 7 to 30 had an even higher 12 month survival rate of 54.5% and a greater MST of 76 days. Mice treated with the TC on Day 1 and with Lisinopril on days 7 to 30 had the highest 12 month survival rate of 66.7% and longest MST of 209.7 days.

TABLE 2

30-day survival, 12 month survival, and Mean Survival Time (MST) of decedents of LD90/30 irradiated mice treated with a Triple Combination (TC; PEG-G-CSF analog BBT-015, murine PEG-GM-CSF analog BBT-007, and PEG IL-11 analog BBT-059) alone and in combination with Lisinopril. Irradiated mice received a single sc injection of the Triple Combination [TC, comprising PEG IL-11 (0.3 mg/kg), PEG-G-CSF (1 mg/kg) and PEG muGM-CSF (1 mg/kg)] or Vehicle solution (10 mM sodium phosphate, 4% mannitol, 1% sucrose pH 6.2) at 24 h + 4/−0 h post-irradiation. From day 7 through day 30 mice were given autoclaved acidified water or autoclaved acidified water containing Lisinopril. MST, mean survival time of decedents.

| Test group | 30 day survival (number alive/total) | % 30 day survival | % 12 month survival | MST (days) |
|---|---|---|---|---|
| 1. TC | 8/11 | 72.7 | 54.5 | 76.0 |
| 2. TC + Lisinopril | 9/9 | 100 | 66.7 | 209.7 |
| 3. Vehicle + Lisinopril | 24/81 | 29.6 | 13.6 | 34.8 |
| 4. Vehicle | 4/79 | 5.1 | 2.5 | 23.8 |

Example 3

This example shows that BBT-015 (PEG G-CSF) improves 30 day survival of lethally irradiated mice when administered 36 to 38 h post-irradiation and 48 to 50 h post-irradiation.

Daily sc injections of human G-CSF (filgrastim (Neupogen, Amgen, Inc.) at 0.01 mg/kg/day for 16-23 days increased 60-day survival of rhesus monkeys when administered at 24 h post-TBI, but not when administered at 48 h post-TBI (Farese A M, et al. (2012) A nonhuman primate model of the hematopoietic syndrome plus medical management. Health Physics 103: 367-382; Farese, A M, et al. (2013) Filgrastim improves survival in lethally irradiated nonhuman primates. Radiation Research 179: 89-100; Farese A M, et al. (2014) The ability of filgrastim to mitigate mortality following LD50/60 total-body irradiation is administration time-dependent. Health Physics 106: 39-47). The PEGylated G-CSF analog BBT-015 was tested to determine if it could improve 30-day survival of irradiated mice when administered 36-38 h or 48-50 h post-irradiation. Male and female C57BL/6 mice (10-12 week old at study initiation; 10 males and 10 females per treatment group) were exposed to 853 cGy (estimated LD50/30) and 872 cGy (estimated LD70/30) radiation doses and randomized into test groups as shown in Table 3. Control mice received a single sc injection of vehicle solution (10 mM sodium acetate, 5% sorbitol, 0.003% polysorbate 20, pH 4.0) at 36-38 h or 48-50 h post irradiation. BBT-015-treated mice received a single sc injection of BBT-015 (1 mg/kg in 10 mM sodium acetate, 5% sorbitol, 0.003% polysorbate 20, pH 4.0) at 36-38 h or 48-50 h post irradiation. Survival was followed for 30 days. CBC analyses were performed at pre-dose, and on days 10, 20, 25 and 30 post-TBI, as described in the Example 1.

As shown in Table 3, BBT-015 administration significantly improved 30-day survival versus vehicle solution when administered 36-38 h post-irradiation. 55% of mice exposed to cGy and treated once with BBT-015 at 36-38 h post-irradiation were still alive at 30 days, compared to 5% of vehicle-treated mice. Similarly, 75% of mice exposed to 872 cGy and treated once with BBT-015 at 36-38 h post-irradiation were still alive at 30 days, compared to 45% of vehicle-treated mice. Combining the data from these two radiation doses, 65% of mice treated once with BBT-015 at 36-38 h post-irradiation survived 30 days, compared to only 25% of mice treated with vehicle solution.

BBT-015 also increased survival when administered at 48-50 h post-irradiation. As shown in Table 3, 65% of mice exposed to 853 cGy and treated once with BBT-015 at 48-50 h post-irradiation were still alive at 30 days, compared to 60% of vehicle-treated mice. At the higher 872 cGy radiation dose, 30% of mice treated once with BBT-015 at 48-50 h post-irradiation were still alive at 30 days, compared to 10% of vehicle-treated mice. Combining the data from these two radiation doses, 47.5% of mice treated once with BBT-015 at 48-50 h post-irradiation survived 30 days, compared to only 35% of mice treated with vehicle solution.

TABLE 3

30-day survival of mice exposed to 853 cGy or 872 cGy and treated with a single sc injection of BBT-015 (1 mg/kg) or Vehicle solution at 36-38 h or 48-50 h post-irradiation.

| Group | Radiation dose | Time of Dosing post-irradiation | Number of Mice | Number Alive on Day-30 | % Alive on Day 30 |
|---|---|---|---|---|---|
| 1. BBT-015 | 853 cGy | 36-38 hr | 20 (10M/10F) | 11 | 55 |
| 2. Vehicle | 853 cGy | 36-38 hr | 20 (10M/10F) | 1 | 5 |
| 3. BBT-015 | 872 cGy | 36-38 hr | 20 (10M/10F) | 15 | 75 |
| 4. Vehicle | 872 cGy | 36-38 hr | 20 (10M/10F) | 9 | 45 |
| 5. BBT-015 | 853 cGy | 48-50 hr | 20 (10M/10F) | 13 | 65 |
| 6. Vehicle | 853 cGy | 48-50 hr | 20 (10M/10F) | 12 | 60 |
| 7. BBT-015 | 872 cGy | 48-50 hr | 20 (10M/10F) | 6 | 30 |
| 8. Vehicle | 872 cGy | 48-50 hr | 20 (10M/10F) | 2 | 10 |

Figure 2A:
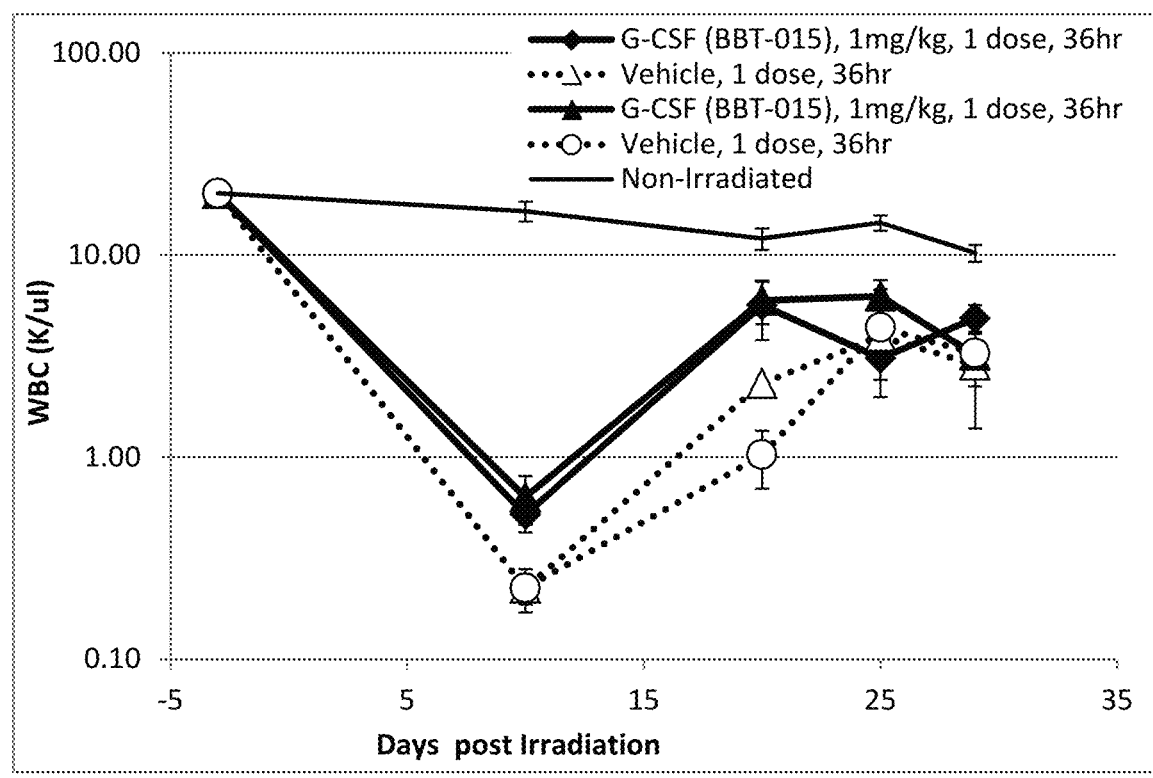
FIGS. 2A-2F show changes in white blood cells, WBC (FIG. 2A); neutrophils, NE (FIG. 2B); lymphocytes, LY (FIG. 2C); red blood cells, RBC (FIG. 2D); hemoglobin, Hg (FIG. 2E); platelets, PLT (FIG. 2F), overtime in 853 cGy-irradiated mice treated with a single sc injection of vehicle (Control Article) or 1 mg/kg PEG G-CSF analog BBT-015 at 36 h or 48 h post-TBI.
Figure 2B:
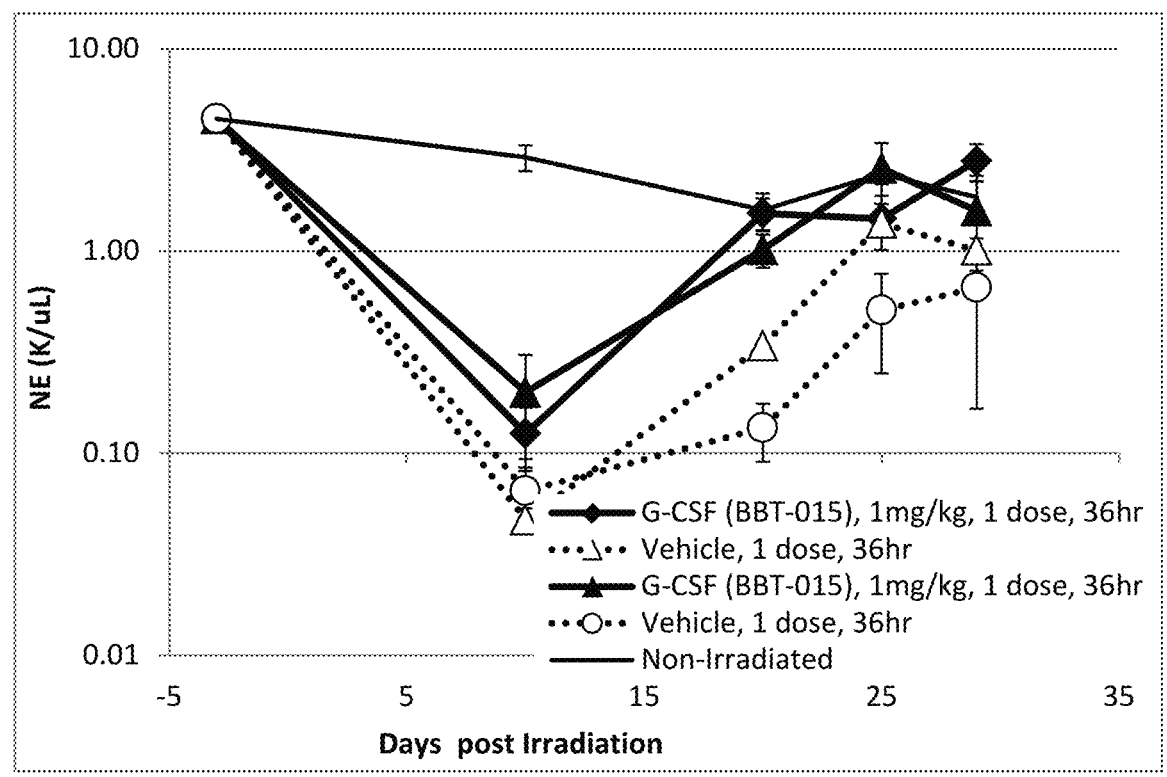
Figure 2C:
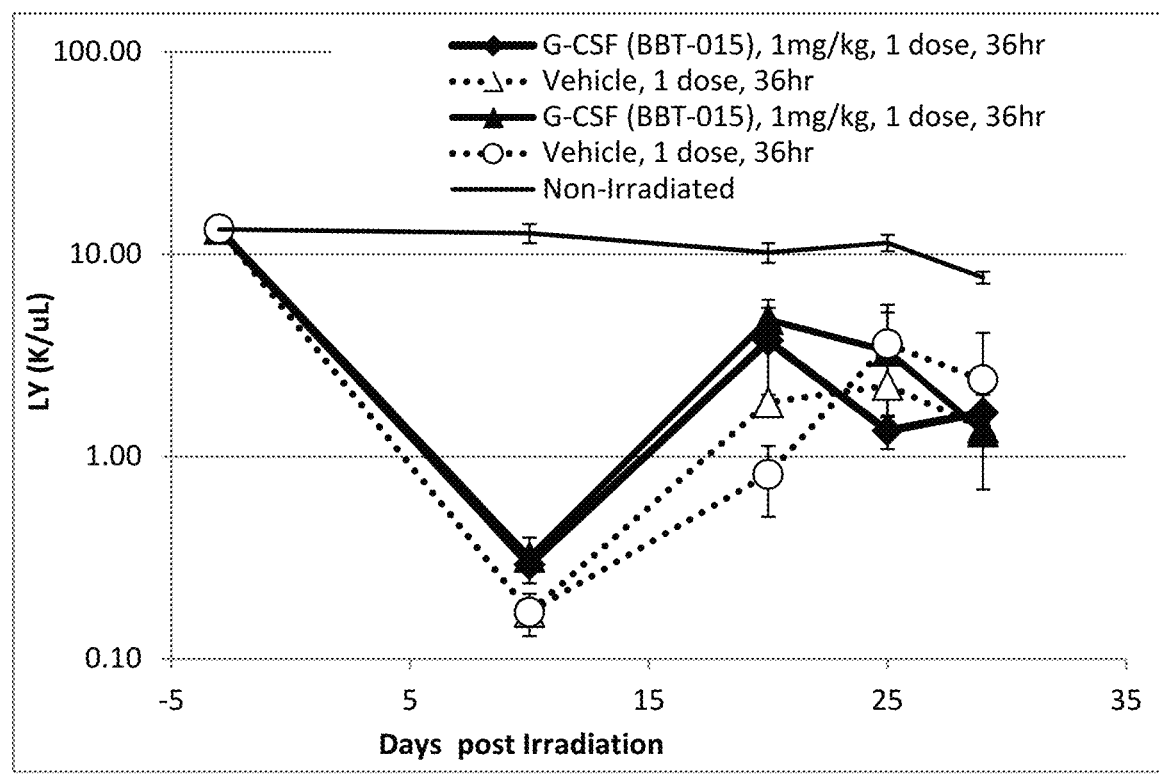
Figure 2D:
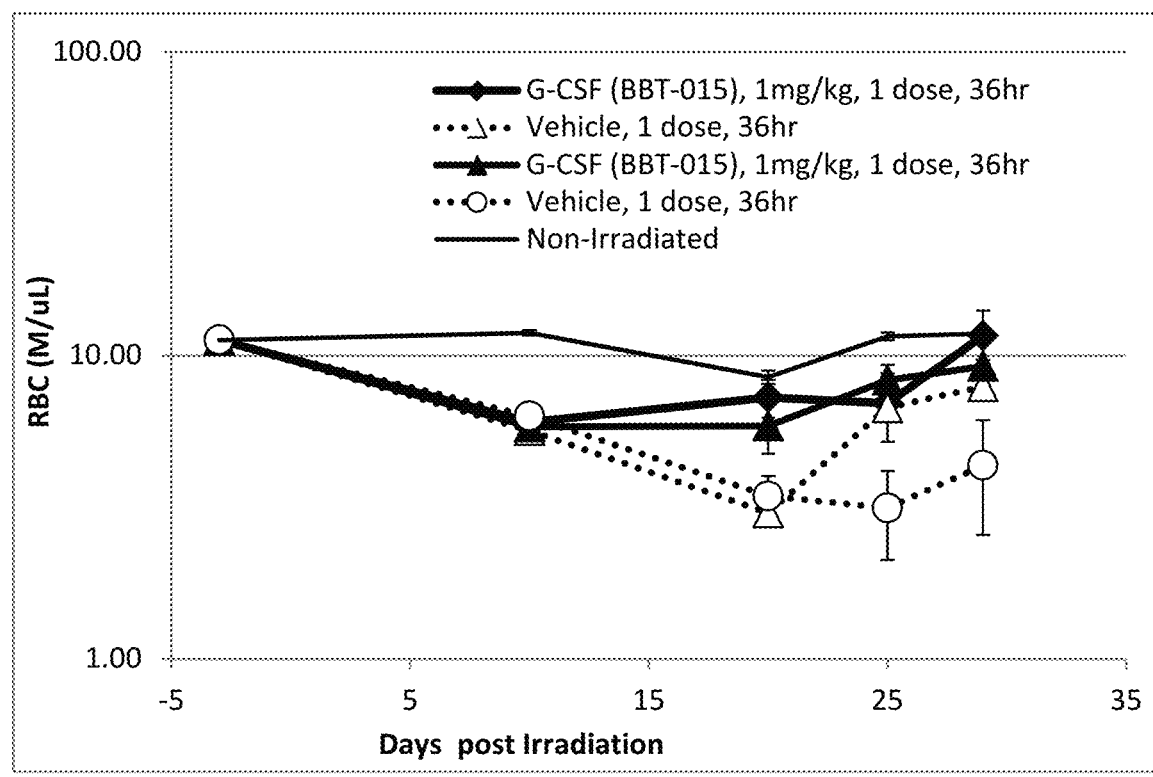
Figure 2E:
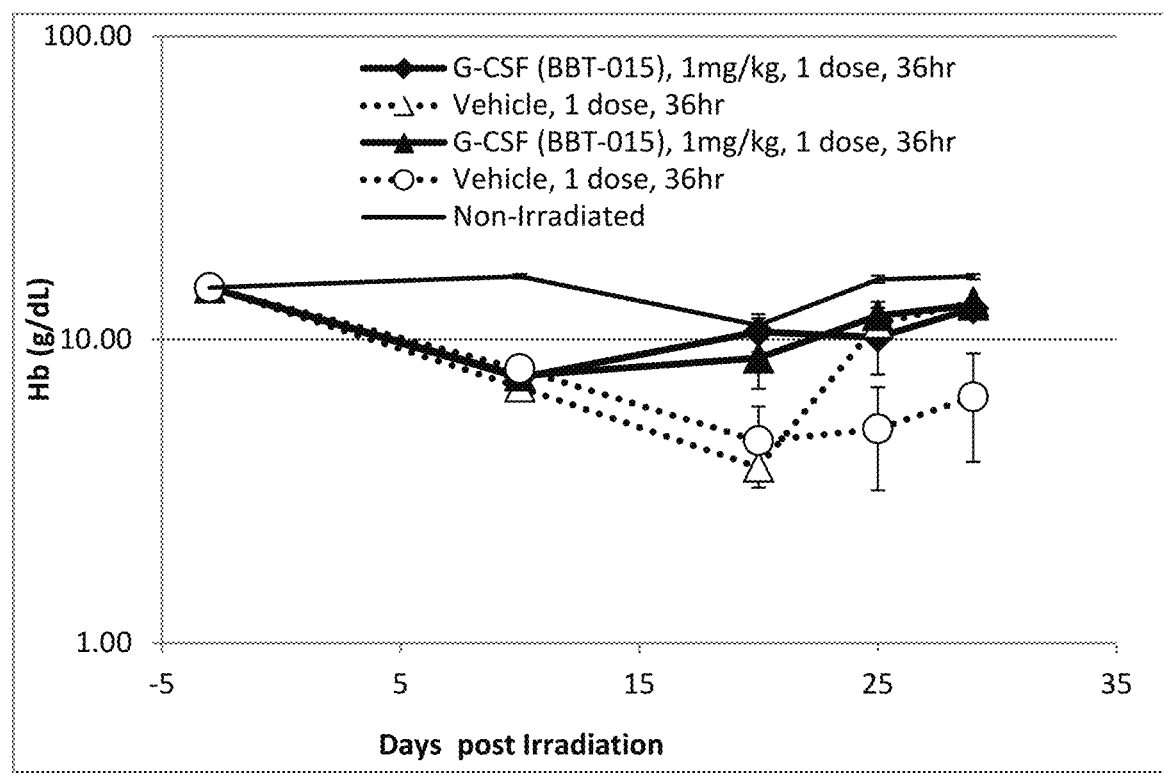
Figure 2F:
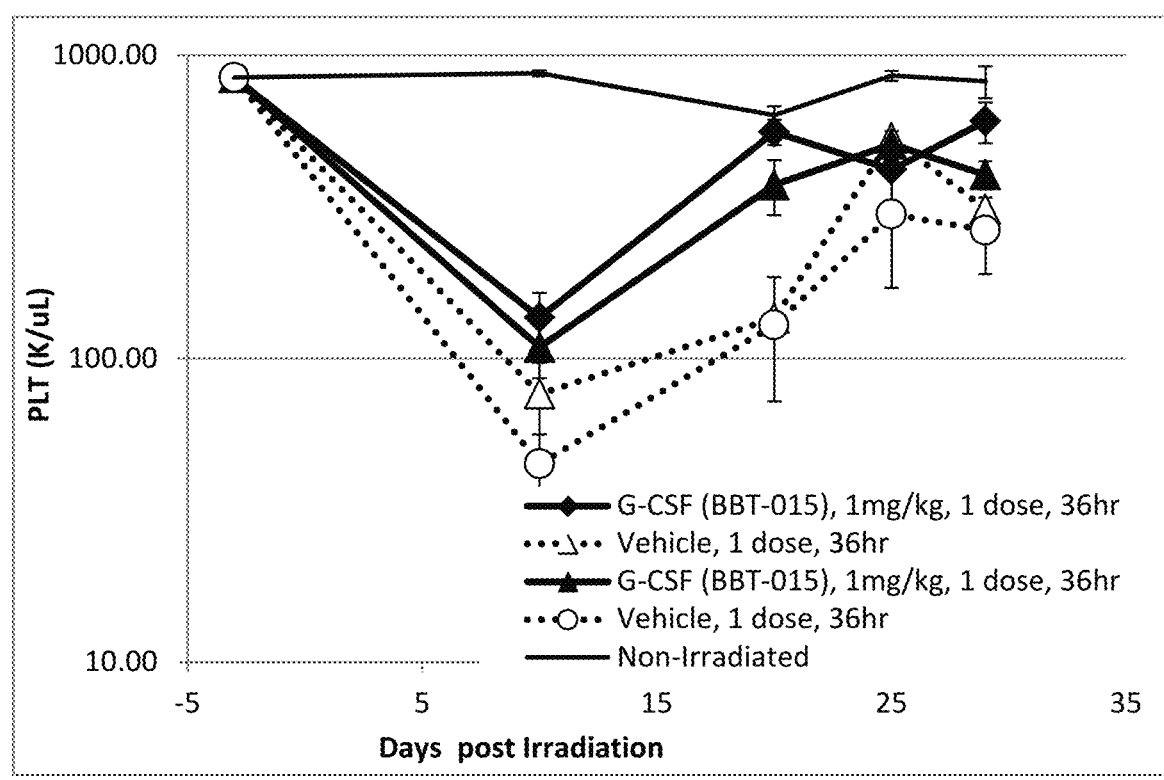
Figure 3A:
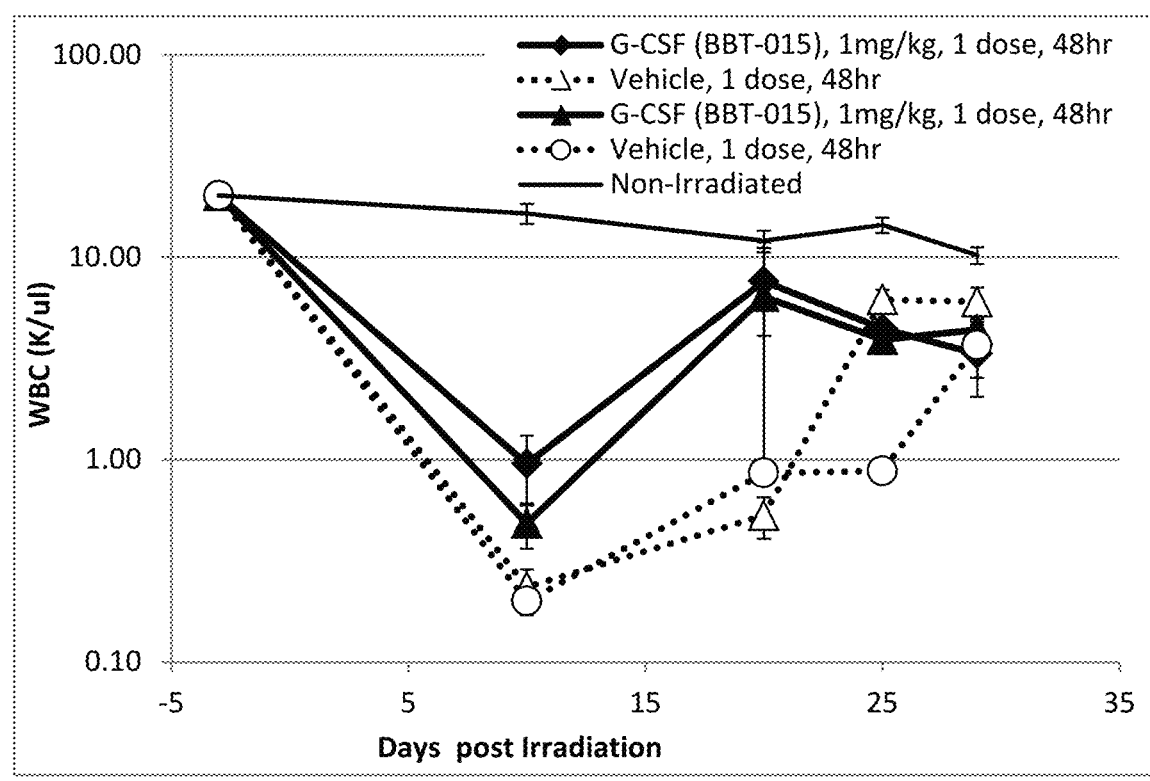
FIGS. 3A-3F shows changes in white blood cells, WBC (FIG. 3A); neutrophils, NE (FIG. 3B); lymphocytes, LY (FIG. 3C); red blood cells, RBC (FIG. 3D); hemoglobin, Hg (FIG. 3E); platelets, PLT (FIG. 3F), overtime in 872 cGy-irradiated mice treated with a single sc injection of vehicle (Control Article) or 1 mg/kg PEG G-CSF analog BBT-015 at 36 h or 48 h post-TBI.
Figure 3B:
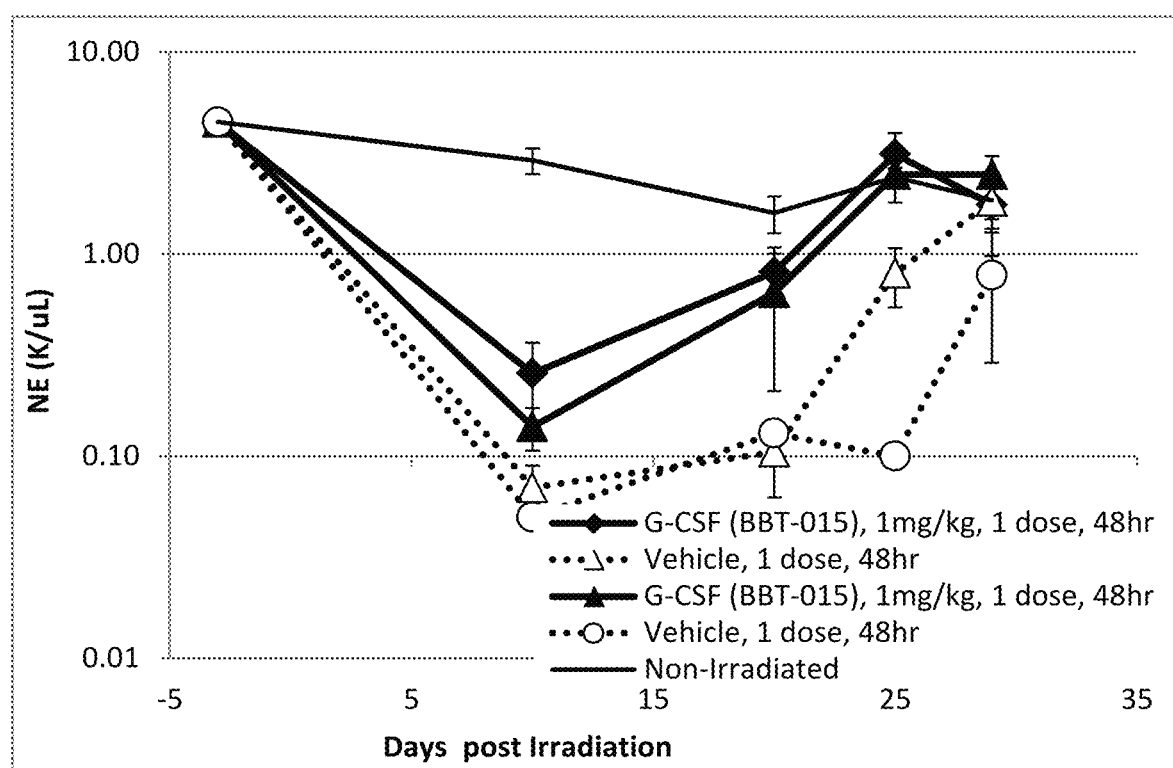
Figure 3C:
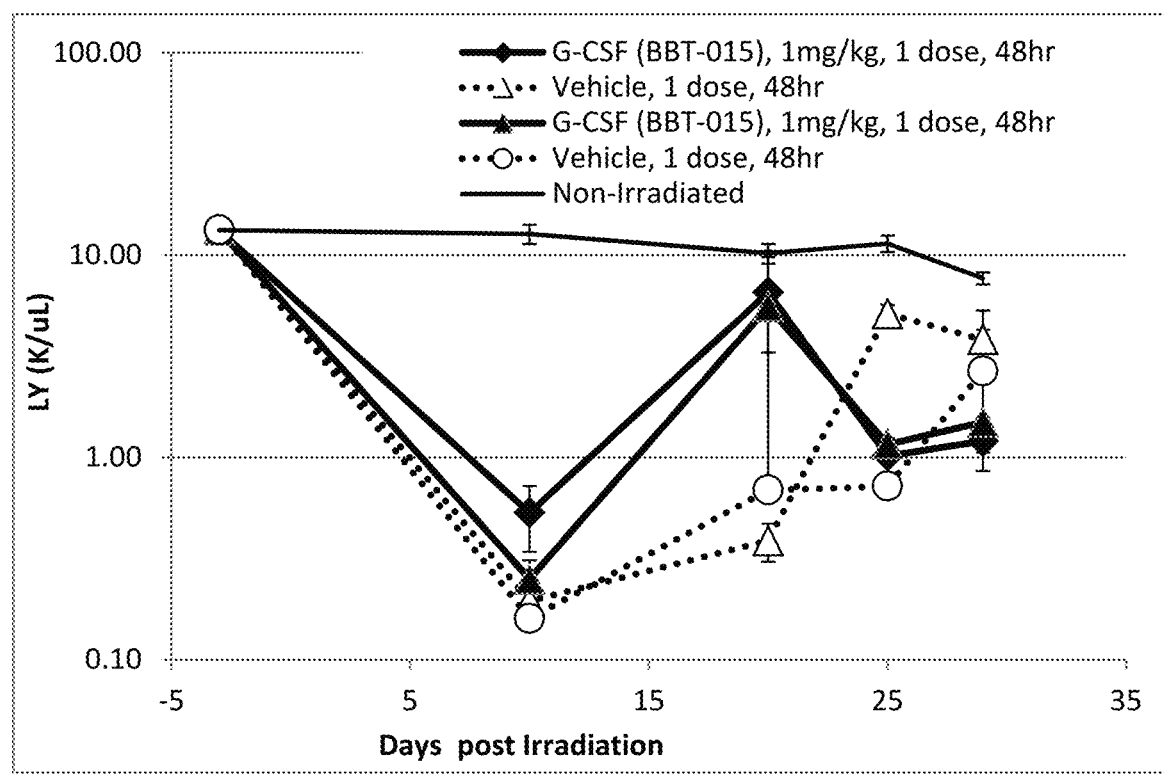
Figure 3D:
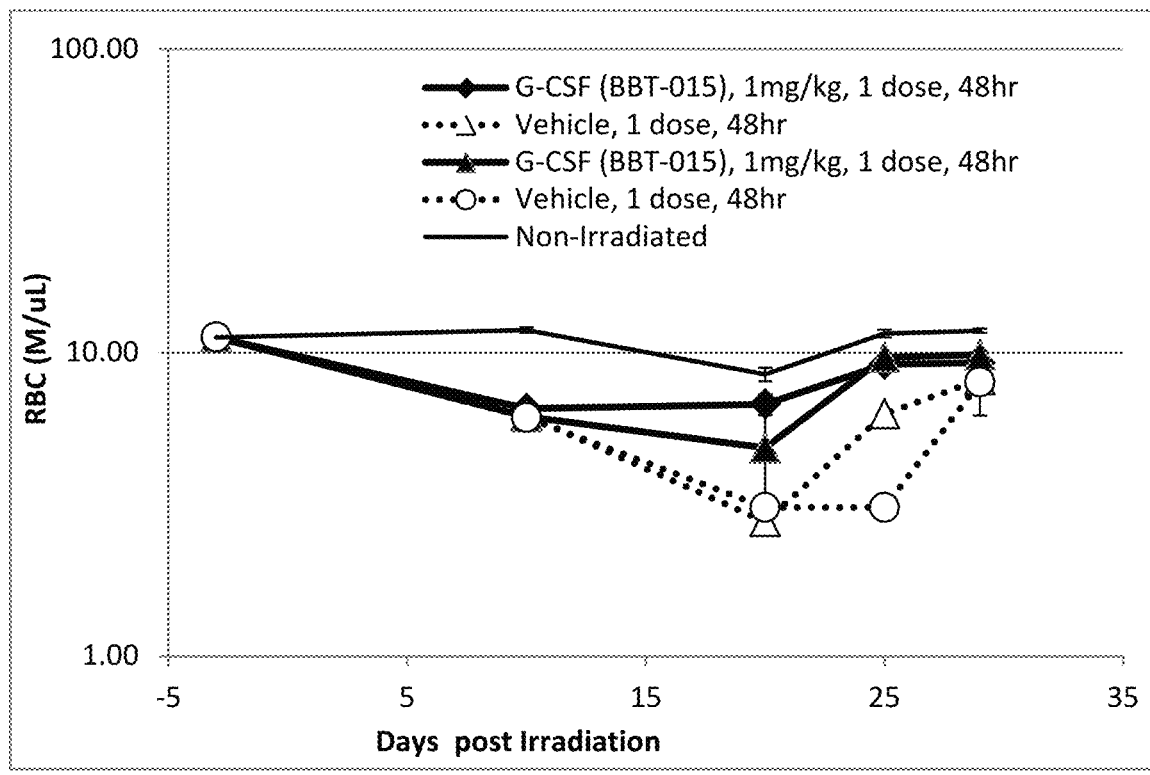
Figure 3E:
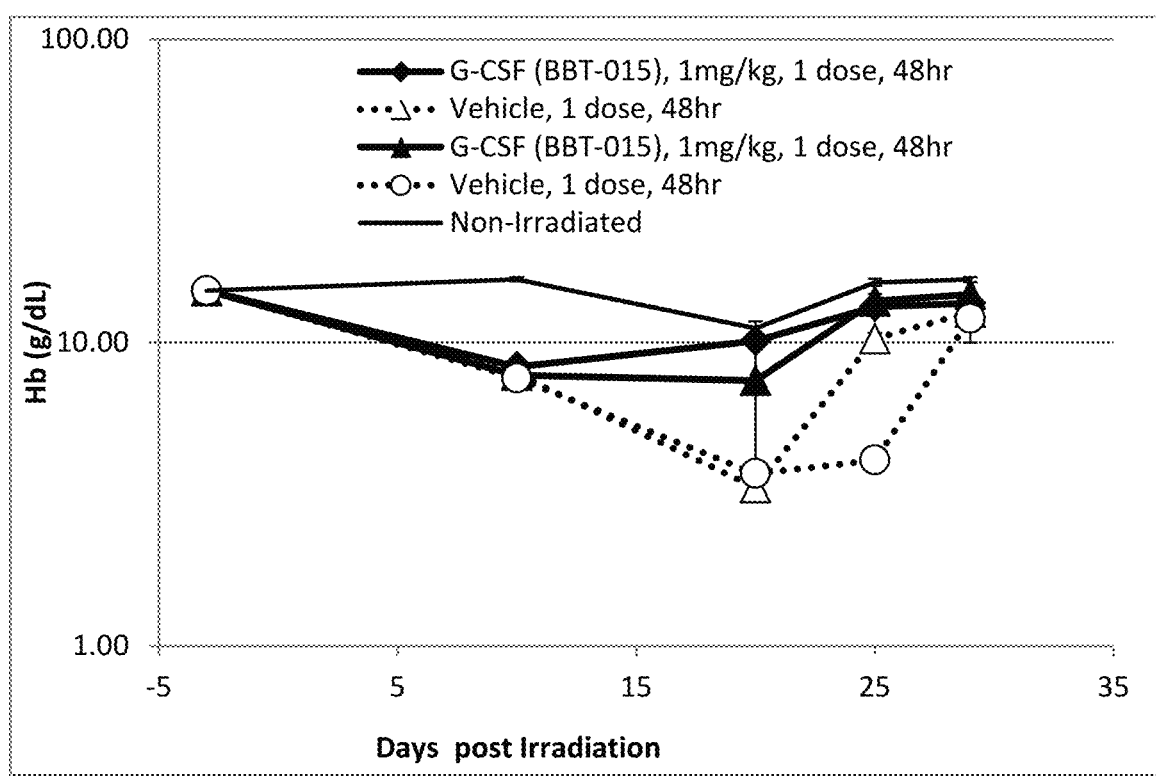
Figure 3F:
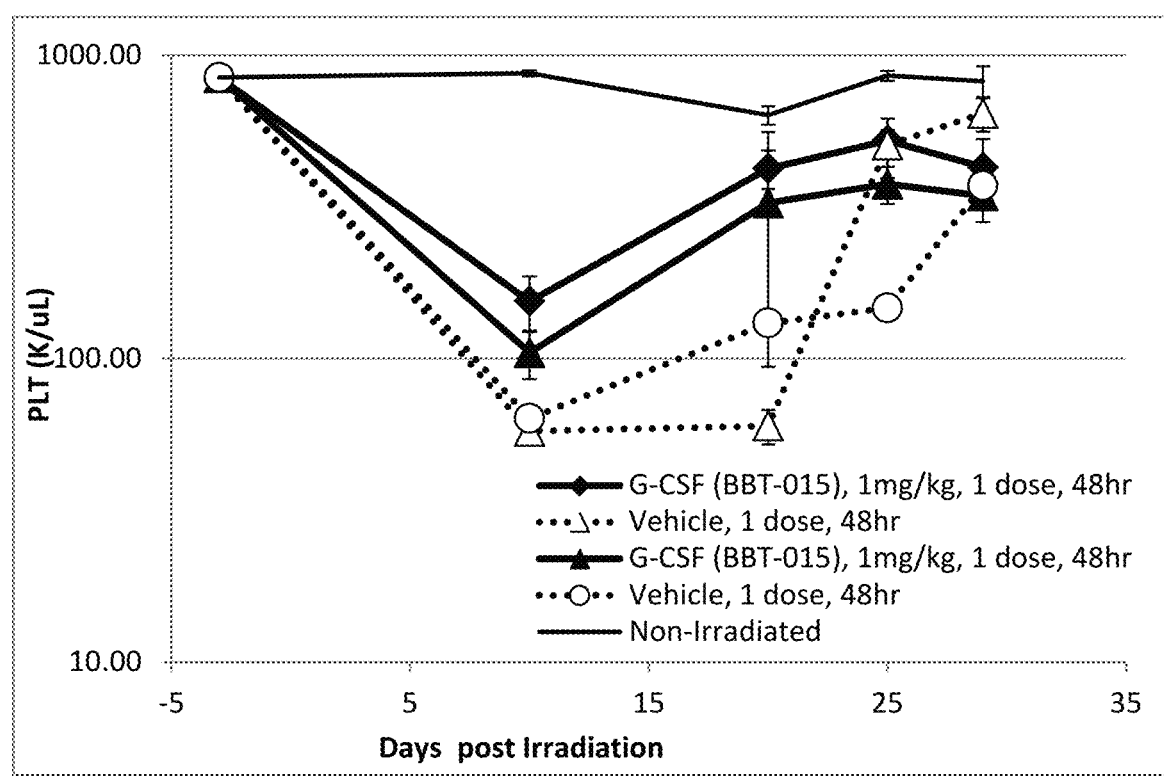

CBC analyses indicated that BBT-015 administration accelerated hematopoietic recovery compared to vehicle, as evidenced by greater numbers of neutrophils, white blood cells, platelets, red blood cells, lymphocytes and hemoglobin levels on day 20 post-TBI compared to vehicle-treated mice (FIGS. 2A-2F and 3A-3F).

Example 4

This examples shows that treating irradiated one year old mice with individual and combinations of Hematopoietic Growth Factors increases 30-day survival compared to vehicle in the Mouse Acute Radiation Syndrome (ARS) Survival Assay.

One year old mice are a model for geriatric humans, which often respond differently to radiation exposure and drugs. One year old mice were exposed to different doses of radiation to construct a radiation dose response curve. The data indicated that one year old mice are less sensitive to radiation exposure than 12 week old mice. The LD50/30 for one year old mice was 959 cGy, compared to 853 cGy for 12 week old mice. The efficacy of single sc injections of PEG-IL-11 analog BBT-059, PEG-G-CSF analog BBT-015, and PEG-murine GM-CSF analog BBT-007 were compared individually and in all possible combinations for improving survival of one year old mice exposed to 10 Gy (estimated LD65/30). Other study details were as described in Example 1 and in Plett et al. (Plett, P A, et al. (2012) Establishing a murine model of the Hematopoietic Syndrome of the Acute Radiation Syndrome. Health Physics 103: 343-355; Plett, P. A., et al. (2014) PEGylated G-CSF (BBT-015), GM-CSF (BBT-007), and IL-11 (BBT-059) analogs enhance survival and hematopoietic cell recovery in a mouse model of the Hematopoietic Syndrome of the Acute Radiation Syndrome. Health Physics Journal 106: 7-20). Mice received one sc injection of the individual test proteins or all possible combinations of the test proteins 24+4/−0 hours post-TBI. Doses of the drugs administered were 1 mg/kg for PEG-G-CSF, 1 mg/kg for PEG-murine GM-CSF, and 0.3 mg/kg for PEG-IL-11. As shown in Table 4, mice treated with vehicle had a 30-day survival rate of 35%, which was lower than the survival rate of mice treated with PEG-IL-11 (80% survival rate), PEG-G-CSF (70% survival rate) or PEG-GM-CSF (55% survival rate). All combinations of the test proteins (PEG-G-CSF+PEG IL-11, PEG-G-CSF+PEG-GM-CSF, PEG GM-CSF+PEG IL-11, and PEG-G-CSF+PEG-GM-CSF+PEG IL-11) also increased 30-day survival more than vehicle solution.

TABLE 4

30-day survival of LD65/30 irradiated one year old mice treated with a single sc injection of PEG IL-11 (0.3 mg/kg), PEG-G-CSF (1 mg/kg) or PEG muGM-CSF (1 mg/kg), or combinations of the proteins. There were 20 mice (10M/10F) per test group.

| Test Group | % 30-d survival | (# survivors/total mice) |
|---|---|---|
| 1. Vehicle | 35 | 7/20 |
| 2. PEG-G-CSF | 70 | 14/20 |
| 3. PEG GM-CSF | 55 | 11/20 |
| 4. PEG IL-11 | 80 | 16/20 |
| 5. PEG-IL-11 + PEG-G-CSF | 80 | 16/20 |
| 6. PEG-IL-11 + PEG-GM-CSF | 75 | 15/20 |
| 7. PEG-GM + PEG-G-CSF | 60 | 12/20 |
| 8. PEG-IL-11 + PEG-GM-CSF + PEG-G-CSF | 65 | 13/20 |

Figure 4A:
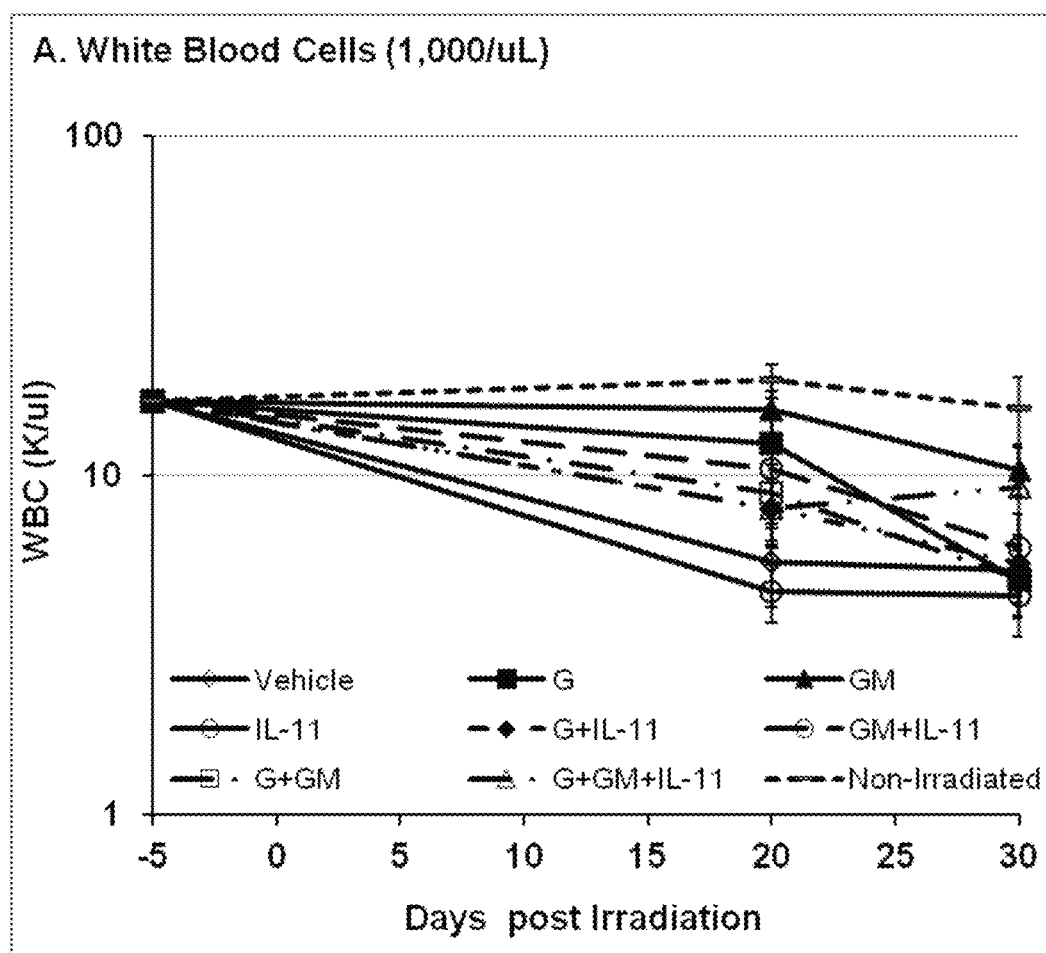
FIGS. 4A-F show the levels of white blood cells, WBC (FIG. 4A); neutrophils, NE (FIG. 4B); lymphocytes, LY (FIG. 4C); red blood cells, RBC (FIG. 4D); hemoglobin, Hg (FIG. 4E); and platelets, PLT (FIG. 4F), on day 20 post LD65/30 irradiation in one year old mice treated with a single sc injection of control article (vehicle), PEG-G-CSF (1 mg/kg), PEG muGM-CSF (1 mg/kg), PEG IL-11 (0.3 mg/kg), and all possible combinations of the proteins 24 h post-irradiation.
Figure 4B:
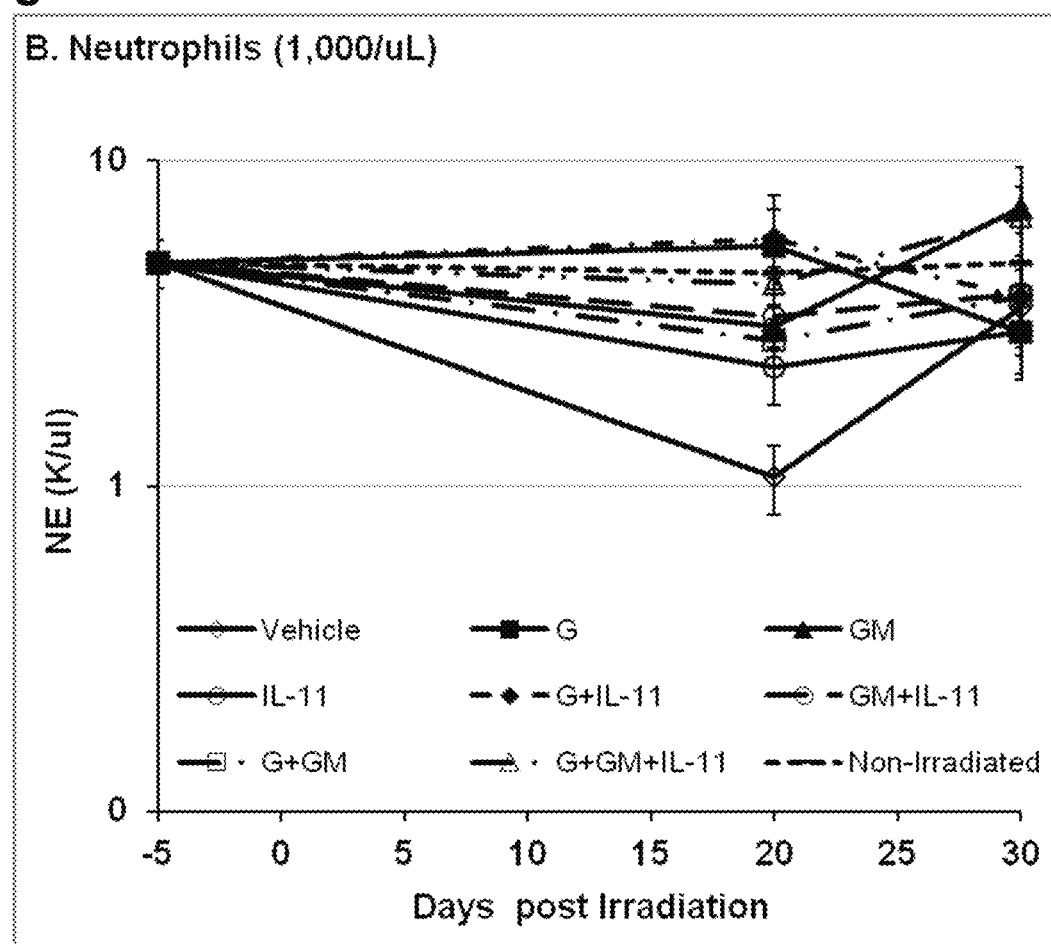
Figure 4C:
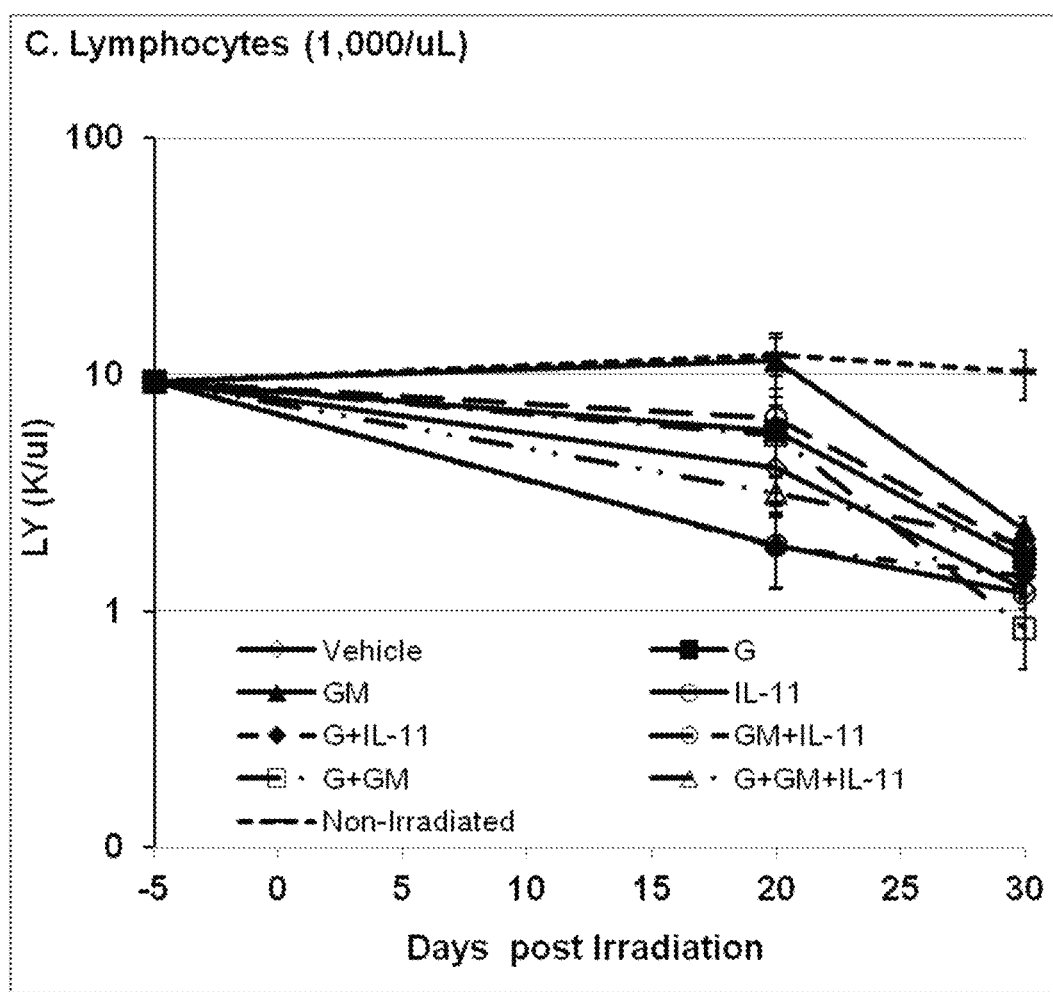
Figure 4D:
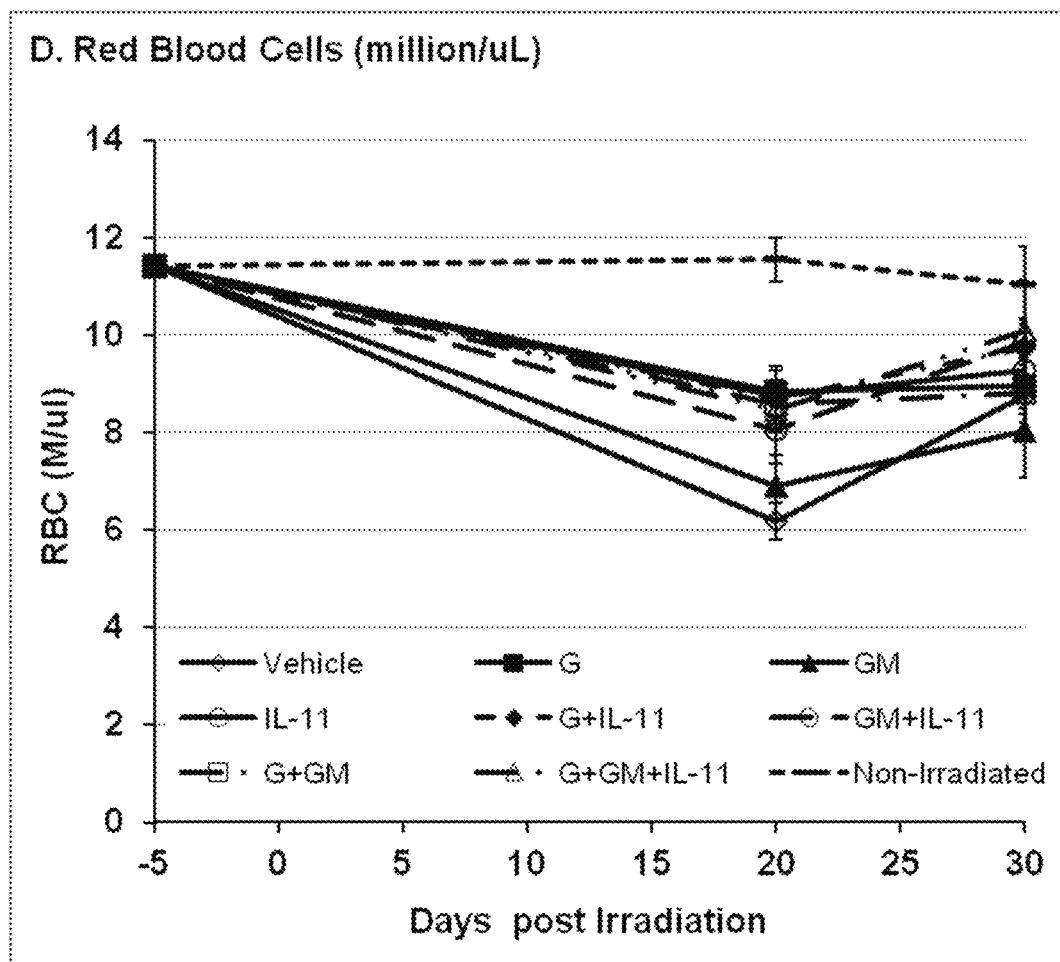
Figure 4E:
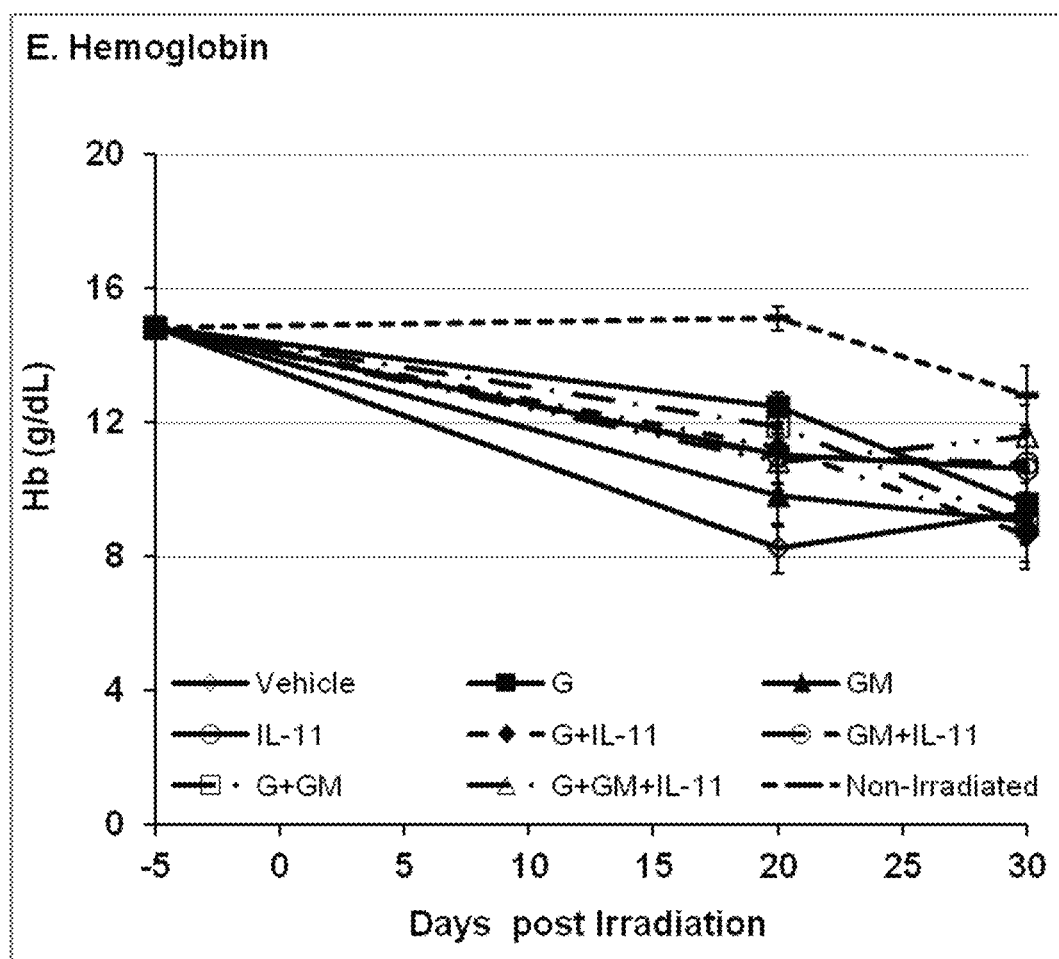
Figure 4F:
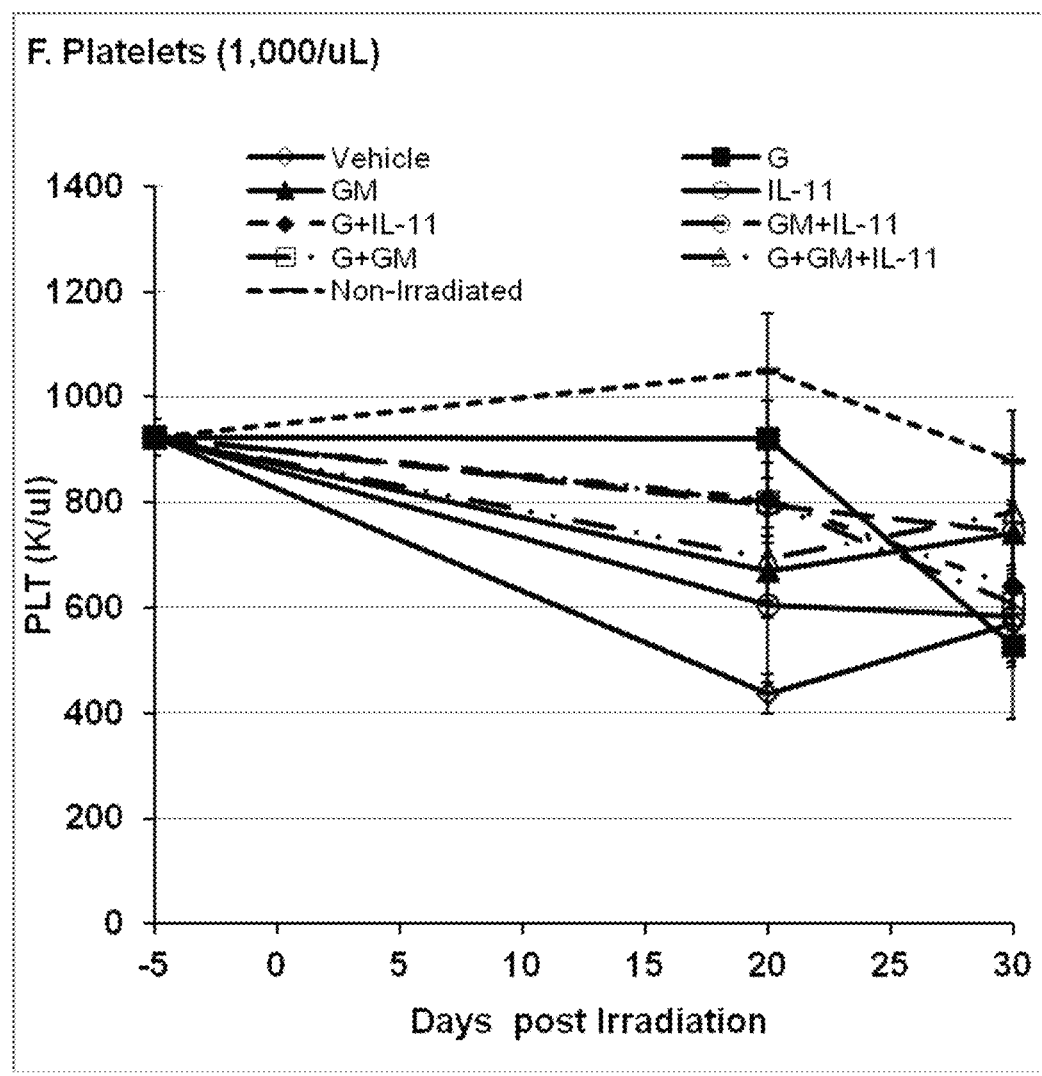

Mice treated with the individual test proteins or combinations of two or three test proteins displayed accelerated hematopoietic recovery compared to vehicle solution, as evidenced by greater numbers of neutrophils, white blood cells, platelets, red blood cells, lymphocytes, and hemoglobin levels on day 20 post-TBI compared to vehicle treated mice (FIGS. 4A-4F).

Example 5

This example shows that treating irradiated mice with one sc administration of PEG-muGM-CSF (1 mg/kg) increases 30-day survival compared to vehicle in the Mouse Acute Radiation Syndrome Survival Assay.

Figure 5A:
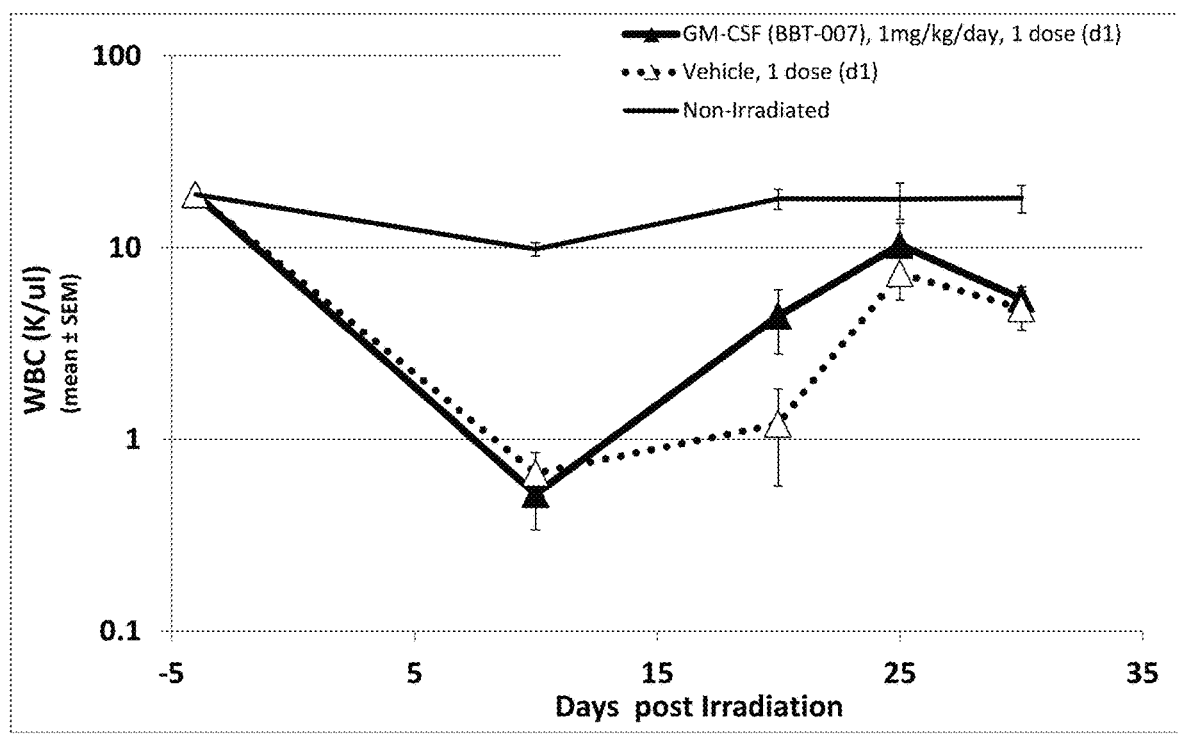
FIGS. 5A-5F show changes in white blood cells, WBC (FIG. 5A); neutrophils, NE (FIG. 5B); lymphocytes, LY (FIG. 5C); red blood cells, RBC (FIG. 5D); hemoglobin, Hg (FIG. 5E); platelets, PLT (FIG. 5F), over time in irradiated mice treated with a single sc injection of vehicle (Control Article) or 1 mg/kg PEG muGM-CSF analog BBT-007 at 24 h post-TBI. Data are combined from mice exposed to 853 cGy and 872 cGy.
Figure 5B:
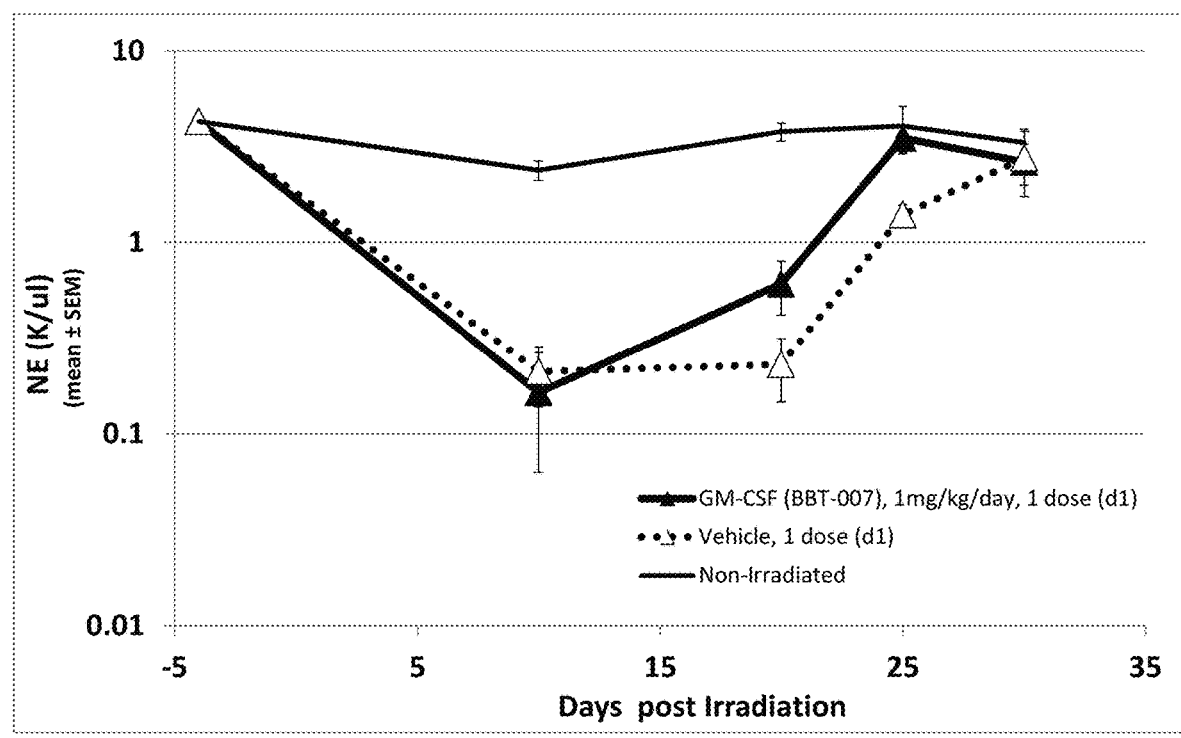
Figure 5C:
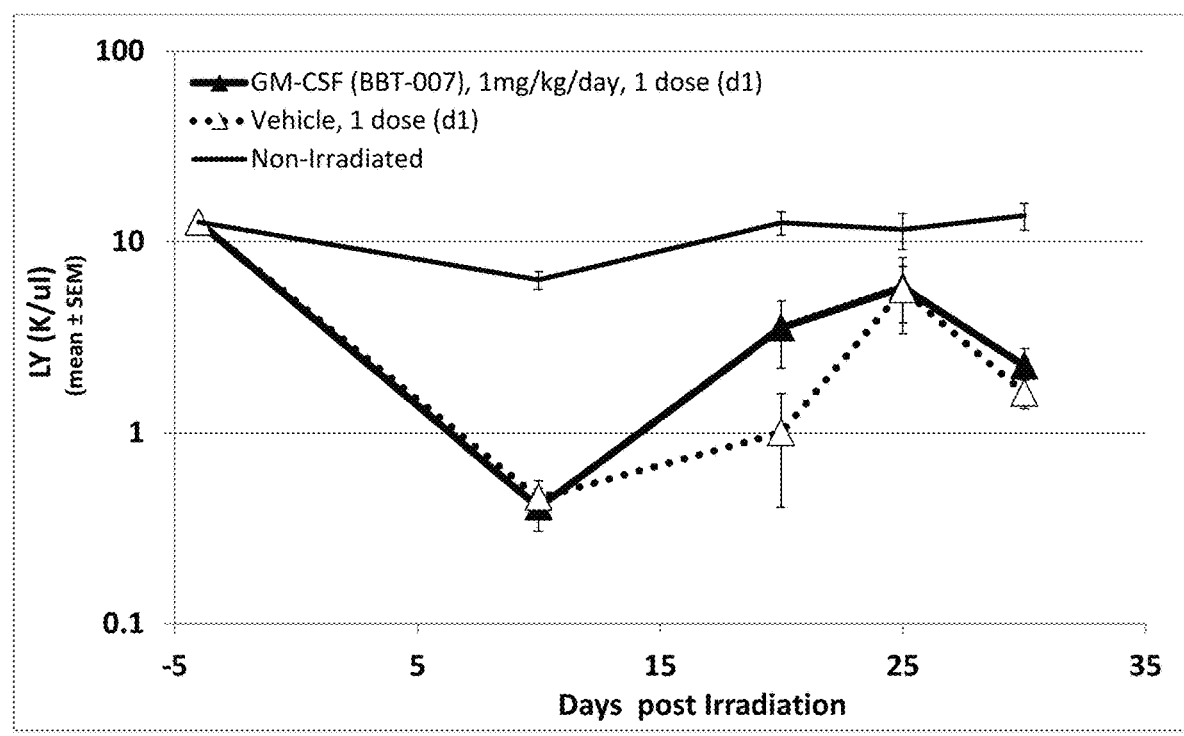
Figure 5D:
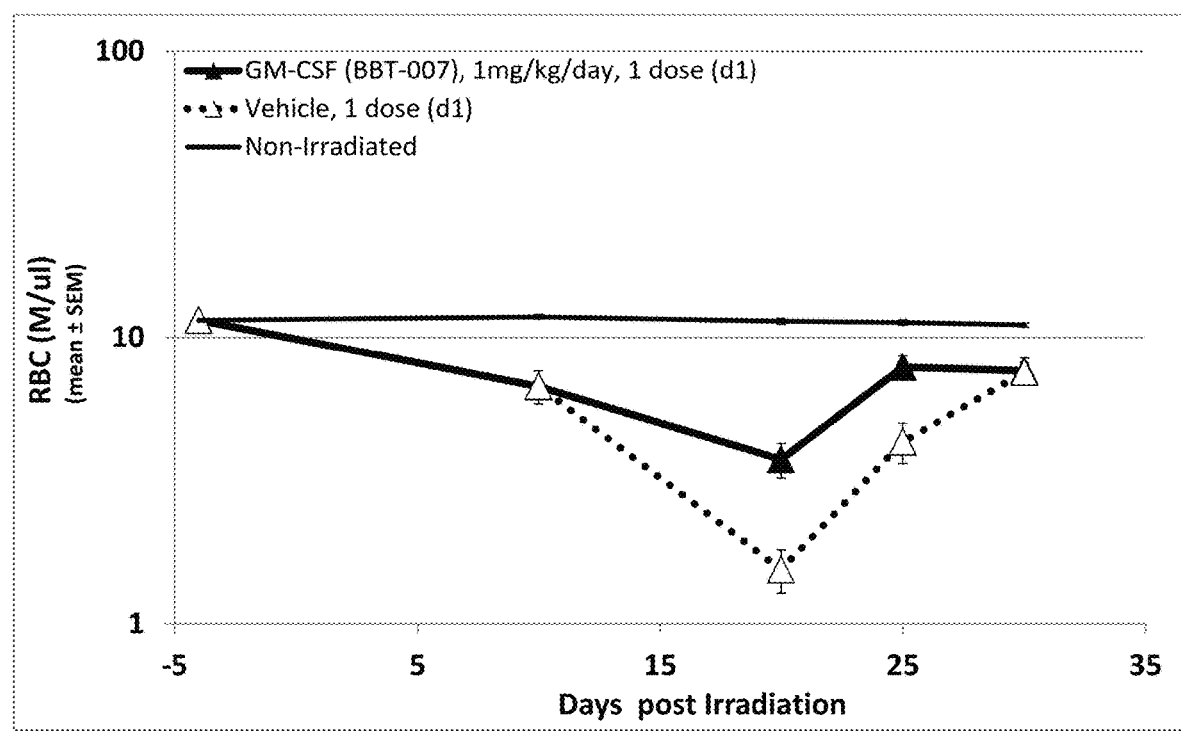
Figure 5E:
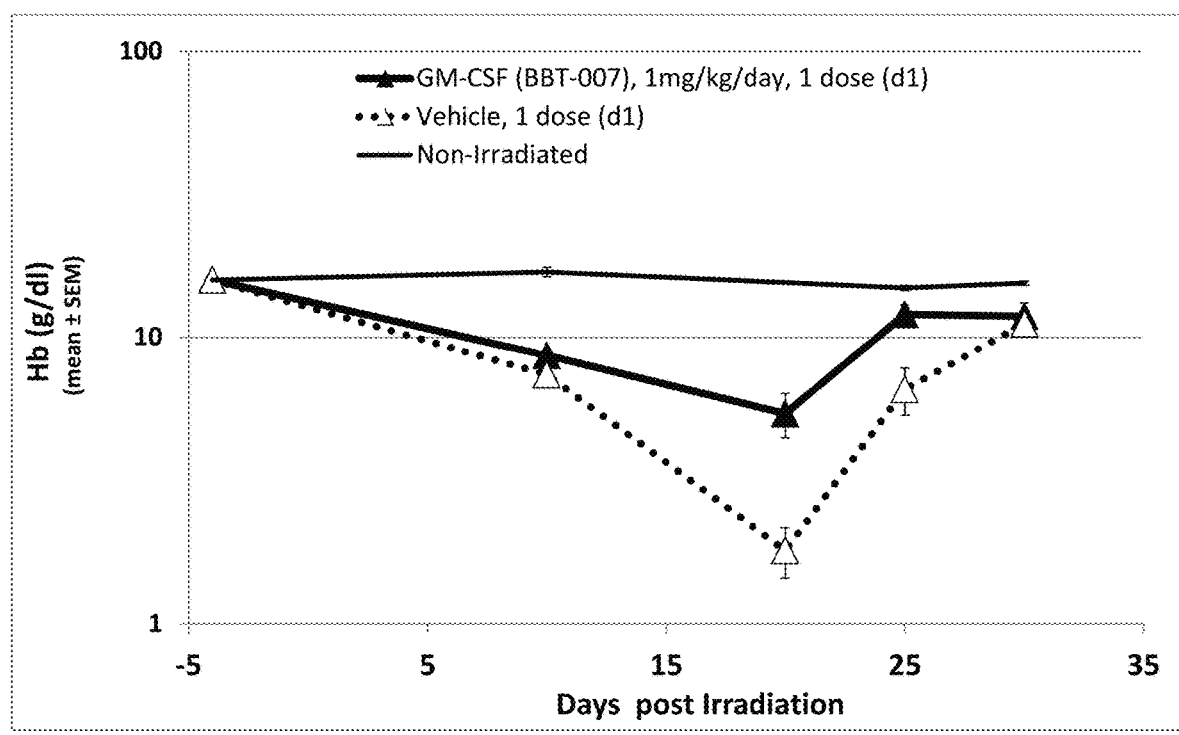
Figure 5F:
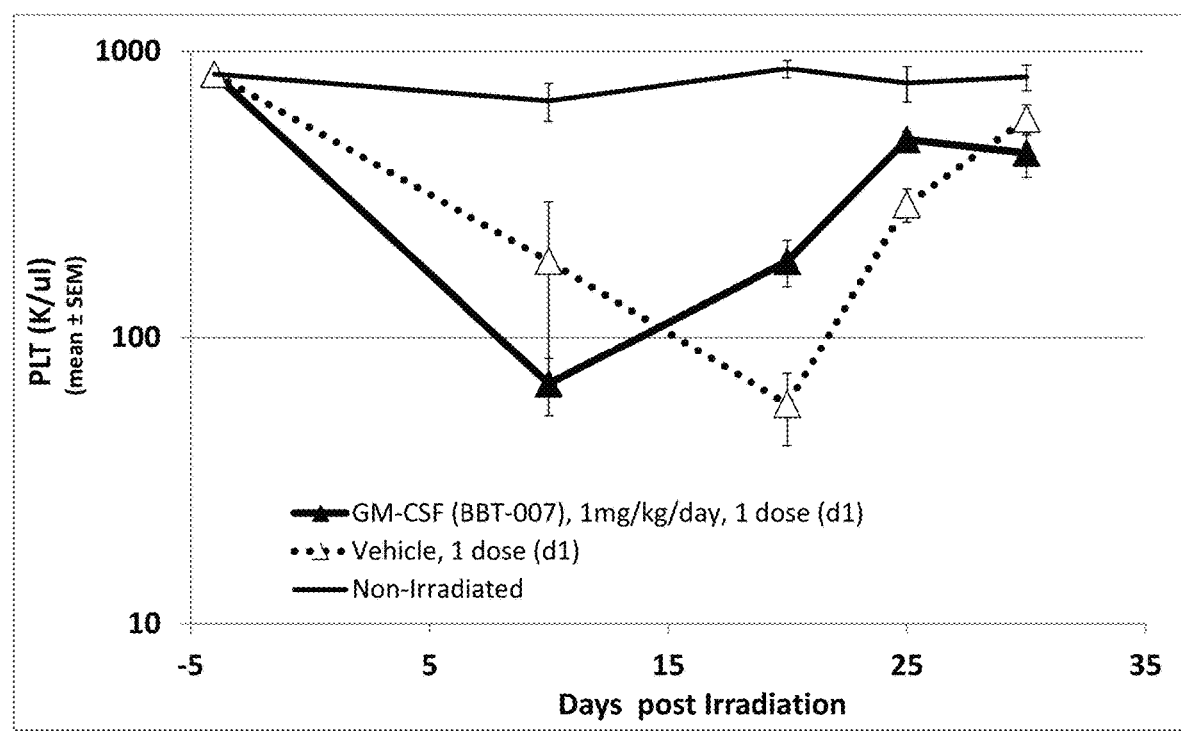

This study was performed as described in Example 1 except that 10-12 week old mice were exposed to 853 cGy (estimated LD50/30) or 872 cGy (estimated LD70/30) radiation doses and then treated with a single sc injection of PEG-murine GM-CSF analog BBT-007 (1 mg/kg) 24+4/−0 h post-TBI. Control mice received a single sc injection of vehicle solution (20 mM sodium acetate, pH 4.5, 140 mM NaCl) 24 h post-TBI. As shown in Table 5, 85% of mice exposed to 853 cGy and treated once with PEG-muGM-CSF at 24 h post-TBI were still alive at 30 days, compared to 60% of vehicle-treated mice. At the higher 872 cGy radiation dose, 70% of mice treated once with PEG-muGM-CSF at 24 h post-TBI were still alive at 30 days, compared to 10% of vehicle-treated mice. Pooled data from these two radiation doses indicate that significantly more mice treated with PEG-muGM-CSF (77.5%) survived 30 days than did mice treated with vehicle solution (35%) (p=0.0007). In contrast to these findings with a long-acting GM-CSF analog, a single sc injection of muGM-CSF does not improve 30-day survival of lethally irradiated mice (Neta R. and Oppenheim J J (1988) Cytokines in radiation injury. Blood 72: 1093-1095). Mice treated with PEG-muGM-CSF displayed accelerated hematopoietic recovery vs vehicle, as evidenced by greater numbers of neutrophils, white blood cells, platelets, lymphocytes, red blood cells and hemoglobin levels on day 20 post-TBI compared to vehicle-treated mice (FIGS. 5A-5F).

TABLE 5

30-day survival of mice exposed to 853 cGy or 872 cGy TBI and treated once with a single sc injection of PEG muGM-CSF (1 mg/kg) at 24 h post-TBI. There were 20 mice (10M/10F) per test group.

| Test Group | Radiation dose | % 30-d survival | (# survivors/total mice) |
|---|---|---|---|
| 1. Vehicle | 853 cGy | 60% | 12/20 |
| 2. PEG-muGM-CSF | 853 cGy | 85% | 17/20 |
| 3. Vehicle | 872 cGy | 10% | 2/20 |
| 4. PEG-muGM-CSF | 872 cGy | 70% | 14/20 |

Example 6

This example shows that treating irradiated mice with one sc administration of PEG-IL-11 (0.3 mg/kg) increases 30-day survival compared to non-PEGylated IL-11 and vehicle in the Mouse Acute Radiation Syndrome (ARS) Survival Assay.

This study was performed as described in Example 1 except that 10 to 12 week-old mice were exposed to 927 cGy (estimated LD95/30) radiation dose and then treated once with a single sc injection of PEG-IL-11 analog BBT-059 (0.3 mg/kg), non-PEGylated IL-11 (oprevlekin, Neumega, Wyeth), or vehicle (10 mM sodium phosphate, 4% mannitol, 1% sucrose, pH 6.2) at 24+4/−0 h post-TBI. PEG-IL-11 was formulated in vehicle solution. As shown in Table 6, significantly more mice treated with PEG-IL-11 survived 30 days (60%) than did mice treated with non-PEGylated IL-11 (15%) or vehicle solution (10%).

TABLE 6

30-day survival of mice exposed to 927 cGy (estimated LD95/30) TBI and treated once with a single sc injection of PEG-IL-11 (0.3 mg/kg), non-PEGylated IL-11 (oprevlekin, Neumega, 0.3 mg/kg), or vehicle (10 mM sodium phosphate, 4% mannitol, 1% sucrose pH 6.2). There were 20 mice (10M/10F) per test group.

| Test Group | % 30-d survival | (# survivors/total mice) |
|---|---|---|
| 1. Vehicle | 10% | 2/20 |
| 2. IL-11 (non-PEGylated) | 15% | 3/20 |
| 3. PEG-IL-11 | 65% | 12/20 |

Example 7

This Example shows that treating lethally irradiated rats with a representative ACE inhibitor, Lisinopril, prevents lung and kidney damage (and associated morbidity and mortality) caused by radiation exposure and thus increases survival following radiation exposure.

The data further show that treating irradiated rats with HGFs may worsen radiation-induced lung and kidney damage and increase associated morbidity and mortality. The data further show that treating irradiated rats with the representative ACE inhibitor Lisinopril prevents the lung and kidney damage, and the increased morbidity and mortality caused by radiation exposure and HGF treatment, and thus increases survival following radiation exposure in animals exposed to radiation and treated with an HGF.

The rat 13 Gy "leg-out total body irradiation model" was used to study the effects of the ACE inhibitor Lisinopril and HGFs on radiation-induced injury to multiple organs, and in particular to radiation-induced damage to lung and kidney. Female WAG/RijCmcr rats were irradiated with 13 Gy at 12 weeks of age when they weighed ~150-170 gm. Briefly, animals were immobilized in a plexiglass jig to avoid anesthetic. One hind leg was shielded with a one-quarter inch thick lead block. Shielding one leg from radiation exposure is sufficient to prevent death from hematopoietic failure during the following 40 days. Thus, this model allows later effects of acute, high dose radiation exposure such as injury to the heart, lung, and kidney to be studied. Radiation-induced injury to heart, lung and kidney typically does not manifest until days 40-150 post-TBI, and are thus classified as delayed effects of acute radiation exposure (DEARE). The TBI was delivered posterior to anterior as described (Medhora M, et al. (2014) Model development and use of ACE inhibitors for preclinical mitigation of radiation-induced injury to multiple organs. Rad Res. 182(5):545-555; Moulder J E, Cohen E P, Fish B L. (2014) Mitigation of experimental radiation nephropathy by renin-equivalent doses of angiotensin converting enzyme inhibitors. Int J Radiat Biol. 90(9):762-768) at a rate of 1.75 Gy/minute using a XRAD 320 KV orthovoltage x-ray system. The x-ray system was operated at 320 kVp and 13 mAs with a half value layer of 1.4 mm Cu. During the irradiation, each rat was confined in a separate chamber in a plastic jig, which allowed irradiation of 2 rats simultaneously. The chambers were placed on a plane perpendicular to the beam direction with distance from source to the midline of rats to be set at 33.5 cm. Collimator jaws were used to define a radiation field large enough to cover both chambers with adequate margin (at least 2 cm). Irradiated rats were given supportive care between days 2 to 14 post-TBI to mitigate acute gastrointestinal injury. This supportive care consisted of sc injections of saline (40 mL/kg/day) from days 3 to 7 post-TBI and the antibiotic enrofloxacin (10 mg/kg/day), given orally in the drinking water from days 2 to 14 post-TBI.

This study comprised four test groups, each consisting of 12 rats (Table 7). Rats received a single sc injection of vehicle solution (10 mM sodium phosphate, 4% mannitol, 1% sucrose pH 6.2) or an HGF triple combination (TC) at 24+4/−0 hr post-irradiation. The TC consisted of a combination of PEG-G-CSF analog BBT-015 (0.55 mg/kg), PEG-muGM-CSF analog BBT-007 (0.55 mg/kg) and PEG IL-11 analog BBT-059 (0.165 mg/kg) formulated in vehicle solution. Groups 2 and 4 rats received Lisinopril in their drinking water (40 mg/mL) beginning on day 7 post-irradiation and continuing until day 150 post-irradiation. This dose of Lisinopril (~24 mg/m$^2$/day) is equivalent to an approved human dose on a mg/m/day basis. The equivalent effective dose in rats typically is approximately 6.2× the effective equivalent human dose. The equivalent effective dose in mice typically is approximately 12.4× the effective equivalent human dose. The control for Groups 2 and 4 was drinking water that did not contain Lisinopril. Morbidity and survival of the animals were measured over time. Rats were euthanized if their body condition reached IACUC criteria for euthanasia or if their blood urea nitrogen (BUN) was measured at or above 120 mg/mL, which is an indicator if severe kidney damage. Euthanized animals are classified as non-survivors. Death prior to day 40 in this model typically occurs as a result of hematopoietic failure (H-ARS) or gastrointestinal injury (GI-ARS). Death between days 40 and 90 typically occurs as a result of lung damage, particularly pneumonitis. Death between days 90 and 150 typically occurs as a result of kidney damage (nephropathy). Morbidity at Day 40, 90 and 150 were chosen as representative times for death due to H-ARS, lung damage, and a combination of lung damage and kidney damage, respectively. Survival results from this study (Table 7) showed that 100% of the rats in all treatment groups survived to day 40, indicating no deaths from H-ARS or GI-ARS, as expected for the one-leg out TBI model with supportive care. On day 90, survival was significantly higher in rats treated with TC plus Lisinopril (100%) compared to rats treated with TC only (42% survival; p<0.006). Similarly, day 90 survival was higher in rats treated with Vehicle on day 1 plus Lisinopril (100% survival), compared to rats treated with Vehicle only (67% survival). These data indicate that day 90 mortality, which primarily reflects death from lung damage such as pneumonitis, was lower in animals treated with Lisinopril compared to animals not treated with Lisinopril. Day 90 mortality also was higher in rats treated with TC compared to rats treated with Vehicle, suggesting that TC administration might worsen lung damage following irradiation. The data indicate that radiation-induced lung damage, and any potentially increased lung damage caused by treating irradiated rats with TC could be prevented by treating rats with Lisinopril from days 7 to 150. Day-90 survival was slightly higher in animals treated with TC plus Lisinopril compared to animals treated with Vehicle plus Lisinopril. On Day 150, survival was significantly higher in rats treated with TC plus Lisinopril (100% survival) compared to TC only (0% survival; p<0.05). Day 150 survival also was significantly higher in rats treated with Vehicle plus Lisinopril (92% survival) compared to Vehicle only (0% survival; p<0.05). These data indicate that day 150 mortality, which reflects cumulative mortality caused by radiation-induced lung damage and kidney damage, was significantly less in animals treated with Lisinopril compared to animals not treated with Lisinopril. Thus, the data indicate that both radiation-induced lung and kidney damage could be prevented by treating rats with Lisinopril from days 7 to 150.

TABLE 7

Survival up to 150 days in rats exposed to 13 Gy and treated on day 1 post-irradiation with TC or Vehicle, and on Day 7 to Day 150 with Lisinopril or no Lisinopril. There were 12 rats per treatment group.

| Test group | Survival (%) | | |
|---|---|---|---|
| | Day 40 | Day 90 | Day 150 |
| 1. TC | 100 | 42 | 0 |
| 2. TC + Lisinopril | 100 | 100 | 100 |
| 3. Vehicle | 100 | 67 | 0 |
| 4. Vehicle + Lisinopril | 100 | 92 | 92 |

Blood urea nitrogen (BUN) measurements were made as a separate measure of kidney damage in surviving animals on Days 90, 120 and 150 (Table 8). BUN measurements are a commonly used measure of kidney function, with higher BUN numbers indicating greater kidney damage. Normal rat BUN measurements for non-irradiated rats are in the 17-22 mg/dL range. Rats were euthanized if BUN measurements were at or above 120 mg/dL. As shown in Table 8, BUN measurements increased progressively from day 90 to day 150 in irradiated rats that did not receive Lisinopril (Groups 1 and 3), demonstrating that acute radiation exposure induces progressive increases in kidney damage over time. BUN measurements were significantly lower on days 90, 120 and 150 in rats treated with Lisinopril (Groups 2 and 4) compared to rats not treated with Lisinopril (Groups 1 and 3), indicating that Lisinopril prevents kidney damage caused by acute radiation exposure in rats.

TABLE 8

Renal injury, as measured by BUN, in rats exposed to 13 Gy and treated on day 1 post-irradiation with TC or Vehicle, and on Day 7 to Day 150 with Lisinopril or no Lisinopril. Lisinopril was provided in the drinking water. BUN numbers are medians for surviving animals. The $20^{th}$ percentile and 80% percentile BUN measurements for each test group are shown in parentheses. There were 12 rats per treatment group.

| Test group | BUN (mg/dL) | | |
|---|---|---|---|
| | Day 90 | Day 120 | Day 150 |
| 1. TC | 55 (49-60) | 70 (59-120) | 120 (120-120) |
| 2. TC + Lisinopril | 22 (19-27) | 31 (25-34) * | 34 (25-40) ** |
| 3. Vehicle | 60 (55-63) | 77 (65-92) | 120 (120-120) |
| 4. Vehicle + Lisinopril | 25 18-33) | 23 (20-24) * | 25 (22-27) ** |

*, ** statistically different by Mann Whitney U test between the groups.

Example 8

This Example shows that treating irradiated rats with a representative ACE inhibitor, Lisinopril, prevents heart damage caused by radiation exposure.

The rat 13 Gy "leg-out total body irradiation model" was used for this study. Female WAG/RijCmcr rats were irradiated with 13 Gy at 12 weeks of age when they weighed ~150-170 gm, as described in Example 6. One group of rats was treated with Lisinopril (40 mg/mL) in the drinking water from day 7 post irradiation to day 150 post-irradiation. A Vehicle group was treated with drinking water that did not contain Lisinopril. Non-irradiated rats (0 Gy) served as controls. On day 50, the rats were anesthetized with isoflurane (2%) and transthoracic echocardiography was performed. Measurements were obtained by an investigator who was blinded to the treatment groups. Animals were studied in the left lateral decubitus position and data was recorded with a Vivid 7 echocardiographic system (General Electric, Waukesha, WI). The following heart parameters were analyzed and shown to be significantly different between control (0 Gy) animals and animals exposed to 13 Gy irradiation and treated with Vehicle: Left Ventricular Internal Dimension, End-Diastolic Volume, Stroke volume, Left Ventricle Posterior Wall diastole, Left Ventricle Internal Diameter systole, End Systolic Volume, Left Ventricle Mass, Ejection Time, Isovolumic Relaxation Time, (Table 9). Treating irradiated rats with Lisinopril on days 7 to 50 prevented or reduced radiation-induced changes to the following heart parameters: left ventricular internal dimension (diastole), end-diastolic volume, stroke volume, cardiac output, left ventricle posterior wall diastole, left ventricle internal diameter systole, end systolic volume, left ventricle mass, ejection time, isovolumic relaxation time, and early diastolic mitral annulus velocity.

TABLE 9

Heart injury, as measured by various heart parameters, in rats exposed to 13 Gy and treated on Day 7 to Day 50 with Lisinopril or no Lisinopril (Vehicle). Lisinopril was provided in the drinking water. There were 8 rats per treatment group. Control animals (0 Gy) were not exposed to radiation. Data are the means ± standard deviations for each group. Asterisks (*) indicate values that are significantly different ($p < 0.05$) from Control (0 Gy) animals by one-way ANOVA.

| Heart Parameter | Control (0 Gy) | Irradiated (13 Gy (leg-out) + Vehicle | Irradiated (13 Gy (leg-out) + lisinopril |
|---|---|---|---|
| Left Ventricular Internal Dimension (diastole) (cm) | 0.630 ± 0.02 | 0.485 ± 0.14 * | 0.57 ± 0.17 |
| End-Diastolic Volume (mL) | 0.578 ± 0.05 | 0.330 ± 0.22 * | 0.585 ± 0.08 |
| Stroke volume (mL) | 0.501 ± 0.05 | 0.290 ± 0.19 * | 0.460 ± 0.06 |
| Cardiac Output (mL/minute) | 196.1 ± 26.2 | 116.9 ± 78.2 * | 170.1 ± 36.4 * |
| Left Ventricle Posterior Wall diastole (cm) | 0.143 ± 0.02 | 0.164 ± 0.03 * | 0.109 ± 0.01 |
| Left Ventricle Internal Diameter systole (cm) | 0.300 ± 0.05 | 0.221 ± 0.09 * | 0.364 ± 0.03 |
| End Systolic Volume (mL) | 0.0735 ± 0.03 | 0.0400 ± 0.04 * | 0.125 ± 0.04 |
| Left Ventricle Mass (grams) | 1.030 ± 0.06 | 0.944 ± 0.11 * | 0.919 ± 0.04 |
| Ejection Time (meter · second) | 62.4 ± 4.4 | 69.0 ± 6.43 * | 67.6 ± 7.99 * |
| Isovolumic Relaxation Time (meter · second)ok | 13.8 ± 1.92 | 21.0 ± 8.41 * | 15.6 ± 2.61 |

Example 9

This example shows that PEG IL-11 treatment improves immune reconstitution in H-ARS survivors.

The effects of the PEG-HGF on immune reconstitution in H-ARS survivors from Example 1 and Example 10 at 1 year post-LD65/30 (872 cGy) and LD95/30 (927 cGy) irradiation was studied. Cell density (# cells/gm tissue) in spleen and lymph nodes of H-ARS survivors (n=29), regardless of treatment group, was 30% of that from non-irradiated age-matched controls (n=5, p<0.009). Cell density in thymus was, however, similar among irradiated and non-irradiated mice, owing to its smaller post-TBI weight compared to non-irradiated (6.6±0.7 mg vs. 18.4±1.5 mg, respectively, p<0.0001). Weights and cellularity of spleen, lymph nodes, and thymus in mice treated with PEG-IL11 singly or in combination with PEG-G-CSF or PEG-GM-CSF (n=12) were higher than those in non-PEG-IL11 groups (n=9). The apparent increased weight and cellularity of lymphoid organs in PEG-IL11 groups corresponded with an increased percentage of peripheral blood lymphocytes in PEG-IL11 groups compared to non-PEG-IL11 groups (65±2.7% vs. 52±3.1%, respectively, p=0.0222), as well as an apparent increased number of peripheral blood lymphocytes. These data illustrate the significant decrease in size and cellularity of lymphoid organs (spleen, lymph nodes, thymus) in H-ARS survivors at 1 yr post-LD65/30 compared to age-matched non-irradiated mice, and validate the murine H-ARS model as appropriate to investigate mechanisms and medical countermeasures for radiation-induced immunosuppression. In addition, medical countermeasures containing PEG-IL11 may alleviate some of the chronic immunosuppression characteristics of residual bone marrow damage (RBMD) by promoting regeneration of lymphoid organ mass and cellularity.

Figure 6A:
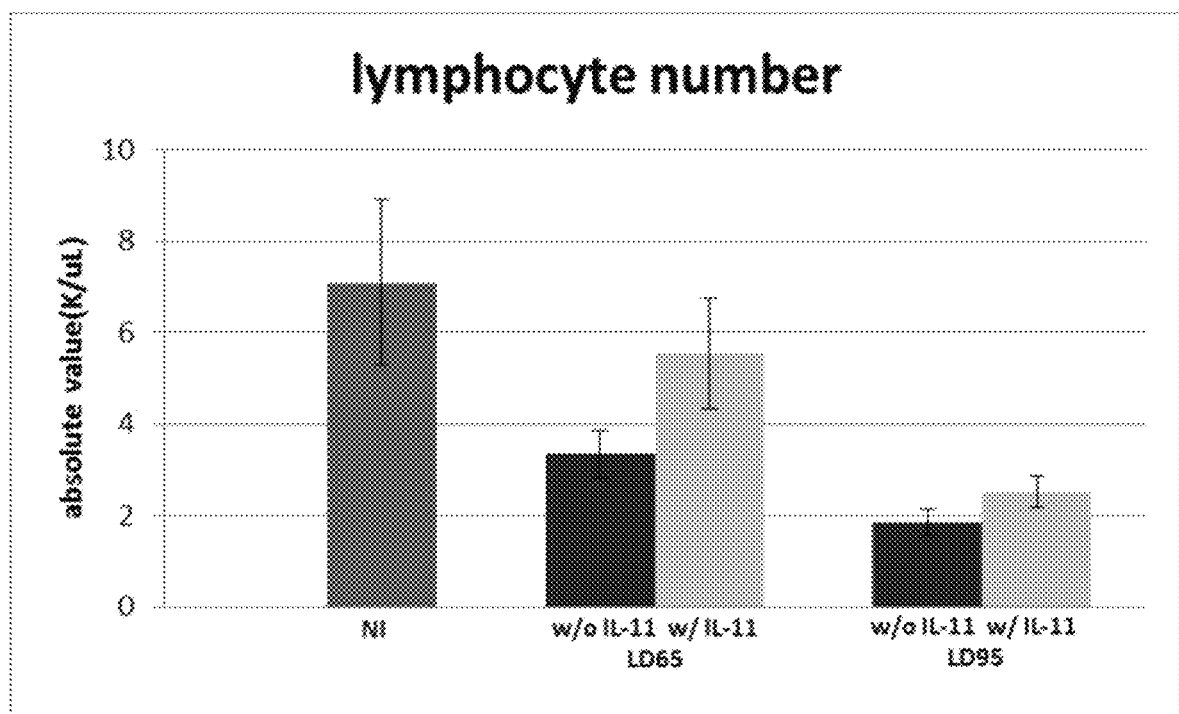
FIGS. 6A-6F show the absolute number of peripheral blood lymphocytes (FIG. 6A) and lymphocyte percentage (FIG. 6B) 1 year post-irradiation for nonirradiated mice and murine survivors of H-ARS treated with peg-HGF regimens containing PEG IL-11 or without PEG IL-11. N=8 mice in noninradiated group n=9-18 mice in each treatment group. Lymph node weight (FIG. 6C), spleen weight (FIG. 6D), thymus weight (FIG. 6E) and thymus cell number (FIG. 6F) one year post-irradiation are shown for nonirradiated mice and murine survivors of H-ARS treated with peg-HGF regimens containing PEG IL-11 or without PEG IL-11. N=10 in NI group and n=9-18 mice in each treatment group.
Figure 6B:
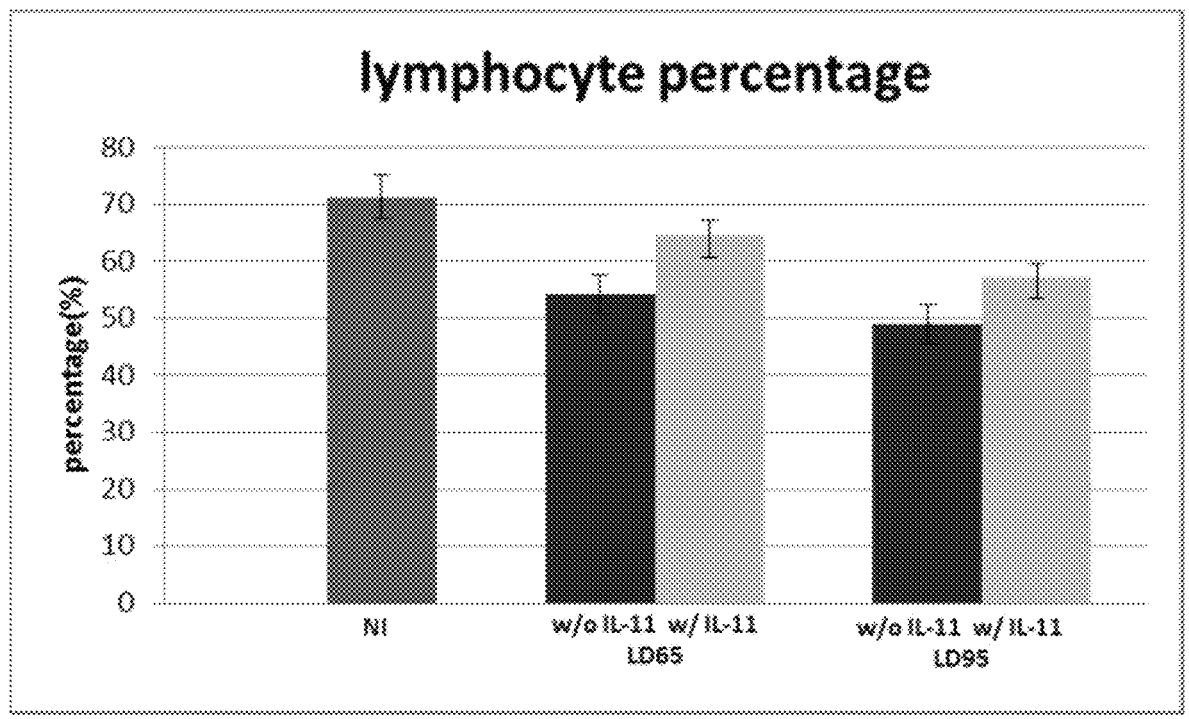
Figure 6C:
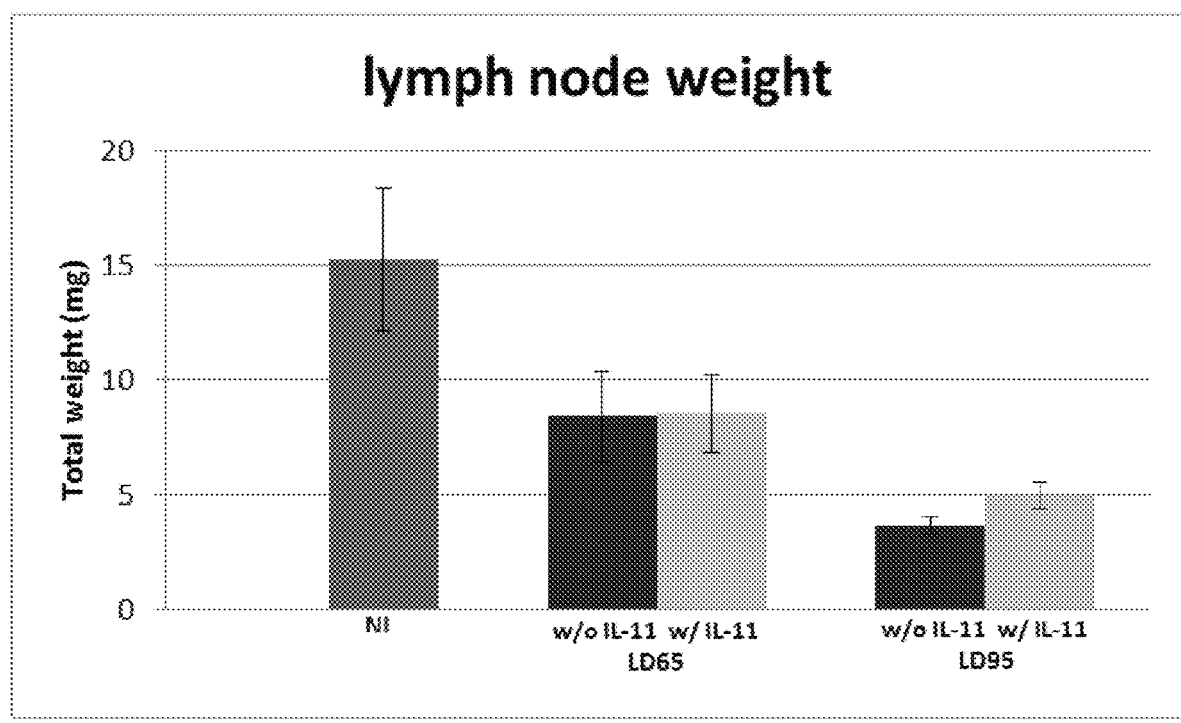
Figure 6D:
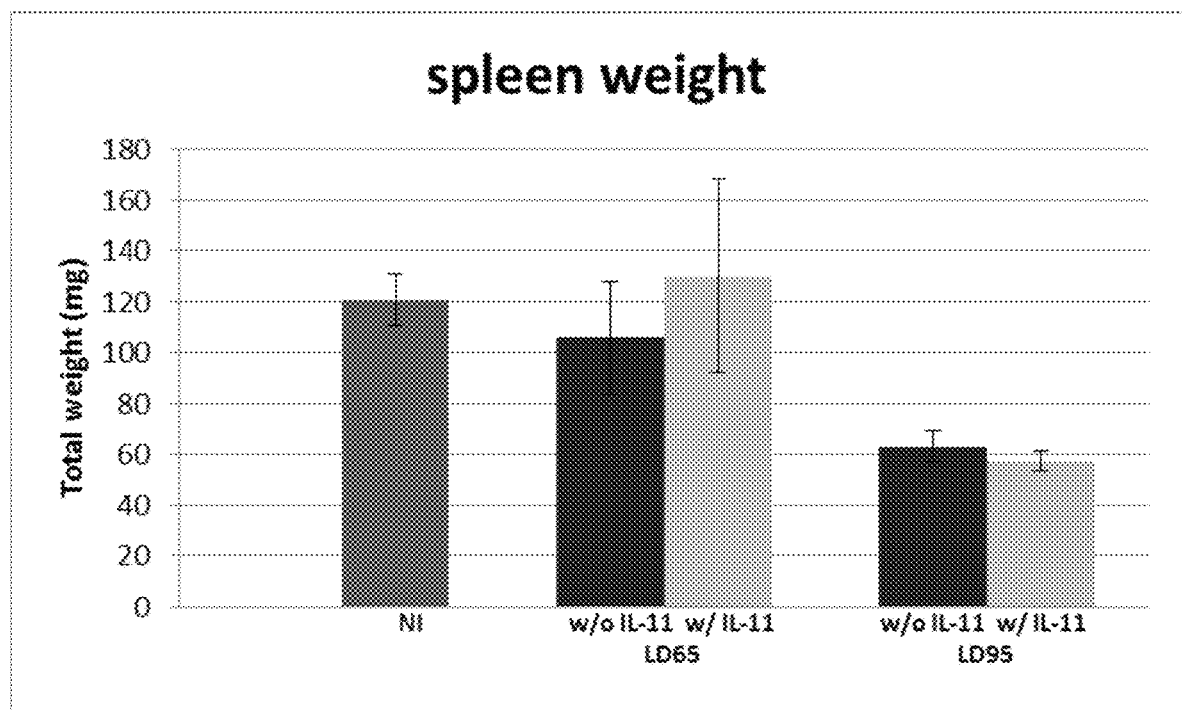
Figure 6E:
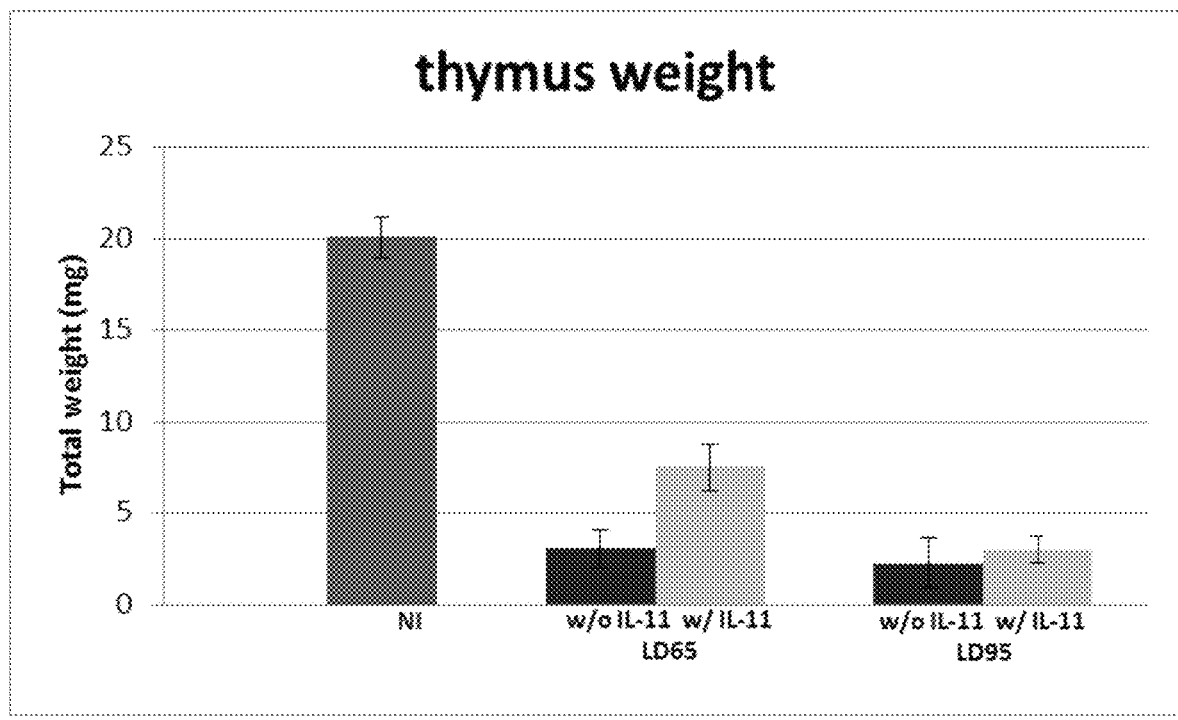
Figure 6F:
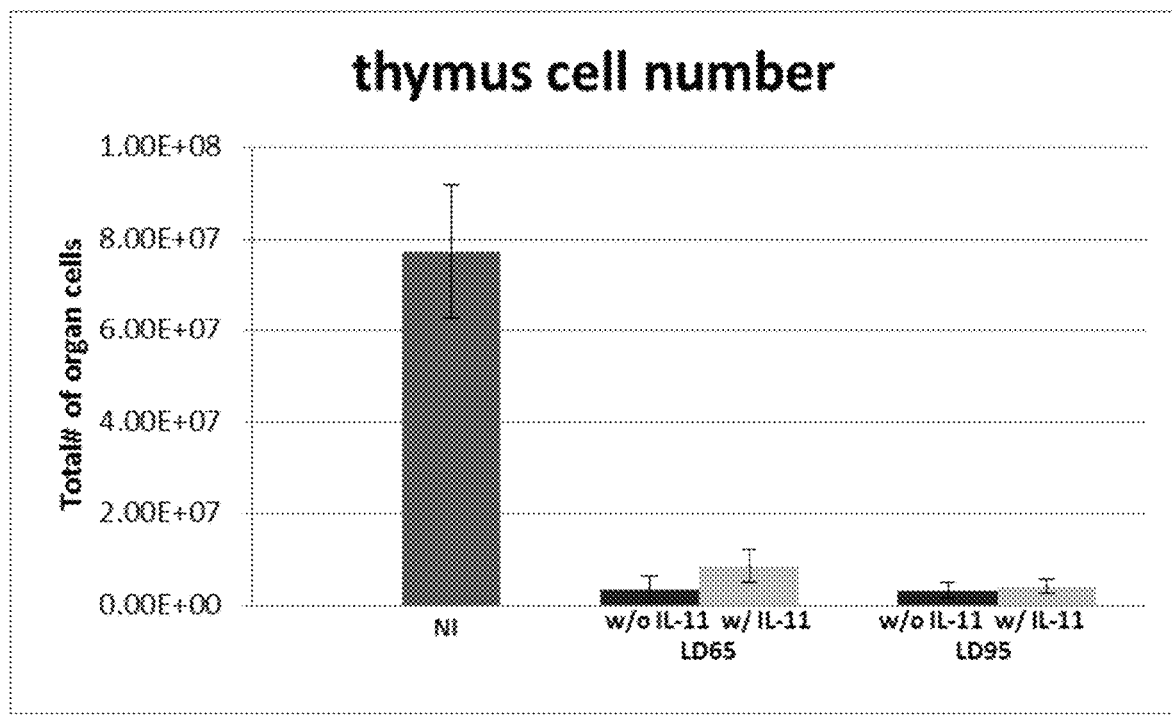

LD65/30 and LD95/30 H-ARS survivors from Example 1 and Example 10 were sacrificed 1 year post-irradiation and analyzed for blood lymphocyte populations, and mass and cellularity of lymphoid organs. As shown in FIGS. 6A-6F, the percentage and absolute number of peripheral blood lymphocytes in murine survivors of H-ARS treated 24 h post-irradiation with PEG IL-11 and combinations containing PEG IL-11 (PEG G-CSF+PEG IL-11; PEG-GM-CSF+PEG IL-11; and PEG-G-CSF+PEG-GM-CSF+PEG IL-11) were increased 1 year post irradiation compared to non-PEG-IL11-containing regimens (PEG-G-CSF; PEG-GM-CSF; PEG-G-CSF+PEG GM-CSF).

At 1 year post irradiation, the majority of lymphoid organs in H-ARS survivors weighed significantly less than those in non-irradiated mice (FIGS. 6A-6F). Reduced organ weight was found to be radiation dose-dependent with greater reductions in weight occurring in survivors of the LD95/30 compared to the LD65/30. The number of thymocytes and weight of the thymus were 20-fold and 5-fold less, respectively, than non-irradiated age-matched controls. As shown in FIGS. 6A-6F, treatment regimens containing PEG-IL11 (PEG IL-11; PEG G-CSF+PEG IL-11; PEG-GM-CSF+PEG IL-11; and PEG-G-CSF+PEG-GM-CSF+PEG IL-11) resulted in increased lymphoid organ weights and thymocyte number compared to non-PEG IL11 groups (PEG-G-CSF; PEG-GM-CSF; PEG-G-CSF+PEG GM-CSF).

Figure 7A:
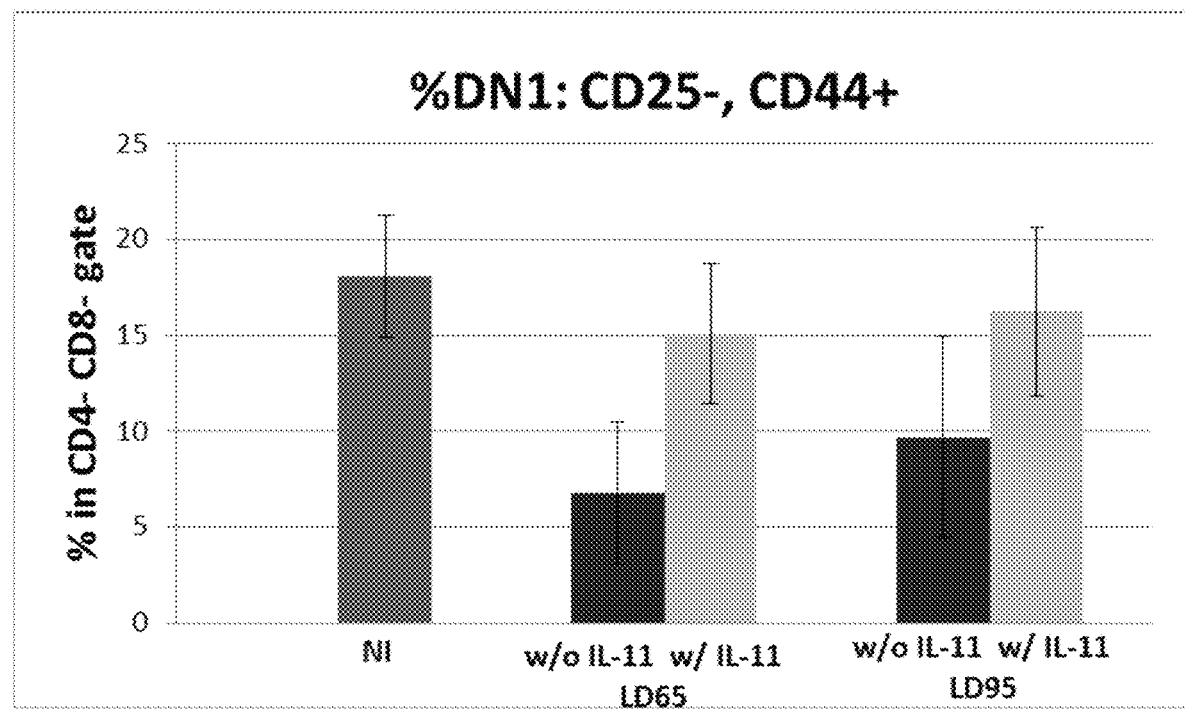
FIGS. 7A-7D show the effects of irradiation and PEG IL-11 treatment on T cell subsets one year post-irradiation.
Figure 7B:
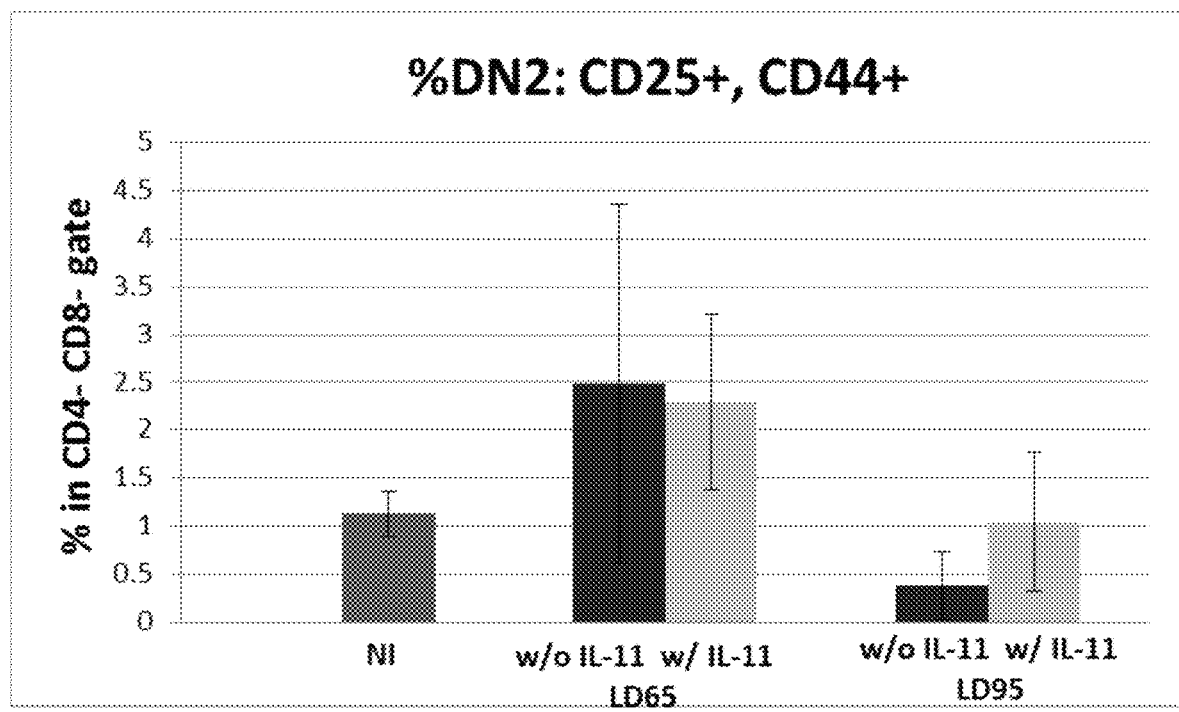
Figure 7C:
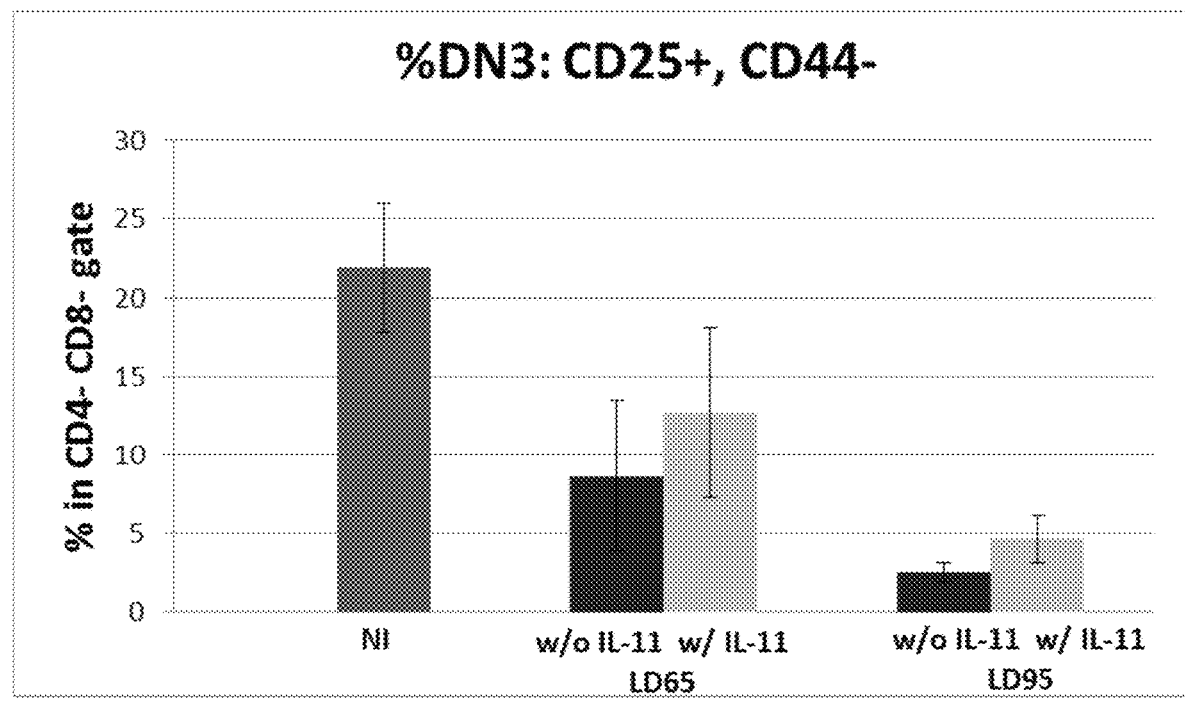
Figure 7D:
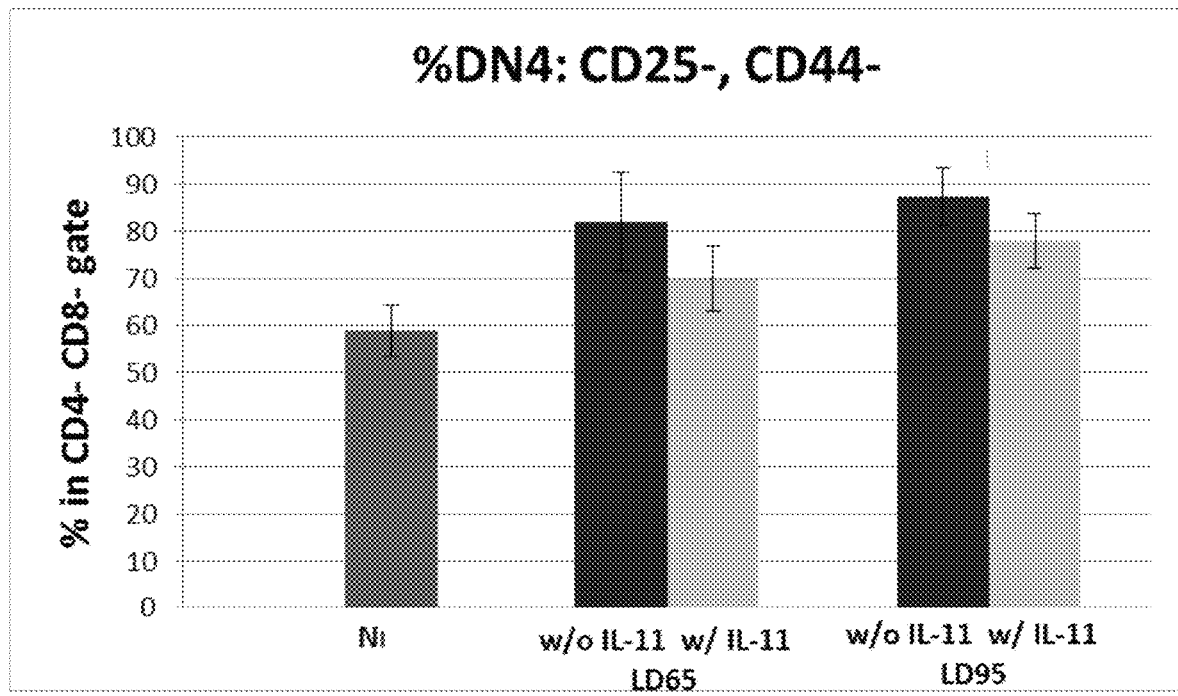

Progenitor T cells emigrating from the bone marrow to the thymus undergo progressive differentiation from double-negative (DN) to double-positive (DP) to single-positive CD4 or CD8 T cells. The immature DN thymocytes can be further divided into DN1 to DN4 based on their expression of CD44 and CD25. DN1: CD44+CD25−; DN2: CD44+CD25+; DN3: CD44-CD25+; DN4: CD44-CD25−. DN2 and DN3 are the most actively proliferating populations in the thymus. These T cell subsets in H-ARS survivors were analyzed by flow cytometry 1 year post irradiation. We found that irradiation results in a decreased DN3 percentage and increased DN4 percentage in the thymus, observed at 1 yr post-exposure (FIGS. 7A-7D). As shown in FIGS. 7A-7D, mice treated with PEG-IL11-containing regimens (PEG IL-11; PEG G-CSF+PEG IL-11; PEG-GM-CSF+PEG IL-11; and PEG-G-CSF+PEG-GM-CSF+PEG IL-11) displayed an increased percentage of DN3 cells and lower percentage of DN4 cells at 1 yr post-irradiation compared to mice receiving non-PEG IL11 regimens (PEG-G-CSF; PEG-GM-CSF; PEG-G-CSF+PEG GM-CSF).

These data demonstrate a radiation dose-dependent decrease in weight and cellularity of several lymphoid organs (lymph node, spleen, thymus) 1 yr following exposure to high dose rate lethal radiation (LD65/30 and LD95/30) in a murine model of H-ARS. Medical countermeasure treatments for H-ARS containing PEG-IL11, in addition to significantly enhancing 30-day survival, also appear to enhance immune reconstitution in H-ARS survivors, as evidenced by increased weight and cellularity of lymphoid organs, especially thymus, in survivors 1 yr post-LD95/30 or -LD65/30 irradiation. The data show a radiation-induced decrease in the percentage of DN3 thymocytes and increased percentage of DN4 thymocytes. Medical countermeasure H-ARS regimens containing PEG-IL11 resulted in partial normalization of these percentages 1 yr after exposure. PEG-IL11 may have a positive impact on some aspects of residual bone marrow damage (RBMD), including long-term immune suppression, via partial correction of the radiation dose dependent decrease in lymphoid organ mass and cellularity, as well as the disruption in thymic T cell development.

Example 10

This Example shows that treating LD65/30 irradiated mice with a single injection of long-acting Hematopoietic Growth Factors increases 30-day Survival in the Mouse ARS Survival Assay.

The efficacy of three individual HGFs and all possible combinations of the 3 proteins to increase 30 day survival of lethally irradiated mice was tested at an LD65/30 radiation dose (a dose of radiation expected to cause death to 65% of an exposed population within 30 days). This experiment was performed as described in Example 1 except that the radiation dose used was 872 cGy and there were 20 mice per test group (10 males/10 females). The three HGFs were the same ones used in Example 1. Irradiated mice received a single sc injection of vehicle solution or the proteins 24 h+4/−0 following irradiation.

As indicated in Table 10, mice treated with vehicle had a 30-day survival rate of 35%, which was lower than the survival rate of mice treated with PEG-IL-11 (65% survival rate), PEG-G-CSF (80% survival rate) or PEG-GM-CSF (70% survival rate). Treating irradiated mice with PEG GM-CSF+PEG IL-11 resulted in the highest survival rate (90% survival). The next most effective combination for increasing survival was the combination of all three growth factors (PEG IL-11+PEG G-CSF+PEG GM-CSF) (85% survival). All of the two and three protein combinations had survival rates equal to or higher than the survival rates of the individual proteins.

TABLE 10

30-day survival of LD65/30 (872 cGy) irradiated mice treated with a single sc injection of PEG IL-11 (0.3 mg/kg), PEG-G-CSF (1 mg/kg) or PEG muGM-CSF (1 mg/kg), or combinations of the proteins. There were 20 mice (10 males/10 females) per test group.

| Test Group | % 30-d survival | (# survivors/total mice) |
|---|---|---|
| 1. Vehicle | 35 | 7/20 |
| 2. PEG-G-CSF | 80 | 16/20 |
| 3. PEG GM-CSF | 70 | 14/20 |

TABLE 10-continued 30-day survival of LD65/30 (872 cGy) irradiated mice treated with a single sc injection of PEG IL-11 (0.3 mg/kg), PEG-G-CSF (1 mg/kg) or PEG muGM-CSF (1 mg/kg), or combinations of the proteins. There were 20 mice (10 males/10 females) per test group.

| Test Group | % 30-d survival | (# survivors/total mice) |
|---|---|---|
| 4. PEG IL-11 | 65 | 13/20 |
| 5. PEG-IL-11 + PEG-G-CSF | 80 | 16/20 |
| 6. PEG-IL-11 + PEG-GM-CSF | 90 | 18/20 |
| 7. PEG-GM + PEG-G-CSF | 80 | 16/20 |
| 8. PEG-IL-11 + PEG-GM-CSF + PEG-G-CSF | 85 | 17/20 |

This Example demonstrates that PEG-G-CSF, PEG-GM-CSF and PEG-IL-11 administered individually once by sc injection at 24 h post irradiation improve 30-day survival of LD65/30 irradiated mice compared to Vehicle. The Example further demonstrates that treating LD65/30 irradiated mice with combinations of two or three of the HGF proteins results in survival rates equal to or greater than the survival rates for the individual proteins.

Example 11

To investigate the effects of PEG HGFs on hematopoietic progenitors cells following lethal radiation mice were exposed to an LD95/30 radiation dose and treated 24+4/−0 h later with a single sc injection of the PEG HGFs described in Example 1.

Figure 8A:
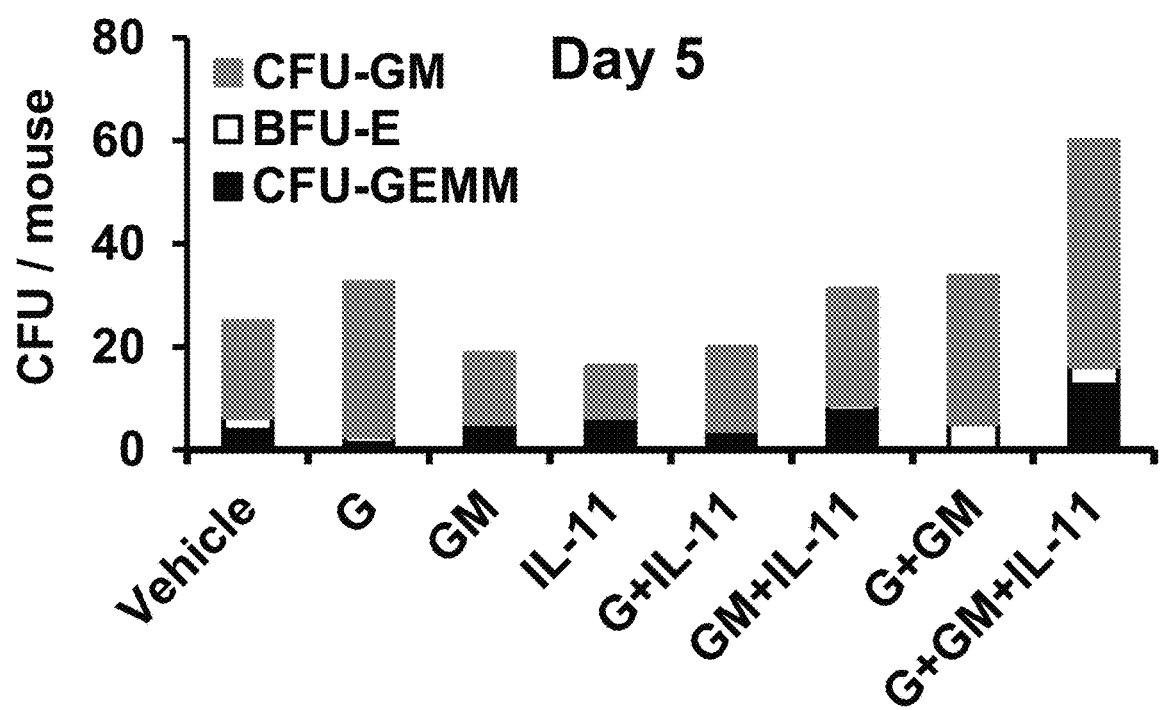
FIGS. 8A-8D show the numbers of hematopoietic progenitor cells per mouse on days 5 (FIG. 8A), 7 (FIG. 8B), 14 (FIG. 8C) and 30 (FIG. 8D) following treatment of LD95/30 irradiated mice with a single sc injection of vehicle solution (CA, control article) or PEG-G-CSF (G, 1 mg/kg), PEG muGM-CSF (GM, 1 mg/kg), PEG IL-11 (IL-11, 0.3 mg/kg) and all possible combinations of the proteins. NI indicates nonirradiated controls.
Figure 8B:
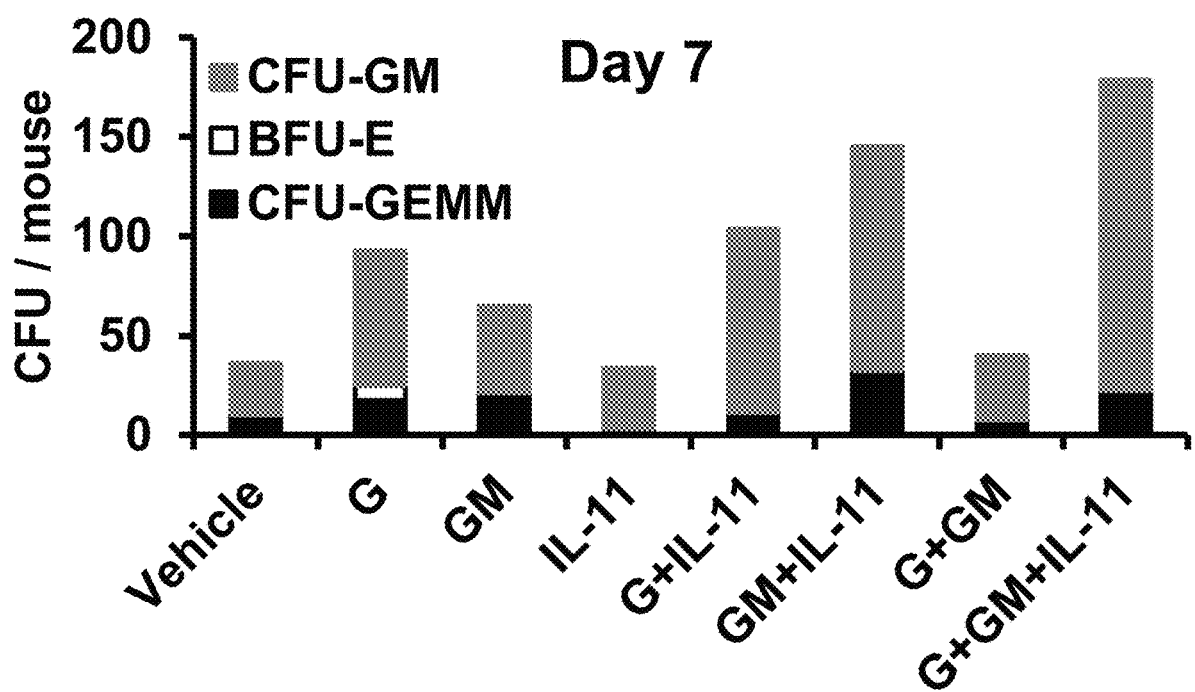
Figure 8C:
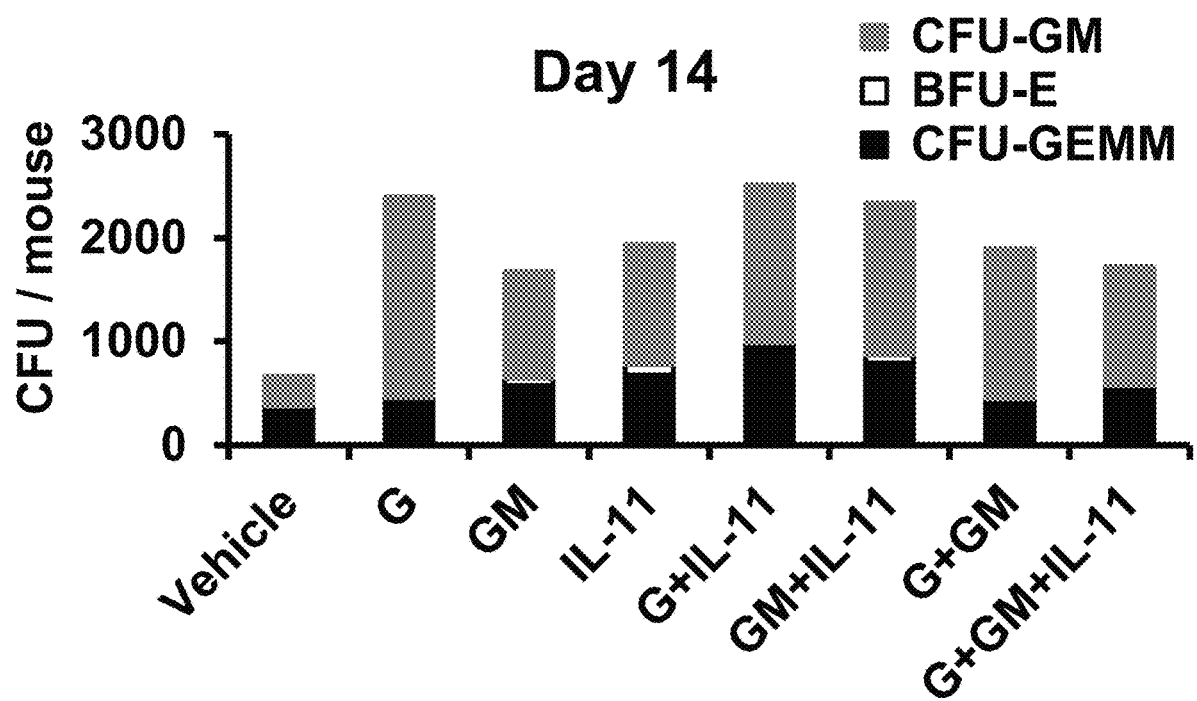
Figure 8D:
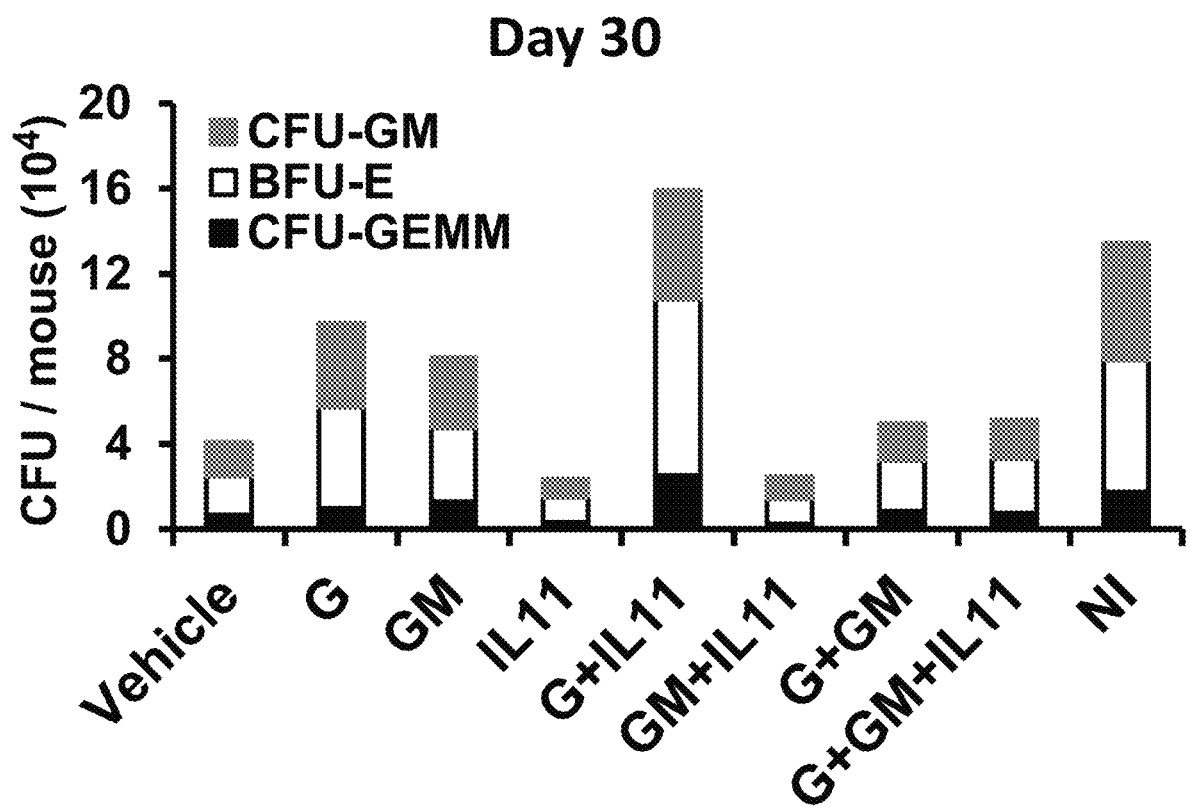

Doses of the drugs and other experimental details were as described in Example 1. On days 5, 7, 14 and 30 post irradiation 4 mice from each test group were sacrificed and the bone marrow cells from the 4 mice isolated and pooled. The pooled bone marrow was plated on media selective for hematopoietic progenitors cells: CFU-GM (granulocyte and macrophage progenitor cell colony forming units), BFU-E (burst forming unit erythroid progenitor cells), and CFU-GEMM (granulocyte, macrophage, erythroid and megakaryocyte progenitor cell colony-forming units). The results (FIGS. 8A-8D) show that treatment with the PEG-HGFs increased numbers of some hematopoietic progenitor cell types in the mice; particularly CFU-GM on 14 post irradiation compared to controls. The data demonstrate that treating irradiated mice with individual PEG HGFs or combinations of PEG HGFs once by sc injection 24+4/−0 h post irradiation stimulates increases in the number of hematopoietic progenitor cells (CFU-GM, CFU-GEMM, BFU-E) compared to vehicle-treated mice during the 30 days following radiation exposure.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention.

What is claimed is:

1. A method of improving 90 day to 12 month survival from hematopoietic acute radiation syndrome (H-ARS) in a subject who has been exposed to radiation and has delayed effects of acute radiation exposure (DEARE), comprising administering to the subject a combination therapy comprising an effective dose of an angiotensin-converting enzyme inhibitor (ACEI) and an effective dose of at least one hematopoietic growth factor (HGF) or protein analog thereof or combinations thereof;

wherein the ACEI is selected from the group consisting of lisinopril, perindopril, captopril, enalapril, and ramipril; and wherein the HGF or protein analog thereof is selected from the group consisting of:

a granulocyte colony-stimulating factor (G-CSF) analog comprising a methionine at the N-terminus of SEQ ID NO:1;

a G-CSF analog comprising a cysteine residue substituted for A141 of G-CSF having SEQ ID NO:1 and a serine residue substituted for C17 of G-CSF having SEQ ID NO:1;

a granulocyte-macrophage colony-stimulating factor (GM-CSF) analog (SEQ ID NO:2);

a GM-CSF analog comprising a cysteine substitution at amino acid position 3 of SEQ ID NO: 2;

an interleukin-11 (IL-11) analog comprising a cysteine residue added following the C-terminus of the protein having SEQ ID NO:3 or SEQ ID NO:7, wherein the P1 amino acid is deleted; and combinations thereof; and wherein the survival obtained by treatment with the combination of at least one HGF or protein analog thereof and the ACEI is greater than the survival obtained by treatment with at least one HGF or protein analog thereof alone or treatment with the ACEI alone.

2. The method of claim 1, wherein the subject has been exposed to a myelosuppressive dose amount of radiation.

3. The method of claim 1, wherein the G-CSF analog, the GM-CSF analog, or the IL-11 analog is modified with a polyethylene glycol (PEG).

4. The method of claim 1, wherein the improved survival correlates with accelerated hematopoietic recovery in the subject.

5. The method of claim 1, wherein the improved survival correlates with decreased lung morbidity in the subject.

6. The method of claim 1, wherein the improved survival correlates with decreased lung pneumonitis in the subject.

7. The method of claim 1, wherein the improved survival correlates with decreased lung fibrosis in the subject.

8. The method of claim 1, wherein the improved survival correlates with decreased kidney morbidity in the subject.

9. The method of claim 1, wherein the improved survival correlates with decreased heart morbidity in the subject.

10. The method of claim 1, wherein the effective dose of the ACEI is administered concurrently with, prior to, or after administration of the effective dose of the at least one HGF or protein analog thereof or combinations thereof.

11. The method of claim 1, wherein the effective dose of the at least one HGF or protein analog thereof is a single dose of 0.1 μg to 5 mg per kg of the subject.

12. The method of claim 1, wherein the subject is administered one or more single doses of the at least one HGF or protein analog thereof or combinations thereof.

13. The method of claim 1, wherein the subject is administered one or more doses of the at least one HGF or protein analog thereof or combination thereof beginning within 24 hours following the subject's exposure to the radiation.

14. The method of claim 1, wherein the effective dose of the ACEI is a dose of 1.3 to 50 mg/m2/day.

15. The method of claim 1, wherein the subject is administered the ACEI daily beginning within 7 days following the subject's exposure to the radiation.

16. The method of claim 1, wherein the subject is administered the ACEI daily beginning within 7 days following the subject's exposure to radiation and continuing for 7 to 150 days following the subject's exposure to radiation.

17. The method of claim 1, wherein the effective dose of the at least one HGF or protein analog thereof or combination thereof is administered to the subject beginning within 24 hours following radiation exposure and the effective dose of the ACEI is administered to the subject beginning within 7 days following radiation exposure.

18. The method of claim 1, wherein the effective dose of the at least one HGF or protein analog thereof or combination thereof is administered to the subject beginning within 24 hours following radiation exposure, and the effective dose of the ACEI is administered to the subject beginning within 7 days following radiation exposure and continuing for 7 to 150 days following the subject's exposure to radiation.

19. The method of claim 1, wherein the ACEI is lisinopril.

20. The method of claim 1, wherein the HGF protein analog is a combination of the HGF protein analogs, wherein the combination consists of a G-CSF analog, a GM-CSF analog and an IL-11 analog, and wherein each analog is modified with a polyethylene glycol (PEG).

* * * * *

SEQUENCE LISTING

<160> NUMBER OF SEQ ID NOS: 7

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 127
<212> TYPE: PRT
<213> ORGANISM: Homo sapiens

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 3
<211> LENGTH: 199
<212> TYPE: PRT

<213> ORGANISM: Homo sapiens

<400> SEQUENCE: 3

```
Met Asn Cys Val Cys Arg Leu Val Leu Val Leu Ser Leu Trp Pro
 1               5                  10                  15

Asp Thr Ala Val Ala Pro Gly Pro Pro Gly Pro Pro Arg Val Ser
                20                  25                  30

Pro Asp Pro Arg Ala Glu Leu Asp Ser Thr Val Leu Leu Thr Arg Ser
            35                  40                  45

Leu Leu Ala Asp Thr Arg Gln Leu Ala Ala Gln Leu Arg Asp Lys Phe
        50                  55                  60

Pro Ala Asp Gly Asp His Asn Leu Asp Ser Pro Thr Leu Ala Met
 65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
        195
```

<210> SEQ ID NO 4
<211> LENGTH: 191
<212> TYPE: PRT
<213> ORGANISM: Homo sapiens

<400> SEQUENCE: 4

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
```

```
                        145                 150                 155                 160
Gly Leu Leu Tyr Cys Phe Arg Lys Asp Met Asp Lys Val Glu Thr Phe
                        165                 170                 175
Leu Arg Ile Val Gln Cys Arg Ser Val Glu Gly Ser Cys Gly Phe
                        180                 185                 190

<210> SEQ ID NO 5
<211> LENGTH: 166
<212> TYPE: PRT
<213> ORGANISM: homo sapiens

<400> SEQUENCE: 5

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
                20                  25                  30
Cys Ser Leu Asn Glu Asn Ile Thr Val Pro Asp Thr Lys Val Asn Phe
            35                  40                  45
Tyr Ala Trp Lys Arg Met Glu Val Gly Gln Gln Ala Val Glu Val Trp
        50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 6
<211> LENGTH: 124
<212> TYPE: PRT
<213> ORGANISM: Mus musculus

<400> SEQUENCE: 6

Ala Pro Thr Arg Ser Pro Ile Ile Val Thr Arg Pro Trp Lys His Val
1               5                   10                  15
Glu Ala Ile Lys Glu Ala Leu Asn Leu Leu Asp Asp Met Pro Val Thr
                20                  25                  30
Leu Asn Glu Glu Val Glu Val Val Ser Asn Glu Phe Ser Phe Lys Lys
            35                  40                  45
Leu Thr Cys Val Gln Thr Arg Leu Lys Ile Phe Glu Gln Gly Leu Arg
        50                  55                  60
Gly Asn Phe Thr Lys Leu Lys Gly Ala Leu Asn Met Thr Ala Ser Tyr
65                  70                  75                  80
Tyr Gln Thr Tyr Cys Pro Pro Thr Pro Glu Thr Asp Cys Glu Thr Gln
                85                  90                  95
Val Thr Thr Tyr Ala Asp Phe Ile Asp Ser Leu Lys Thr Phe Leu Thr
            100                 105                 110
Asp Ile Pro Phe Glu Cys Lys Lys Pro Ser Gln Lys
        115                 120
```

```
                  115                 120

<210> SEQ ID NO 7
<211> LENGTH: 178
<212> TYPE: PRT
<213> ORGANISM: Homo sapiens

<400> SEQUENCE: 7

Pro Gly Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
                20                  25                  30

Arg Gln Leu Ala Ala Gln Leu Arg Asp Lys Phe Pro Ala Asp Gly Asp
            35                  40                  45

His Asn Leu Asp Ser Leu Pro Thr Leu Ala Met Ser Ala Gly Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
                100                 105                 110

Asp Arg Leu Leu Arg Arg Leu Gln Leu Leu Met Ser Arg Leu Ala Leu
            115                 120                 125

Pro Gln Pro Pro Pro Asp Pro Pro Ala Pro Pro Leu Ala Pro Pro Ser
    130                 135                 140

Ser Ala Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu
```